(12) United States Patent
Mrksich et al.

(10) Patent No.: US 9,074,300 B2
(45) Date of Patent: *Jul. 7, 2015

(54) POLYPEPTIDE IMMOBILIZATION

(75) Inventors: Milan Mrksich, Chicago, IL (US); Christian Hodneland, Brookline, MA (US)

(73) Assignee: The University of Chicago, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/984,948

(22) Filed: Feb. 4, 2011

(65) Prior Publication Data

US 2012/0142547 A1 Jun. 7, 2012

Related U.S. Application Data

(63) Continuation of application No. 11/645,095, filed on Dec. 21, 2006, now Pat. No. 7,888,055, which is a continuation of application No. 09/923,760, filed on Aug. 7, 2001, now Pat. No. 7,172,905.

(51) Int. Cl.
| | |
|---|---|
| *G01N 33/53* | (2006.01) |
| *C12Q 1/34* | (2006.01) |
| *C40B 30/04* | (2006.01) |
| *B82Y 30/00* | (2011.01) |
| *C07C 323/58* | (2006.01) |
| *C07F 9/40* | (2006.01) |
| *C07F 9/655* | (2006.01) |
| *G01N 33/543* | (2006.01) |

(Continued)

(52) U.S. Cl.
CPC .............. *C40B 30/04* (2013.01); *B82Y 30/00* (2013.01); *C07C 323/58* (2013.01); *C07F 9/4006* (2013.01); *C07F 9/4084* (2013.01); *C07F 9/65515* (2013.01); *G01N 33/54353* (2013.01); *G01N 33/551* (2013.01); *G01N 33/6845* (2013.01); *Y10S 530/812* (2013.01); *Y10S 530/815* (2013.01); *Y10S 530/811* (2013.01)

(58) Field of Classification Search
CPC ............... G01N 33/54353; G01N 33/6845; G01N 2610/00
See application file for complete search history.

(56) References Cited

U.S. PATENT DOCUMENTS

| 4,981,611 A | 1/1991 | Kolattukudy et al. |
| 5,196,478 A | 3/1993 | Varga et al. |

(Continued)

FOREIGN PATENT DOCUMENTS

| EP | 402 226 A1 | 12/1990 |
| EP | 645 397 A1 | 3/1995 |

(Continued)

OTHER PUBLICATIONS

Kodadek, T. Protein microarrays: prospects and problems. Chemistry & Biology 2001, vol. 8, pp. 105-115.*

(Continued)

*Primary Examiner* — Shafiqul Haq
(74) *Attorney, Agent, or Firm* — Brinks Gilson & Lione

(57) ABSTRACT

The present invention provides a method, comprising (a) providing a reactant ligand attached to a substrate; (b) contacting the substrate with a fusion polypeptide, said fusion polypeptide comprising a capture polypeptide fused to a display polypeptide under conditions such that said reactant ligand covalently binds to said capture polypeptide; and (c) analyzing said display polypeptide.

13 Claims, 13 Drawing Sheets

(51) Int. Cl.
*G01N 33/551* (2006.01)
*G01N 33/68* (2006.01)

(56) References Cited

U.S. PATENT DOCUMENTS

| | | | |
|---|---|---|---|
| 5,223,488 | A | 6/1993 | Ogata et al. |
| 5,232,913 | A | 8/1993 | Ohmori et al. |
| 5,274,177 | A | 12/1993 | Ohmori et al. |
| 5,352,594 | A | 10/1994 | Poulouse |
| 5,389,536 | A | 2/1995 | Gray et al. |
| 5,541,162 | A | 7/1996 | Ohmori et al. |
| 5,545,621 | A | 8/1996 | Kauvar et al. |
| 5,556,942 | A | 9/1996 | Kauvar et al. |
| 5,599,903 | A | 2/1997 | Kauvar et al. |
| 5,616,563 | A | 4/1997 | Creighton et al. |
| 5,646,177 | A | 7/1997 | Koch et al. |
| 5,654,176 | A | 8/1997 | Smith |
| 5,767,086 | A | 6/1998 | Kauvar et al. |
| 5,773,236 | A | 6/1998 | Diwu et al. |
| 5,804,604 | A | 9/1998 | Frankel et al. |
| 5,880,097 | A | 3/1999 | Lyttle et al. |
| 5,908,919 | A | 6/1999 | Kauvar et al. |
| 5,955,432 | A | 9/1999 | Kauvar et al. |
| 6,013,462 | A | 1/2000 | Kauvar et al. |
| 6,030,950 | A | 2/2000 | Ohlenschlager |
| 6,066,715 | A | 5/2000 | Desmarais et al. |
| 6,184,344 | B1 | 2/2001 | Kent et al. |
| 6,194,550 | B1 | 2/2001 | Gold et al. |
| 6,207,446 | B1 | 3/2001 | Szostak et al. |
| 6,214,553 | B1 | 4/2001 | Szostak et al. |
| 6,329,209 | B1 * | 12/2001 | Wagner et al. ................ 506/13 |
| 6,537,749 | B2 | 3/2003 | Kuimelis et al. |
| 6,764,768 | B2 | 7/2004 | Mrksich et al. |
| 6,972,196 | B1 | 12/2005 | Mrksich et al. |
| 2002/0182597 | A1 | 12/2002 | Kuimelis et al. |
| 2005/0255582 | A1 | 11/2005 | Mrksich et al. |

FOREIGN PATENT DOCUMENTS

| | | |
|---|---|---|
| WO | WO 91/00357 A1 | 1/1991 |
| WO | WO 95/08563 A1 | 3/1995 |
| WO | WO 95/20601 A1 | 8/1995 |
| WO | WO 96/22791 A1 | 8/1996 |
| WO | WO 98/14476 A1 | 4/1998 |
| WO | WO 98/16508 A2 | 4/1998 |
| WO | WO 98/30575 A1 | 7/1998 |
| WO | WO 98/30578 A1 | 7/1998 |
| WO | WO 98/47910 A1 | 10/1998 |
| WO | WO 99/34839 A1 | 7/1999 |
| WO | WO 99/51773 A1 | 10/1999 |
| WO | WO 01/04265 A2 | 1/2001 |

OTHER PUBLICATIONS

Alam, J., et al. "Reporter genes: Application to the study of mammalian gene transcription," Analytical Biochemistry, vol. 188, 1990, pp. 245-254.

Alligood, K., et al., "The Formation of a Covalent Complex Between a Dipeptide Ligand and the src SH2 Domain," Bioorg Med Chem Lett. vol. 8, 1998, pp. 1189-1194.

Arenkov et al. "Protein Microchips: Use for Immunoassay and Enzymatic Reactions" Analytical Biochemistry 2000 278(2) pp. 123-131.

Austin, C.,et al., "Cellular Migration Patterns in the Developing Mouse Cerebral Cortex," Development, vol. 110, 1990, pp. 713-732.

Bamdad, C., "A DNA Self-Assembled Monolayer for the Specific Attachment of Unmodified Double- or Single-Stranded DNA," Biophys Journal, vol. 75, 1998, pp. 1997-2003.

Bandmann, N., et al., "Genetic Engineering of the *Fusarium solani Pisi* Lipase Cutinase for Enhanced Partitioning in PEG-phosphate Aqueous Two-phase Systems," *Journal of Biotechnology*, vol. 79, 2000, pp. 161-172.

Bechtold, N., and G. Pelletier 1998. In planta *Agrobacterium*-mediated transformation of adult *Arabidopsis thaliana* plants by vacuum infiltration, Methods Mol Biol., 82:259-266.

Becker, D.M., et al., "High-efficiency Transformation of Yeast by Electroporation," Methods Enzymology, vol. 194, 1991, pp. 182-187.

Beggs, J.D. "Transformation of Yeast by a Replicating Hybrid Plasmid," Nature, vol. 275, 1978, pp. 104-109.

Berger, J., et al., "Secreted Placental Alkaline Phosphatase: A Powerful New Qunatitative Indicator of Gene Expression in Eukaryotic Cells," Gene, vol. 66, 1988, pp. 1-10.

Berggren, K., et al., "Partitioning of Peptides and Recombinant Protein-Peptide Fusions in Thermoseparating Aqueous Two-phase Systems: Effect of Peptide Primary Structure," Journal of Chromatogr B Biomed Sci Appl., vol. 743, 2000, pp. 295-306.

Berman, H.A., et al., "Fluorescent Phosphonate Label for Serine Hydrolases, Pyrenebutyl Methylphosphonofluoridate: Reaction with Acetylcholinesterase." Biochemistry, vol. 17, 1978, pp. 1704-1713.

Blaydes, J.Petal., "The Development and use of Phospho-Specific Antibodies to Study Protein Phosphorylation," Methods Mol Biol. vol. 99, 2000, pp. 177-189.

Bodine, D.M., et al., "Survival and Retrovirus Infection of Murine Hematopoietic Stem Cells In Vitro: Effects of 5-FU and Method of Infection," Experimental Hematology, vol. 19, 1991, pp. 206-212.

Born, Timothy et al., "4-(Fluoromethyl)phenyt Phasphate Acts As a Mechanism-Based Inhibitor of Calcineurin", Jorn. Bio. Chem., vol. 270, No. 43, 1995, pp. 25651-25655.

Brown, M.T., et al., "Regulation, Substrates and Functions of src," Biochim Biophys Acta., vol. 1287, 1996, pp. 121-149.

Burgener et al. "Synthesis of a Stable and Specific Surface Plasmon Resonance Biosensor Surface Employing Covalently Immobilized Peptide Nucleic Acids" Bioconjugate Chemistry 2000 11(6) pp. 749-754.

Capecchi, M.R. "High Efficiency Transformation by Direct Microinjection of DNA Into Cultured Mammalian Cells," Cell, vol. 22, 1980, pp. 479.

Cavalier et al, "Covalent inhibition of digestive lipases by chiral phosphonates," Accounts of Chemical Research, 2000, vol. 33, No. 9, pp. 579-589.

Case, M.E., et al., "Efficient Transformation of *Neurospora crassa* by Utilizing Hybrid Plasmid DNA," Proceedings of the National Academy of Sciences of the United States of America, vol. 76, Oct. 1996, pp. 5259-5263.

Cepko, C.L., et al., "Construction and Applications of a Highly Transmissible Murine Retrovirus Shuttle Vector," Cell, vol. 37, Jul. 1984, pp. 1053-1062.

Chalfie, M., et al., "Green Fluorescent Protein as a Marker for Gene Expression," Science, vol. 263, Feb. 11, 1994, pp. 802-805.

Chaney, W.G., et al., "High-frequency Transfection of CHO Cells Using Polybrene," Somatic Cell and Molecular Genetics, vol. 12, Jan. 1986, pp. 237-244.

Chapman, R., et al., "Surveying for Surfaces That Resist the Adsorption of Proteins," Journal of American Chem. Society, vol. 122, 2000, pp. 8303-8304.

Chen, C., et al., "Calcium Phosphate-Mediated Gene Transfer: A Highly Efficient Transfection System for Stably Transforming Cells with Plasmid DNA," BioTechniques, vol. 6, No. 7, 1988, pp. 632-638.

Chen, C.S., et al., "Geometric Control of Cell Life and Death." Science, vol. 276, 1997, pp. 1425-1428.

Chmura, Albert et al., "Antibodies with Infinite Affinity", PNAS, vol. 98, No. 15, 2001, pp. 8480-8484.

Cohen, S.N., et al., "Nonchromosomal Antibiotic Resistance in Bacteria: Genetic Transformation of *Escherichia coli* by R-Factor DNA," Proceedings of the National Academy of Sciences of the United States of America, vol. 69, No. 8, Aug. 1972, pp. 2110-2114.

Damrongchai et al. "Self-assembling of Glutathione S-transferase/Calmodulin Fusion Protein on a Chemically Modified Gold Surface" J. of Biotechnology 1997 55(2) pp. 125-133.

de Louvencourt, L., et al., "Transformation of *Kluyveromyces lactis* by Killer Plasmid DNA," Journal of Bacteriology, vol. 154, No. 2, May 1983, pp. 737-742.

Deussen, H.J., et al., "Design and Synthesis of Triglyceride Analogue Biotinylated Suicide Inhibitors for Directed Molecular Evolution of Lipolytic Enzymes," Bioorg Med Chem Lett., vol. 10, 2000, pp. 2027-2031.

(56) References Cited

OTHER PUBLICATIONS

Deussen, H.J., et al., "A Novel Biotinylated Suicide Inhibitor for Directed Molecular Evolution of lipolytic Enzymes," *Bioorg Med Chem.*, vol. 8, 2000, pp. 507-513.

de Wet, J.R., et al., "Firefly Luciferase Gene: Structure and Expression in Mammalian Cells," *Molecular Cellular Biology*, vol. 7, Feb. 1987, pp. 725-737.

Elroy-Stein, O., et al., "Cytoplasmic Expression System Based on Constitutive Synthesis of Bacteriophage T7 RNA Polymerase in Mammalian Cells," *Proceedings of the National Academy of Sciences of the United States of America*, vol. 87, No. 17, Sep. 1990, pp. 6743-6747.

Escudero, J., et al., "Transfer and Integration of T-DNA without Cell Injury in the Host Plant," *Plant Cell*, vol. 9, Dec. 1997, pp. 2135-2142.

Fekete, D.M., et al., "Retroviral Infection Coupled with Tissue Transplantation Limits Gene Transfer in the Chicken Embryo," *Proceedings of the National Academy of Sciences of the United States of America*, vol. 90, No. 6, Mar. 15, 1993, pp. 2350-2354.

Feigner, P.L., et al., "Lipofectin: A Highly Efficient, Lipid-Mediated DNA-transfection Procedure," *Proceedings of the National Academy of Sciences of the United States of America*, vol. 84, No. 21, Nov. 1, 1987, pp. 7413-7417.

Fieck, A., et al., "Modifications of the *E.coli* Lac Repressor for Expression in Eukaryotic Cells: Effects of Nuclear Signal Sequences on Protein Activity and Nuclear Accumulation," *Nucleic Acids Research*, vol. 20, No. 7, 1992, pp. 1785-1791.

Finer, J.J., et al., "Particle Bombardment Mediated Transformation," *Current Topics in Microbiology and Immunology*, vol. 240, 1999, pp. 59-80.

Fleer, R., et al., "Stable Multicopy Vectors for High-level Secretion of Recombinant Human Serum Albumin by *Kluyverornyces* Yeasts," *Biotechnology (N Y)*, vol. 9, 1991, pp. 968-975.

Fromm, M., et al., "Expression of Genes Transferred Into Monocot and Dicot Plant Cells by Electroporation", *Proceedings of the National Academy of Sciences of the United States of America*, vol. 82, No. 17, Sep. 1, 1985, pp. 5824-5828.

Fujita, T., et al., "Regulation of Human Interleukin-2 Gene: Functional DNA Sequences in the 5' Flanking Region for the Gene Expression in Activated T Lymphocytes," *Cell*, vol. 46, Aug. 1, 1986, pp. 401-407.

Gietz, R.D., et al., "Growth and Transformation of *Saccharomyces cerevisiae*," In Cells: A Laboratory manual. vol. 1.

Gorman, C.M., et al., "Recombinant Genomes Which Express Chloramphenicol Acetyltransferase in Mammalian Cells," *Molecular and Cellular Biology*, vol. 2, No. 9, Sep. 1982, pp. 1044-1051.

Graham, F.L., et al., "A New Technique for the Assay of Infectivity of Human Adenovirus 5 DNA," *Virology*, vol. 52, 1973, pp. 456-467.

Hanahan, D. "Studies on Transformation of *Escherichia coli* with Plasmids," *Journal of Molecular Biology*, vol. 166, 1983, pp. 557-580.

Hansen, G., et al., "Lessons in Gene Transfer to Plants by a Gifted Microbe," *Current Topics in Microbiology and Immunology*, vol. 240, 1999, pp. 1-57.

Hansen, G., et al., "Recent Advances in the Transformation of Plants," *Trends Plant Science*, vol. 4, No. 6, 1999, pp. 226-231.

Hickman, James et al., "Molecular Self-Assembly of Two-Terminal, Voltammetric Microsensors with Internal References", *Science*, vol. 252, pp. 688-691.

Hinnen, A., et al., "Transformation of Yeast," *Proceedings of the National Academy of Sciences of the United States of America*, vol. 75, No. 4, Apr. 1978, pp. 1929-1933.

Hodneland, C., et al., "Biomolecular Surfaces that Release Ligands Under Electrochemical Control," *Journal of American Chem. Soc.* vol. 122, 2000, pp. 4235-4236.

Hoffman, F. "Laser Microbeams for the Manipulation of Plant Cells and Subcellular Structures," *Plant Science*, vol. 113, 1996, pp. 1-11.

Houseman, B.T., et al., "The Microenvironment of Immobilized Arg-Gly-Asp Peptides is an Important Determinant of Cell Adhesion," *Biomaterials*, vol. 22, 2001, pp. 943-955.

Hunter, T. "The Croonian Lecture 1997. The phosphorylation of Proteins on Tyrosine: Its Role in Cell Growth and Disease," *Philos Trans R Soc Lond B Biol Sci.*, vol. 353, 1998, pp. 583-605.

Ishiura, M., et al., "Phage Particle-Mediated Gene Transfer to Cultured Mammalian Cells," *Molecular and Cellular Biology*, vol. 2, No. 6, Jun. 1982, pp. 607-616.

Ito, H., et al., "Transformation of Intact Yeast Cells Treated with Alkali Cations," *Journal of Bacteriology*, vol. 153, No. 1, Jan. 1983, pp. 163-168.

Ito, Yoshihiro et al., ":Patterrned Immobilization of Thermoresponsive Polymer", *Langmuir*, vol. 13, 1997, pp. 2756-2759.

Kaufman, R.J., et al.; "Selection and Amplification of Heterologous Genes Encoding Adenosine Deaminase in Mammalian Cells," *Proceedings of the National Academy of Sciences of the United States of America*, vol. 83, No. 10, May 15, 1986, pp. 3136-3140.

Kawai, S., et al., "New Procedure for DNA Transfection with Polycation and Dimethyl Sulfoxide," *Molecular and Cellular Biology*, vol. 4, No. 6, Jun. 1984, pp. 1172-1174.

Kelly, J.M., et al., "Transformation of *Aspergillus niger* by the amdS gene of *Aspergillus nidulans*," *Embo Journal*, vol. 4, 1985, pp. 475-479.

Kim, Kyeong K. et al., "Crystal Structure of Carboxylesterase From *Psuedimonas flourescebs*, an a/ß Hydrolase With Broad Substrate Specificity", *Structure*, Vo 5, 1997, pp. 1571-1584.

Kim, Y.S., et al., "Cloning of *Pseudomonas fluorescens* Carboxylesterase Gene and Characterization of its Product Expressed in *Escherichia coli*," Biosci Biotechnol Biochem., vol. 58, 1994, pp. 111-116.

Kitz, R., et al., "Esters of Methanesulfonic Acid as Irreversable Inhibitors of Acetylcholinesterase", *J. Biol. Chem.*, vol. 237, 1962, pp. 3245.

Leduc, N., et al., "Isolated Maize Zygotes Mimic In Vivo Embryogenic Development and Express Microinjected Genes When Cultured In Vitro," *Dev. Biol.* vol. 10, 1996, pp. 190-203.

Lemischka, I.R., et al., "Developmental Potential and Dynamic Behavior of Hematopoietic Stem Cells," *Cell*, 45, Jun. 20, 1986, pp. 917-927.

Littlefield, J.W. "Selection of Hybrids from Matings of Fibroblasts In Vitro and Their Presumed Recombinants," *Science*, vol. 145, No. 3633, Aug. 14, 1964, pp. 709-710.

Longhi, S., et al., "Structure-activity of Cutinase, a Small Lipolytic Enzyme," *Biochim Biophys Acta.*, vol. 1441, 1999, pp. 185-196.

Lopata, M.A., et al., "High-level Transient Expression of a Chloramphenicol Acetyl Transferase Gene by DEAEdextran-mediated DNA Transfection Coupled with a Dimethyl Sulfoxide or Glycerol Shock Treatment," *Nucleic Acids Research*, vol. 12, No. 14, 1984, pp. 5707-5717.

Luk, Y.-Y., et al., "Self-Assembled Monolayers of Alkanethiolates Presenting Mannitol Groups are Inert to Protein Adsorption and Cell Attachment," *Langmuir*, vol. 16, 2000, pp. 9604-9608.

MacBeath et al. "Printing Proteins as Microarrays for High-throughput Function Determination" *Science* 2000, 289 (5485) pp. 1760-1763.

Mandel, M., et al., "Calcium-Dependent Bacteriophage DNA Infection", *Journal of Molecular Biology*, vol. 53, 1970, pp. 159-162.

Martinez, C., et al., "*Fusarium solani* Cutinase is a Lipolytic Enzyme with a Catalytic Serine Accessible to Solvent," *Nature*, vol. 356, 1992, pp. 615-618.

Martinez, C., et al., "Cutinase, a Lipolytic Enzyme with a Preformed Oxyanion Hole," *Biochemistry*, vol. 33, 1994, pp. 83-89.

Miller, A.D., et al., "Redesign of Retrovirus Packaging Cell Lines to Avoid Recombination Leading to Helper Virus Production," *Molecular and Cellular Biology*, vol. 6, No. 8, Aug. 1986, pp. 2895-2902.

Miller, L.K. "Baculoviruses as Gene Expression Vectors," *Annu. Rev. Microbiol.*, vol. 42, 1988, pp. 177-199.

Mrksich, M. "A Surface Chemistry Approach to Studying Cell Adhesion," *Chem. Soc. Rev.*, vol. 29, 2000, pp. 267-273.

Mrksich, M., et al. "Using Microcontact Printing to Pattern the Attachment of Mammalian Cells to Self-Assembled Monolayers of Alkanethiolates on Transparent Films of Gold and Silver," *Exp Cell Res.*, vol. 235, 1997, pp. 305-313.

(56) References Cited

OTHER PUBLICATIONS

Mrksich, M., and G. Whitesides, "Patterning Self-Assembled Monolayers Using Microcontact Printing: a New Technology for Biosensors", *TIBTECH*, 1995, vol. 13, pp. 228-235.

Mrksich, M., and G. Whitesides, "Using Self-Assembled Monolayers That Present Olio (ethylene glycol) Groups to Control the Interactions of Proteins with Surfaces", *American Chemical Society*, 1997, pp. 361-373.

Myers, Jason K. et al., "Mechanism-Based Inactivation of Prostatic Scid Phosphatse", *Science*, vol. 262, 1993, pp. 1451-1453.

Myers, Jason et al., "Motifs for Metallophosphatase Inhibition," *J. Am. Chem. Soc.*, vol. 119, 1997, pp. 3163-3164.

Myers, Jason K., "Substituent Effects on the Mechanism-Based Inactivation of Prostatic Acid Phosphatase", *J. Med. Chem.*, vol. 117, 1995, pp. 11049-11054.

Neumann, E., et al., "Gene Transfer Into Mouse Lyoma Cells by Electroporation in High Electric Fields," *EMBO Journal*, vol. 1, No. 7, 1982, pp. 841-845.

Okabayashi, Y., et al. "Interaction of Shc with Adaptor Protein Adaptins," *J Biol Chem.*, vol. 271, 1996, pp. 5265-5269.

Ou-Lee, T.M., "Expression of a Foreign Gene Linked to Either a Plant-Virus or a *Drosophila* Promoter, After Electroporation of Protoplasts of Rice, Wheat and Sorghum," *Proceedings of the National Academy of Sciences of the United States of America*, vol. 83, No. 18, Sep. 15, 1986, pp. 6815-6819.

Pacofsky, Gregory J., "Potent Dipeptide Inhibitors of the pp60c-src SH2 Domain", *J. Med. Chem.*, vol. 41, 1998, pp. 1894-1908.

Palmer, T.D., et al., "Efficient Retrovirus-Mediated Ttransfer and Expression of a Human Adenosine Deaminase Gene in Diploid Skin Fibroblasts from an Adenosine Deaminase-Deficient Human," *Proceedings of the National Academy of Sciences of the United States of America*, vol. 84, No. 4, Feb. 15, 1987, pp. 1055-1059.

Pear, W. S., et al., "Production of High-H-free Retroviruses by Transient Transfection," *Proceedings of the National Academy of Sciences of the United States of America*, vol. 90,. No. 18, Sep. 15, 1993, pp. 8392-8396.

Ploemen et al. "Irreversible Inhibition of Human Glutathione S-Transferase Isoenzymes by Tetrachloro-1,4-Benzoquinone and Its Glutathione Conjugate" *Biochemical Pharmacology* 1991 41 (11) pp. 1665-1669.

Potter, H. "Electroporation in Biology: Methods, Applications, and Instrumentation," *Analytical Biochemistry*, vol. 174, 1988, pp. 361-373.

Potter, H., et al., "Enhancer-Dependent Expression of Human Kappa Immunoglobulin Genes Introduced into Mouse Pre-B Lymphocytes by Electroporation," *Proceedings of the National Academy of Sciences of the United States of America*, vol. 81, 1984, pp. 7161-7165.

Quinn et al. "Biosensor-based Estimation of Kinetic and Equilibrium Constants" *Analytical Biochemistry* 2001 290(1) pp. 36-46.

Rassoulzadegan, M., et al., "High Frequency of Gene Transfer After Fusion Between Bacteria and Eukaryotic Cells," *Nature*, vol. 295, Jan. 21, 1982, pp. 257-259.

Rhodes, J.K., et al., "Genetically Transformed Maize Plants from Protoplasts," *Science*, vol. 240, 1988, pp. 204-207.

Roberts, C., et al., "Using Mixed Self-Assembled Monolayers Presenting RGD and (EG)3OH Groups to Characterize Long-Term Attachment of Bovine Capillary Endothelial Cells to Surfaces",*J Am Chem Soc.*, vol. 120 1998, pp. 6548-6555.

Rose, J.K., et al., "A New Cationic Liposome Reagent Mediating Nearly Quantitative Transfection of Animal Cells," *BioTechniques*, vol. 10, 1991, pp. 520-525.

Sandri-Goldin, R.M., et al., "High-frequency Transfer of Cloned Herpes Simplex Virus Type I Sequences to Mammalian Cells by Protoplast Fusion," *Molecular Cellular Biology*, vol. 1, No. 8, Aug. 1981, pp. 743-752.

Saunders, J.A., et al., "Plant Gene Transfer Using Electrofusion and Electroporation," In *Electroporation and Electrofusion in Cell Biology*. E. Neumann, A.E. Sowers, and C.A. Jordan, editors. Plenum Press, New York. 1989, pp. 343-354.

Sawyer, T.K., "Src Homology-2 Domains: Structure, Mechanisms, and Drug Discovery," *Biopolymers*, vol. 47, 1998, pp. 243-261.

Schaffner, W., "Direct Transfer of Cloned Genes from Bacteria to Mammalian Cells," *Proceedings of the National Academy of Sciences of the United States of America*, vol. 77, No. 4, Apr. 1980, pp. 2163-2167.

Scheidt, K.A., et al., "Structure-Based Design, Synthesis and Evaluation of Conformationally Constrained Cysteine Protease Inhibitors," *Bioorg Med Chem.*, vol. 6, 1998, 2477-2494.

Selden, R.F., et al., "Human Growth Hormone as a Reporter Gene in Regulation Studies Employing Transient Gene Expression,"*Molecular and Cellular Biololgy*, vol. 6, No. 9, Sep. 1986, pp. 3173-3179.

Shigekawa, K., et al., "Electroporation of Eukaryotes and Prokaryotes: A General Approach to the Introduction of Macomolecules into Cells," *BioTechniques*, vol. 6, No. 8, 1988, pp. 742-751.

Shillito, R. "Methods of genetic Transformations: Electroporation and Polyethylene Glycol Treatment," In *Molecular Improvement of Cereal Crop.* I. Vasil, editor. Kluwer, Dordrecht, The Netherlands, 1999, pp. 9-20.

Simonsen, C.C., et al., "Isolation and Expression of an Altered Mouse Dihydrofolate Reductase cDNA," *Proceedings of the National Academy of Sciences of the United States of America*, vol. 80, No. 9, May 1, 1983, pp. 2495-2499.

Smith, D.B., et al., "Single-step Purification of Polypeptides Expressed in *Escherichia coli* as Fusions with gGutathione S-transferase," *Gene*, vol. 67, 1988, pp. 31-40.

Southern, P.J., et al., "Transformation of Mammalian Cells to Antibiotic Resistance with a Bacterial Gene Under Control of the SV40 Early Region Promoter," *Journal of Molecular and Applied Genitics*, vol. 1, 1982, pp. 327-341.

Spinke, J. et al.; "Molecular Recoginition at Self-Assembled Monolayers: The Construction of Multicomponent Multilayers;" Langmuir; 1993; vol. 9; pp. 1821-1825.

Sreekrishna, K., et al., "High Level Expression of Heterologous Proteins in Methylotrophic Yeast *Pichia pastoris*," *Journal of Basic Microbiology*, vol. 28,1988, pp. 265-278.

Stowell, J., T. et al., "Mechanism-Based Inactivation of Ribonuclease A," *Journal of Organic Chemistry*, vol. 60, 1995, pp. 6930-6936.

Supplementary partial European search report (Feb. 14, 2007).

Thomas, S.M., et al., "Cellular Functions Regulated by Src Family Kinases," *Annual Review Cell Dev Biol.*, vol. 13,1997, pp. 513-609.

Thompson, J.A., et al., "Maize Transformation Utilizing Silicon Carbide Whiskers: A Review," *Euphytica*, vol. 85, 1995, pp. 75-80.

Tilburn, J., et al., "Transformation by Integration in *Aspergillus nidulans*," *Gene*, 26,1983, pp. 205-221.

Touraev, A., et al., "Plant Male Germ Line Transformation," *Plant Journal*, vol. 12, No. 4, 1997, pp. 949-956.

Turner, D.L., et al., "Lineage-Independent Determination of Cell Type in the Embryonic Mouse Retina," *Neuron*, vol. 4,Jun. 1990, pp. 833-845.

van Ommen, B., et al., "Irreversible Inhibition of Rat Glutathione S-transferase 1-1 by Quinones and Their Glutathione Conjugates. Structure-activity Relationship and Mechanism." *Biochem J.*, vol. 276, 1991, pp. 661-666.

van Ommen, B., et al., "Studies on the Active Site of Rat Glutathione S-transferase Isoenzyme 4-4. Chemical Modification by Tetrachloro-1,4- Benzoquinone and its Glutathione Conjugate," *Eur J Biochem.*, vol. 181,1989, pp. 423-429.

Violette, S.M., et al. "A Src SH2 Selective Binding Compound Inhibits Osteoclast-Mediated Resorption," *Chem Biol.*, vol. 7, 2000, pp. 225-235.

White, D., et al., "Preparation of Site-specific Antibodies to Acetylated Histones," *Methods*, vol. 19, 1999, pp. 417-424.

Wigler, M., et al., "Biochemical Transfer of Single-Copy Eucaryotic Genes Using Total Cellular DNA as Donor," *Cell*, vol. 14, Jul. 1978, pp. 725-731.

Williams, D.A., et al., "Introduction of New Genetic Material into Pluripotent Haematopoietic Stem Cells of the Mouse," *Nature*, vol. 310, Aug. 1984, pp. 476-480.

(56) References Cited

OTHER PUBLICATIONS

Wilner, L. et al.; "Mediated Electron Transfer in Glutathione Reductase Organized in Self-Assembled Monolayers on Au Electrodes;" Journal of the American Chemical Society; 1992; vol. 114; pp. 10965-10966.

Wong, T.K., et al., "Electric Field Mediated Gene Transfer," *Biochemical and Biophysical Research Communications*, vol. 107, No. 2, Jul. 30, 1982, pp. 584-587.

Wu, S.Y., et al., "Ethyl Octylphosphonofluoridate and Analogs: Optimized Inhibitors of Neuropathy Target Esterase," *Chem Res Toxicol.*, vol. 8, 1995, pp. 1070-1075.

Wyborski, D.L., et al., "Parameters Affecting the Use of the Lac Repressor System in Eukaryotic Cells and Transgenic Animals," *Environmental and Molecular Mutagenesis*, vol. 28, 1996, pp. 447-458.

Wyborski, D.L., et al., "Analysis of Inducers of the *E.coli* Lac Repressor System in Mammalian Cells and Whole Animals," *Nucleic Acids Res*, vol. 19, 1991, pp. 4647-4653.

Yelton, M.M., J.E. Hamer, and W.E. Timberlake. 1984. Transformation of *Aspergillus nidulans* by using a trpC plasmid. *Proc Natl Acad Sci U S A*. 81:1470-4.

Yousaf, Muhammad, et al., "Diels-Alder reaction for the Selective Immobilization of Protein to Electroactive Self-Assembled Monolayers," *J. Am. Chem. Soc.*, vol. 121, 1999, pp. 4286-4387.

Yousaf, M., et al., "Turning on Cell Migration with Electroactive Substrates," *Angew. Chem. Int. Ed.*, vol. 40, 2001, pp. 1093-1096.

Zhou, G., et al. "Introduction of Exogenous DNA Into Cotton Embryos," *Methods in Enzymology*, vol. 101, 1983, pp. 433-481.

\* cited by examiner

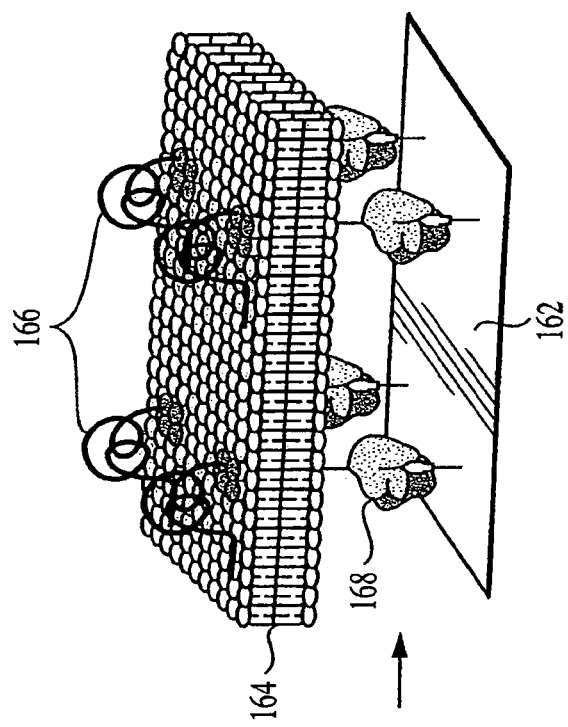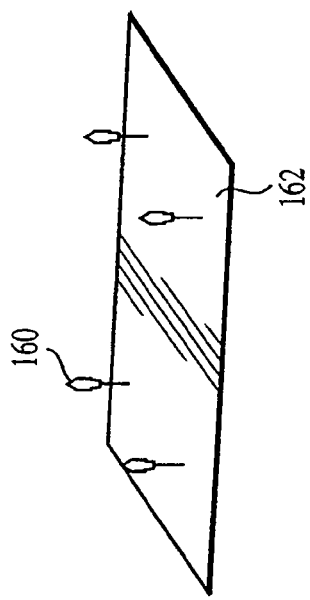
FIG. 3

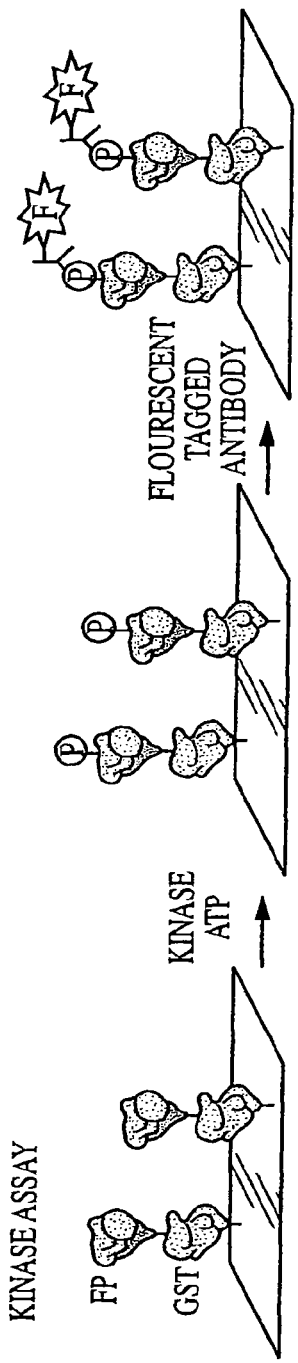
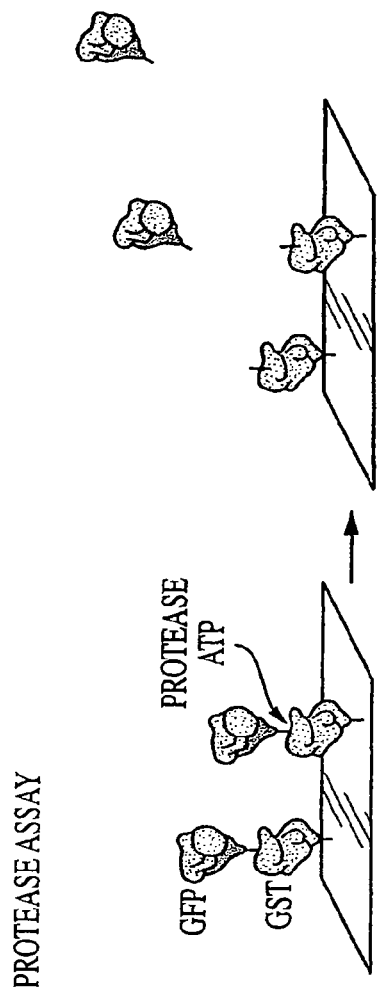

SEQUENCE LISTING

```
<160> NUMBER OF SEQ ID NOS: 5

<210> SEQ ID NO 1
<211> LENGTH: 42
<212> TYPE: DNA
<213> ORGANISM: Artificial Sequence
<220> FEATURE:
<223> OTHER INFORMATION: Primer sequence, Exon1F, for F. solani cutinase
      gene

<400> SEQUENCE: 1
gccacggcca tgggcctgcc tacttctaac cctgcccagg ag                          42

<210> SEQ ID NO 2
<211> LENGTH: 38
<212> TYPE: DNA
<213> ORGANISM: Artificial Sequence
<220> FEATURE:
<223> OTHER INFORMATION: Primer sequence, Exon1B, for F. solani cutinase
      gene

<400> SEQUENCE: 2
ccggtaccca agttgcccgt ctctgttgaa cctcgggc                               38

<210> SEQ ID NO 3
<211> LENGTH: 38
<212> TYPE: DNA
<213> ORGANISM: Artificial Sequence
<220> FEATURE:
<223> OTHER INFORMATION: Primer sequence, Exon2F, for F. solani cutinase
      gene

<400> SEQUENCE: 3
ccggtaccct cggtcctagc attgcctcca accttgag                               38

<210> SEQ ID NO 4
<211> LENGTH: 36
<212> TYPE: DNA
<213> ORGANISM: Artificial Sequence
<220> FEATURE:
<223> OTHER INFORMATION: Primer sequence, Exon2B, for F. solani cutinase
      gene
```

<400> SEQUENCE: 4
ccgggatcct caagcagaac cacggacagc ccgaac                                    36

<210> SEQ ID NO 5
<211> LENGTH: 2769
<212> TYPE: DNA
<213> ORGANISM: Fusarium solani

<400> SEQUENCE: 5
agtggaaggg gagccgtgtg gaggcacaag aagctgaaaa aaccgaggtc aaaagacctg        60
ctgaatagtt tgtcactgag atgagatggg aacggcatga aatcttgggc cttattctga       120
caccatcgcc tccttcctgg tacgccttgc atcaaaagag agggttctac cccctaaaag       180
cacagctcga atgaaattcc catttgagta gatccaacga tgctccgtgt ttctctaggt       240
tgggtaggca ggttgaccca cccatgatga gcggcagggt caggtaggtc ggtaaatatc       300
cgagccgctg atttgcggat gaacgagtcc aagcttggca tgatctgttg atctcaaaac       360
cctccaatca ccgtaaagag gcactcgtaa aagtcctccg atgcctctcc accatcaggt       420
aggtggtgtc tatgcgcgct ctgacactct tcgcaaggtg taacagaata ggcaaagcgg       480
ccttcccgag gtttcatctc taaaaccaaa ctcacgcttg tcaaagtgac agctgaacag       540
ccgatattcg ctgattgggc tcttttcatgt ttgcgggaac gttccatcta ccggtttagc       600
gatcggcacg ggttgcaact agaagcggaa gagcttgcgg ggaggggcac ggggtggttt       660
cctgaagcga ctaggttgcc tgaaactatc acgactcata gctgcgagcg catggtccag       720
tatcaagagt tttgacgtcc tttgatgaaa actgcccctc tcttgacgct agaaaccgag       780
gaaatggatc gcgagccgag gctcgatttc agagcttgga cgatgatagt ttcatctgtt       840
caagcttaaa tatcgttgtt ccagaccact gggaacggaa ccagacaacc acacatacct       900
tcacttcatc aacattcact tcaactcttc gcctcttcct tttcactctt tatcatcctc       960
accatgaaat tcttcgctct caccacactt ctcgccgcca cggcttcggc tctgcctact      1020
tctaaccctg cccaggagct tgaggcgcgc cagcttggta gaacaactcg cgacgatctg      1080
atcaacggca atagcgcttc ctgcgccgat gtcatcttca tttatgcccg aggttcaaca      1140
gagacgggca acttggttcg tagaatttct tctcatgaca acatcacttt tcttacacat      1200
ccattaggga actctcggtc ctagcattgc ctccaacctt gagtccgcct tcggcaagga      1260
cggtgtctgg attcagggcg ttggcggtgc ctacgcagcc actcttggag acaatgctct      1320
ccctcgcgga acctctagcg ccgcaatcag ggagatgctc ggtctcttcc agcaggccaa      1380
caccaagtgc cctgacgcga ctttgatcgc cggtggctac agccagggtg ctgcacttgc      1440
agccgcctcc atcgaggacc tcgactcggc cattcgtgac aagatcgccg gaactgttct      1500
gttcggctac accaagaacc tacagaaccg tggccgaatc cccaactacc ctgccgacag      1560
gaccaaggtc ttctgcaata cagggatct cgtttgtact ggtagcttga tcgttgctgc      1620
acctcacttg gcttatggtc ctgatgctcg tggccctgcc cctgagttcc tcatcgagaa      1680
ggttcgggct gtccgtggtt ctgcttgagg aggatgagaa ttttagcagg cgggcctgtt      1740
aattattgcg aggtttcaag tttttctttt ggtgaatagc catgatagat tggttcaaca      1800
ctcaatgtac tacaatggcc catagtttca aattaaagaa gcaatgaatg gtgatctaca      1860
tatcgctttg cccaagaaat cccaaccagg cttccatacc ctgagccagt tgagcacaaa      1920
tttcgtgccc tctgctgagc ttgccaggaa aggtcgatac ataaaccggc cttgacagac      1980

-continued

```
agggcgctac ctgcacgaat tggtcccgcc aggtgtgcgc tcaaggcgaa gttcgccgat    2040
ttatagacca cctctcattc ccatcatgca catctgtccc tgactcgcct tctccatcaa    2100
taacaccgag attggttaca atccaggata gctcgcgatc cctctttgct tgatctccgt    2160
gatactcctg ccaatcatgc actagcttca tcaagccaac aatgttgttt ttcaggccgg    2220
cgttcaacct ttcctcgata tccccacggg agaccttgat gcggaccata tctccctctc    2280
aagatcacgg acaggttggt tttcccagtt gttggcccgg gctgtggctc gaatatccgc    2340
aactaggtcg gagtcaaacg tatggtggat agtcgacacg cagttctgca ccttccgttg    2400
ggtctcagct gcattgcctt tttcggggta catgaatctc cgctggtcca ttgcagtaga    2460
ggcggtgaaa gcgcgggcct tcttttcagg gacgtagcaa gcctaaacat gctagcctga    2520
tgccgtgaag aagaccagtt agagtggtac catgctgacg acaggcacca agaatgcgac    2580
aaagagctgc atttggatgc taaaagaagt tgtctgggaa gcatatgacc cgagttgaag    2640
aggagcccac gtggcctttg ccgacttgga ggagagtaac gatggaccga aggtatgcca    2700
tacttgtgaa aaagcaaacc cgagagttat ggggtgtttg gccaacttct cctgaggaag    2760
agggagatc                                                            2769
```

POLYPEPTIDE IMMOBILIZATION

RELATED APPLICATIONS

The present application is a continuation of U.S. Ser. No. 11/645,095, filed Dec. 21, 2006, (now U.S. Pat. No. 7,888,055), which is a continuation of U.S. Ser. No. 09/923,760, filed Aug. 7, 2001 (now U.S. Pat. No. 7,172,905).

FEDERALLY SPONSORED RESEARCH OR DEVELOPMENT

The subject matter of this application was in part funded by the NSF (Grant nos. BES-9980850 and DMR9808595). The government may have certain rights in this invention.

BACKGROUND

The integration of biochemical assays onto solid substrates has revolutionized the analysis of biological samples, and has proven important in experimental cell biology as well as in a variety of applications including drug discovery and clinical diagnostics. The gene chip, which is based on patterned arrays of oligonucleotides, is the most developed example and enables the high-throughput analysis of gene expression. The successful implementation of the gene chip has in turn motivated the development of a range of other biochips, including cell chips and protein chips.

A protein chip, proteins immobilized in arrays on a substrate, would overcome many of the limitations of current technology used in protein analysis. An array of this type could give direct information on the interactions of proteins and the activities of enzymes, and would significantly extend the ability to characterize and understand molecular pathways within cells.

The development of functional protein chips has proven more difficult than the development of the gene chip. Proteins typically adsorb nonspecifically to the surfaces of most synthetic materials, with only a fraction properly oriented for interacting with proteins in a contacting solution. The adsorbed proteins tend to denature to varying degrees, resulting in a loss of activity. Also, adsorbed proteins can be displaced by other proteins in a contacting solution, leading to a loss of activity on the chip and an unacceptable level of background signal.

To avoid this problematic displacement during use, proteins can be immobilized onto solid supports by simple chemical reactions, including the condensation of amines with carboxylic acids and the formation of disulfides.

This covalent immobilization of proteins on inert substrates can prevent high background signals due to non-specific adsorption. Proteins immobilized by this approach are still subject to denaturation, however. The chemical coupling approach is also typically limited by a lack of selectivity.

Many natural proteins have been prepared using recombinant techniques, as fusions of the natural protein and another polypeptide. The polypeptide is used as a handle for purification, followed by cleavage of the polypeptide from the fusion. For example, a protein can be expressed with a pendant chain of six histidine units. These His-tag proteins can coordinate with Ni(II) complexes, so that they can be immobilized on a surface and purified from other cell constituents. Fusions of proteins with glutathione-S-transferase (GST), an enzyme, have also been used; GST-fusion polypeptides may be applied to sepharose columns modified with glutathione peptides, to purify the proteins. These methods are effective because the fusion polypeptide binds selectively to the ligands of the column. These interactions cannot be used to assemble protein chips because the binding affinities of the fusion polypeptides for the ligands are low and would lead to a loss of protein from the substrate.

There is a thus a need for biochemical strategies that can selectively immobilize proteins to a surface with absolute control over orientation and density while maintaining the activity of the protein. Rapid and irreversible immobilization techniques would provide convenient production of the modified surfaces while ensuring their long-term stability. It is especially desirable that these strategies not require synthetic modification or purification of the proteins prior to immobilization, and further that the strategies can be used for most proteins of interest.

BRIEF SUMMARY

In a first aspect, the present invention provides an alkanethiol of formula (I):

$$\text{HS-L-Q-T} \qquad (I).$$

The moiety -L- is $-(A_x-B_y-E_z-D)_w-$; each A, B, E and D are individually $C(R_A R_A')-$, $-C(R_B R_B')-$, $-C(R_E R_E')-$, and $-C(R_D R_D')-$, respectively; each $R_A$, $R_B$, $R_E$ and $R_D$ is selected from the group consisting of H, alkyl, alkenyl, alkynyl, aryl and heterocyclic radical, or any two of $R_A$, $R_B$, $R_E$ and $R_D$ together form a bond, or any two of $R_A$, $R_B$, $R_E$ and $R_D$ together with the atoms to which they are bonded form a ring; each $R_A'$, $R_B'$, $R_E'$ and $R_D'$ is selected from the group consisting of H, alkyl, alkenyl, alkynyl, aryl and heterocyclic radical, or any two of $R_A'$, $R_B'$, $R_E'$ and $R_D'$ together form a bond, or any two $R_A'$, $R_B'$, $R_E'$ and $R_D'$ together with the atoms to which they are bonded form a ring; each x, y and z are individually either 0 or 1; and w is 1 to 5. The moiety -Q- is selected from the group consisting of

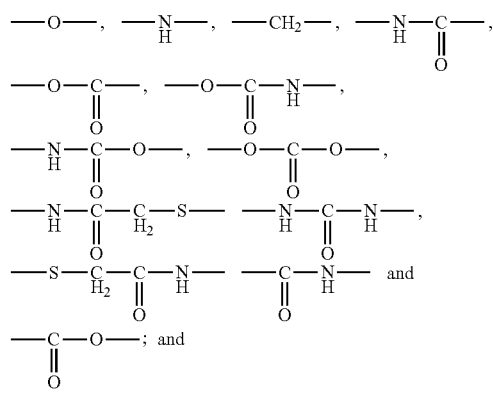

the moiety -T comprises a reactant ligand.

In a second aspect, the present invention provides a disulfide of formula (V):

$$\text{J-S—S-L-Q-T} \qquad (V).$$

The moiety -L- is $-(A_x-B_y-E_z-D)_w-$; each A, B, E and D are individually $C(R_A R_A')-$, $-C(R_B R_B')-$, $-C(R_E R_E')-$, and $-C(R_D R_D')-$, respectively; each $R_A$, $R_B$, $R_E$ and $R_D$ is selected from the group consisting of H, alkyl, alkenyl, alkynyl, aryl and heterocyclic radical, or any two of $R_A$, $R_B$, $R_E$ and $R_D$ together form a bond, or any two of $R_A$, $R_B$, $R_E$ and $R_D$ together with the atoms to which they are bonded form a ring; each $R_A'$, $R_B'$, $R_E'$ and $R_D'$ is selected from the group consisting of H, alkyl, alkenyl, alkynyl, aryl and heterocyclic radical, or any two of $R_A'$, $R_B'$, $R_E'$ and $R_D'$ together form a bond, or any two $R_A'$, $R_B'$, $R_E'$ and $R_D'$ together with the atoms to which they are bonded form a ring; each x, y and z are individually either 0 or 1; and w is 1 to 5. The moiety -Q- is selected from the group consisting of

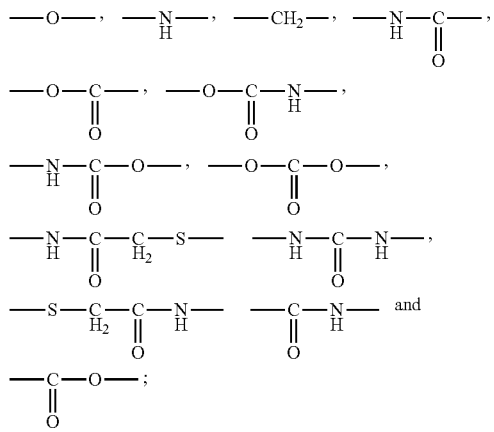

the moiety -T comprises a reactant ligand; and the moiety -J is selected from the group consisting of H, halogen, R, —OR, —NRR', —C(O)R, and —C(O)OR; R is selected from the group consisting of alkyl, alkenyl, alkynyl, aryl and heterocyclic radical; and R' is selected from the group consisting of H, alkyl, alkenyl, alkynyl, aryl and heterocyclic radical. The disulfide does not selectively bind avidin or streptavidin.

In a third aspect, the present invention provides a substrate, comprising a surface comprising gold, and a plurality of moieties, on at least a portion of said surface. The moieties are alkanethiolate moieties of formula (VII):

Surf-S-L-Q-T        (VII).

The moiety -L- is $-(A_x-B_y-E_z-D)_w-$; each A, B, E and D are individually $C(R_AR_A')—$, $—C(R_BR_B')—$, $—C(R_ER_E')—$, and $—C(R_DR_D')—$, respectively; each $R_A$, $R_B$, $R_E$ and $R_D$ is selected from the group consisting of H, alkyl, alkenyl, alkynyl, aryl and heterocyclic radical, or any two of $R_A$, $R_B$, $R_E$ and $R_D$ together form a bond, or any two of $R_A$, $R_B$, $R_E$ and $R_D$ together with the atoms to which they are bonded form a ring; each $R_A'$, $R_B'$, $R_E'$ and $R_D'$ is selected from the group consisting of H, alkyl, alkenyl, alkynyl, aryl and heterocyclic radical, or any two of $R_A'$, $R_B'$, $R_E'$ and $R_D'$ together form a bond, or any two $R_A'$, $R_B'$, $R_E'$ and $R_D'$ together with the atoms to which they are bonded form a ring; each x, y and z are individually either 0 or 1; and w is 1 to 5. The moiety -Q- is selected from the group consisting of

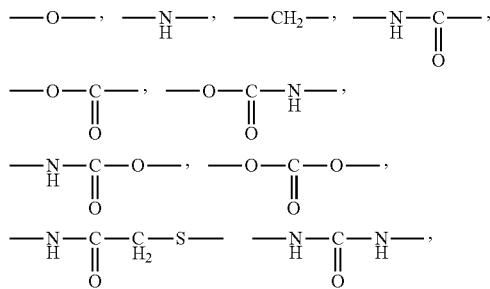

the moiety -T comprises a reactant ligand; and Surf designates where the moiety attaches to said surface.

In a fourth aspect, the present invention provides a substrate, comprising a plurality of reactant ligands, attached to said substrate.

In a fifth aspect, the present invention provides a substrate, comprising a surface, and a plurality of moieties, on at least a portion of said surface. The moieties are moieties of formula (VIII):

Surf-L-Q-T        (VIII).

The moiety -L- is $-(A_x-B_y-E_z-D)_w-$; each A, B, E and D are individually $C(R_AR_A')—$, $—C(R_BR_B')—$, $—C(R_ER_E')—$, and $—C(R_DR_D')—$, respectively; each $R_A$, $R_B$, $R_E$ and $R_D$ is selected from the group consisting of H, alkyl, alkenyl, alkynyl, aryl and heterocyclic radical, or any two of $R_A$, $R_B$, $R_E$ and $R_D$ together form a bond, or any two of $R_A$, $R_B$, $R_E$ and $R_D$ together with the atoms to which they are bonded form a ring; each $R_A'$, $R_B'$, $R_E'$ and $R_D'$ is selected from the group consisting of H, alkyl, alkenyl, alkynyl, aryl and heterocyclic radical, or any two of $R_A'$, $R_B'$, $R_E'$ and $R_D'$ together form a bond, or any two $R_A'$, $R_B'$, $R_E'$ and $R_D'$ together with the atoms to which they are bonded form a ring; each x, y and z are individually either 0 or 1; and w is 1 to 5. The moiety -Q- is selected from the group consisting of

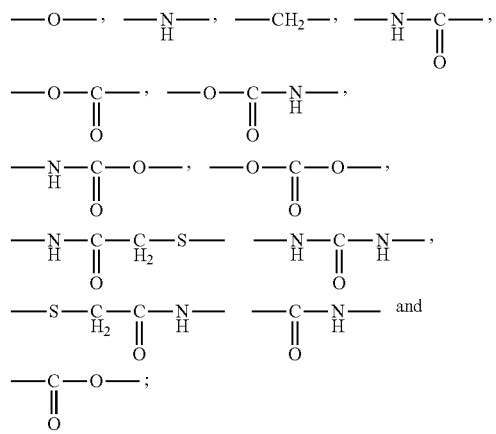

the moiety -T comprises a reactant ligand; and Surf designates where the moiety attaches to said surface.

In a sixth aspect, the present invention provides a protein chip, comprising a substrate; and the reaction product of a reactant ligand and a fusion polypeptide, on said substrate. The fusion polypeptide comprises the corresponding capture polypeptide moiety.

In a seventh aspect, the present invention provides a method of making a substrate, comprising contacting a surface with any of the above alkanethiols or disulfides. The surface comprises gold.

In an eighth aspect, the present invention provides a method of making a protein chip, comprising contacting any of the above substrates with a fusion polypeptide.

In a ninth aspect, the present invention provides a fusion of a capture poloypeptide and a display moiety. The fusion display polypeptide moiety does not consist of GST, His tag, lacZ, trpE, maltose binding protein, thioredoxin, or $F_c$ region of an immunoglobulin, and a corresponding reactant ligand of the capture polypeptide is a moiety of formula (III):

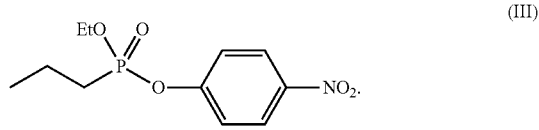

(III)

In a tenth aspect, the present invention provides a method of immobilizing a fusion, comprising reacting a fusion with a reactant ligand. The reactant ligand is attached to a surface.

In an eleventh aspect, the present invention provides a method of attaching a display moiety on a surface, comprising reacting a capture polypeptide moiety with a corresponding reactant ligand to form a covalent bond. The capture polypeptide moiety is a fusion with the display moiety, and the reactant ligand is attached to the surface.

In a twelfth aspect, the present invention provides a method of attaching a polypeptide to a surface, comprising non-covalently attaching a polypeptide to a reactant ligand specific to the polypeptide; followed by forming a covalent bond between the polypeptide and the reactant ligand.

DEFINITIONS

"Alkyl" (or alkyl- or alk-) refers to a substituted or unsubstituted, straight, branched or cyclic hydrocarbon chain, preferably containing from 1 to 20 carbon atoms. More preferred alkyl groups are alkyl groups containing from 7 to 16 carbon atoms. Preferred cycloalkyls have from 3 to 10, preferably 3-6, carbon atoms in their ring structure. Suitable examples of unsubstituted alkyl groups include methyl, ethyl, propyl, isopropyl, cyclopropyl, butyl, iso-butyl, tert-butyl, sec-butyl, cyclobutyl, pentyl, cyclopentyl, hexyl, cyclohexyl, and the like. "Alkylaryl" and "alkylheterocyclic" groups are alkyl groups covalently bonded to an aryl or heterocyclic group, respectively.

"Alkenyl" refers to a substituted or unsubstituted, straight, branched or cyclic, unsaturated hydrocarbon that contains at least one double bond, and preferably 2 to 20, more preferably 7 to 16, carbon atoms. Exemplary unsubstituted alkenyl groups include ethenyl (or vinyl)(—CH=CH$_2$), 1-propenyl, 2-propenyl (or allyl)(—CH$_2$—CH=CH$_2$), 1,3-butadienyl (—CH=CHCH=CH$_2$), 1-butenyl (—CH=CHCH$_2$CH$_3$), hexenyl, pentenyl, 1,3,5-hexatrienyl, and the like. Preferred cycloalkenyl groups contain five to eight carbon atoms and at least one double bond. Examples of cycloalkenyl groups include cyclohexadienyl, cyclohexenyl, cyclopentenyl, cycloheptenyl, cyclooctenyl, cyclohexadienyl, cycloheptadienyl, cyclooctatrienyl and the like.

"Alkynyl" refers to a substituted or unsubstituted, straight, branched or cyclic unsaturated hydrocarbon containing at least one triple bond, and preferably 2 to 20, more preferably 7 to 16, carbon atoms.

"Aryl" refers to any monovalent aromatic carbocyclic or heteroaromatic group, preferably of 3 to 10 carbon atoms. The aryl group can be monocyclic (e.g., phenyl (or Ph)) or polycyclic (e.g., naphthyl) and can be unsubstituted or substituted. Preferred aryl groups include phenyl, naphthyl, furyl, thienyl, pyridyl, indolyl, quinolinyl or isoquinolinyl.

"Halogen" (or halo-) refers to fluorine, chlorine, iodine or bromine. The preferred halogen is fluorine or chlorine.

"Heterocyclic radical" refers to a stable, saturated, partially unsaturated, or aromatic ring, preferably containing 5 to 10, more preferably 5 to 6, atoms. The ring can be substituted 1 or more times (preferably 1, 2, 3, 4 or 5 times) with a substituent. The ring can be mono-, bi- or polycyclic. The heterocyclic group consists of carbon atoms and from 1 to 3 heteroatoms independently selected from the group consisting of nitrogen, oxygen, and sulfur. The heteroatoms can be protected or unprotected. Examples of useful heterocyclic groups include substituted or unsubstituted, protected or unprotected acridine, benzathiazoline, benzimidazole, benzofuran, benzothiophene, benzothiazole, benzothiophenyl, carbazole, cinnoline, furan, imidazole, 1H-indazole, indole, isoindole, isoquinoline, isothiazole, morpholine, oxazole (i.e. 1,2,3-oxadiazole), phenazine, phenothiazine, phenoxazine, phthalazine, piperazine, pteridine, purine, pyrazine, pyrazole, pyridazine, pyridine, pyrimidine, pyrrole, quinazoline, quinoline, quinoxaline, thiazole, 1,3,4-thiadiazole, thiophene, 1,3,5-triazines, triazole (i.e. 1,2,3-triazole), and the like.

"Substituted" means that the moiety contains at least one, preferably 1-3, substituent(s). Suitable substituents include hydroxyl (—OH), amino (—NH$_2$), oxy (—O—), carbonyl (—CO—), thiol, alkyl, alkenyl, alkynyl, alkoxy, halo, nitrile, nitro, aryl and heterocyclic groups. These substituents can optionally be further substituted with 1-3 substituents. Examples of substituted substituents include carboxamide, alkylmercapto, alkylsulphonyl, alkylamino, dialkylamino, carboxylate, alkoxycarbonyl, alkylaryl, aralkyl, alkylheterocyclic, and the like.

"Disulfide" means a compound containing at least one sulfur-sulfur bond.

"Alkanethiol" means a compound containing an alkyl group bonded to an SH group.

"Alkanethiolate" means a moiety corresponding to an alkanethiol without the hydrogen of the SH group.

"Alkylene" refers to a substituted or unsubstituted, straight, branched or cyclic hydrocarbon chain, preferably containing from 1 to 20 carbon atoms. More preferred alkylene groups are lower alkylene groups, i.e., alkylene groups containing from 1 to 6 carbon atoms. Preferred cycloalkylenes have from 3 to 10, preferably from 3 to 6, carbon atoms in their ring structure. Suitable examples of unsubstituted alkylene groups include methylene, —(CH$_2$)$_n$—, —CH$_2$—CH(CH$_3$)—, —(C$_6$H$_{10}$)— where the carbon atoms form a six-membered ring, and the like.

"Polypeptide" refers to a molecule or moiety containing two or more amino acids bound through a peptide linkage. Examples include proteins such as antibodies, enzymes, lectins and receptors; lipoproteins and lipopolypeptides; and glycoproteins and glycopolypeptides.

"Polynucleotide" refers to a molecule or moiety containing two or more nucleic acids such as single or double stranded RNA, DNA and PNA (protein nucleic acid).

"Carbohydrate" refers to a molecule or moiety that contains one or more sugars, such as mannose, sucrose, glucose, cellulose, chitin, and chitosan.

"Ligand" refers to a molecule or moiety which binds a specific site on a polypeptide or other molecule.

"Receptor" refers to a polypeptide that binds (or ligates) a specific molecule (ligand) and, when expressed in a cell, may initiate a response in the cell. Receptors may specifically bind ligands without a signaling response.

"Hapten" refers to a molecule or moiety that is incapable, alone, of being antigenic but can combine with an antigenic molecule, or carrier. A hapten-carrier complex can stimulate antibody production, and some of these antibodies will bind specifically to the hapten. Examples include fluorescein, and the phosphate of phosphotyrosine.

"Fusion" refers to a molecule comprising a capture polypeptide and a display moiety.

"Capture polypeptide" refers to a polypeptide, present as a fusion with the display moiety, which reacts specifically with a corresponding reactant ligand, and which forms a covalent bond with the reactant ligand.

"Display moiety" refers to a polypeptide or polynucleotide. Preferably, the display moiety is a polypeptide having the amino acid sequence of a natural protein, and retains the biological activity of the natural protein.

"Reactant ligand" refers to a moiety that reacts specifically with a class of corresponding capture polypeptides, forming a covalent bond. Preferably, a reactant ligand reacts specifically with only one corresponding capture polypeptide.

"Non-covalent attachment" refers to a chemical interaction that is not a covalent bond, including hydrophobic/hydrophilic interactions, Hydrogen-bonding, van der Waals interactions, and ionic interactions.

"Affinity" refers to the product of the concentration of the free ligand and the concentration of the free receptor, divided by the concentration of the ligand/receptor complex.

All other acronyms and abbreviations have the corresponding meaning as published in journals related to the arts of chemistry and biology.

BRIEF DESCRIPTION OF THE DRAWINGS

FIG. 3 illustrates a general strategy for confining membrane associated proteins to monolayers by way of GST immobilization.

FIG. 6 illustrates a kinase assay.

FIG. 7 illustrates a protease assay.

DETAILED DESCRIPTION

In one embodiment, the invention includes a fusion immobilized on a surface. The fusion includes a display moiety and a capture polypeptide, attached to the surface through the reaction product of a reactant ligand with the capture polypeptide. This strategy permits the selective and covalent immobilization of display moieties while avoiding both non-specific adsorption and, in the case of display polypeptides, protein denaturation. The immobilized display moieties retain their native conformation, and/or biochemical properties of interest, such as physiological functions, specificity and selectivity for small molecule, polypeptide, and polynucleotide partners and/or immunological properties.

Reactant Ligands and Capture Polypeptides

Figure 1A:
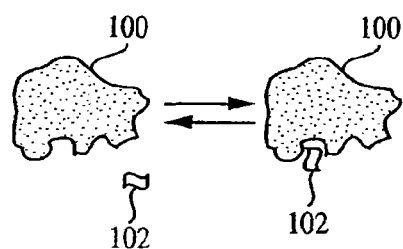
FIGS. 1A-1C illustrate a method for immobilizing a protein on a surface.
Figure 1B:
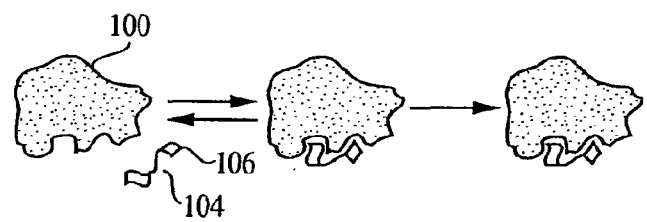
Figure 1C:
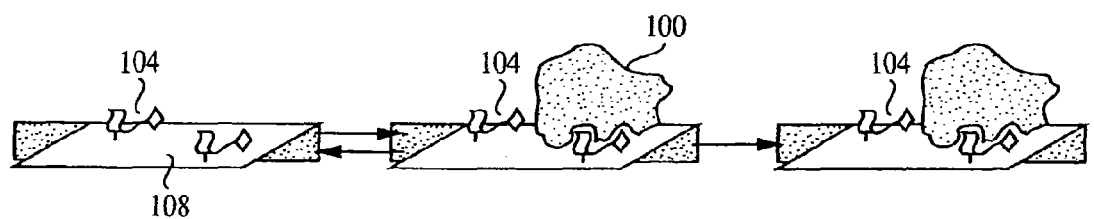

A fusion can be selectively immobilized on a surface by the formation of a covalent bond between the fusion and a corresponding reactant ligand. The fusion contains a display moiety, which is the moiety of interest to be immobilized, and a capture polypeptide, which interacts with the corresponding reactant ligand to form a covalent bond. Referring to FIG. 1A, each capture polypeptide 100 has associated with it a ligand 102 that selectively binds that polypeptide. The ligand may be converted into a reactant ligand 104 by modification with a reactive group 106 so that it covalently binds to the capture polypeptide (FIG. 1B). The reactive group 106 is defined as a chemical moiety which reacts with the capture polypeptide or which becomes reactive upon binding to the capture polypeptide. The reaction of the reactive group with the polypeptide results in the formation of a covalent bond. This reactant ligand 104 can then be incorporated onto an inert substrate 108, where it serves to mediate the selective immobilization of the capture polypeptide (FIG. 1C).

A reactant ligand is a ligand which binds a polypeptide and forms a covalent bond between the ligand and the polypeptide. The covalent bond provides stability to the bound reactant ligand-polypeptide complex such that the polypeptide and/or its derivatives can be analyzed. A non-covalent attachment, such as the binding interaction of the polypeptide and the reactant ligand, is an interaction that is not a covalent bond. Examples of non-covalent attachments include hydrophobic/hydrophilic interactions, Hydrogen-bonding, van der Waals interactions, metal chelation/coordination, and ionic interactions.

The covalent bond between the reactant ligand and the capture polypeptide is characterized by a stability which is expressed in terms of half-life. For a first-order dissociation process, the half-life is equal to the natural logarithm of the number 2, divided by the dissociation rate constant. Preferably, the half-life of the covalent bond at physiological pH and temperature is at least 3 minutes. More preferably the half-life is at least 30 minutes. Even more preferably, the half-life is at least 1 hour. Even more preferably, the half-life is at least 24 hours.

Reactant ligands have been identified for a number of different polypeptides. A particular polypeptide and its corresponding reactant ligand are referred to as a reactant ligand-polypeptide pair. Preferably, the reactant ligand is specific to one polypeptide in that it binds to that particular polypeptide but not to other polypeptides. Many of the reactant ligands which have been developed are potent inhibitors of enzymes. The reactant ligand may be a mechanism-based inhibitor of a corresponding enzyme. A mechanism-based inhibitor is a substance which is relatively unreactive until it reacts with its corresponding enzyme.

Any reactant ligand-polypeptide pair may be used in the present invention. If the polypeptide is an enzyme, the reactant ligand and polypeptide binding may be characterized by an inhibition constant, $K_i$, which is the product of the concentration of free enzyme and the concentration of the free ligand, divided by the concentration of the bound enzyme-ligand complex. A smaller value of $K_i$ corresponds to a stronger inhibition constant. Preferably, $K_i$ is from 1 femtomolar (fM) to 500 millimolar (mM). More preferably, $K_i$ is from 1 picomolar (pM) to 100 mM. Even more preferably, K is from 1 pM to 1 mM. The rate constant of the inhibition is preferably from $0.0001\ s^{-1}$ to $60\ s^{-1}$. More preferably, the rate constant is from 0.01 s$^{-1}$ to 10 s$^{-1}$. A strong inhibition constant is desirable because it allows the use of a relatively small amount of fusion to be used for immobilization. For an immobilized reactant ligand, the half-life of its inhibition reaction with a polypeptide which is present at a concentration of 0.1 mM is preferably from 0.01 second to 8 hours. More preferably, the half life is from 0.01 second to 30 minutes.

Examples of useful reactant ligand/polypeptide pairs are given in Table A:

TABLE A

| Useful reactant ligand/capture polypeptide pairs | | | |
|---|---|---|---|
| Capture Polypeptide | Origin | Reactant Ligand | Reference |
| glutathione-S-transferase (GST) | | complexes of glutathione and benzoquinone | (van Ommen et al., 1991) |
| Cutinase | | Nitrophenyl-phosphonates | (Deussen et al., 2000b; Martinez et al., 1994) |
| Carboxylesterases (i.e. carboxylesterase I, II, and III) | *Pseudomanase fluorescens* | Phenyl methyl-sulfonylfluoride | (Kim et al., 1994) |
| Lipases (i.e. LIPOLASE ™; NOVO NORDISK, DK-2880 Bagsvaerd, Denmark) | *Humicola lanuginose* | Nitrophenyl-phosphonates | (Deussen et al., 2000a; Deussen et al., 2000b) |
| Acetyl-cholinesterase | *Homo sapiens* | Pyrenebutyl-methylphosphono-fluoridate | (Berman and Taylor, 1978) |
| src. SH2 domain | Mammalian | See formulas (1), (2), and (3) | (Alligood et al., 1998; Violette et al., 2000) |
| Phosphatases | mammalian; bacterial | Fluoroaryl phosphates | (Myers et al., 1997) |
| Ribonuclease A | *E. coli* | Uracil fluoroaryl phosphates | (Stowell et al., 1995) |
| His-tag | | quinone-NTA conjugate | |
| Cystein proteases (i.e. cruzain, papain, cathepsin B) | | See formulas (4) and (5) | (Scheidt et al., 1998) |

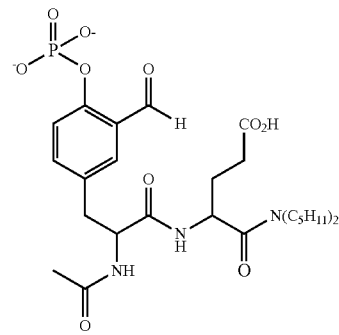

(1)

TABLE A-continued

| Useful reactant ligand/capture polypeptide pairs | | | |
|---|---|---|---|
| Capture Polypeptide | Origin | Reactant Ligand | Reference |

(2)

(3)

(4)

(5)

Fusions

The capture polypeptide, which is part of the reactant ligand-polypeptide pair, is present as a fusion of the capture polypeptide and the display moiety. For example, the fusion may contain the capture polypeptide and a display moiety that is a different polypeptide. In this case, the display polypeptide is the polypeptide of interest to be immobilized. Polypeptides may be linked to each other in a variety of ways, such as by recombinant techniques and by native chemical ligation (Kent et al., U.S. Pat. No. 6,184,344B1, 2001). As a further example, the fusion may contain the capture polypeptide and a display moiety that is a polynucleotide. In this case, the display polynucleotide is the polynucleotide of interest to be immobilized. Polynucleotides may be linked to capture polypeptides, for example, by fusion facilitated by puromycin (Gold et al., U.S. Pat. No. 6,194,550B1, 2001; Lohse et al., WO 01/04265; Szostak et al., U.S. Pat. No. 6,214,553 B1, 2001; Szostak et al., U.S. Pat. No. 6,207,446B1, 2001).

The capture polypeptide may also be a modified polypeptide or a synthetic polypeptide. That is, the capture polypeptide may be designed to bind with and form a covalent bond to a specific ligand, even if the ligand itself has not been modified. The ligand in this example is still a reactant ligand since it forms a covalent bond with the capture polypeptide. Also, both the capture polypeptide and the reactant ligand may modified with reactive groups to allow for or to enhance the covalent bond formation.

Fusion Polypeptides

The capture polypeptide may be linked to a display polypeptide as a fusion polypeptide of the capture polypeptide and the display polypeptide. Fusion polypeptides have been used in expression studies, cell-localization, bioassays, and polypeptide purification. A "chimeric polypeptide" or "fusion polypeptide" comprises a primary polypeptide fused to a secondary polypeptide. The secondary polypeptide is not substantially homologous to the primary polypeptide. A fusion polypeptide may include any portion up to, and including, the entire primary polypeptide, including any number of the biologically active portions. Such fusions have been used to facilitate the purification of recombinant polypeptides. In certain host cells, (e.g. mammalian), heterologous signal sequence fusions have been used to ameliorate primary polypeptide expression and/or secretion. Additional exemplary known fusion polypeptides are presented in Table B.

TABLE B

Exemplary polypeptides for use in fusions

| Polypeptide | In vitro analysis | In vivo analysis | Notes | Reference |
|---|---|---|---|---|
| Human growth hormone (hGH) | Radioimmuno-assay | None | Expensive, insensitive, narrow linear range. | (Selden et al., 1986) |
| β-glucuronidase (GUS) | Colorimetric, fluorescent, or chemi-luminescent | colorimetric (histo-chemical staining with X-gluc) | sensitive, broad linear range, non-iostopic. | (Gallagher, 1992) |
| Green fluorescent protein (GFP) and related molecules (RFP, BFP, YFP, etc.) | Fluorescent | fluorescent | can be used in live cells; resists photo-bleaching | (Chalfie et al., 1994) |
| Luciferase (firefly) | bioluminsecent | Bio-luminescent | protein is unstable, difficult to reproduce, signal is brief | (de Wet et al., 1987) |
| Chloramphenicol-acetyltransferase (CAT) | Chromatography, differential extraction, fluorescent, or immunoassay | None | Expensive radioactive substrates, time-consuming, insensitive, narrow linear range | (Gorman et al., 1982) |
| β-galactosidase | colorimetric, fluorescence, chemi-luminscence | colorimetric (histochemical staining with X-gal), bio-luminescent in live cells | sensitive, broad linear range; some cells have high endogenous activity | (Alam and Cook, 1990) |
| Secreted alkaline phosphatase (SEAP) | colorimetric, bioluminescent, chemi-luminescent | None | Chemiluminscence assay is sensitive and broad linear range; some cells have endogenouse alkaline phosphatase activity | (Berger et al., 1988) |
| Tat from HIV | Mediates delivery into cytoplasm and nuclei | Mediates delivery into cytoplasm and nuclei | Exploits amino acid residues of HIV tat protein. | (Frankel et al., U.S. Pat. No. 5,804,604, 1998) |

Recombinant Methods for Making Fusion Polypeptides

Fusion polypeptides can be easily created using recombinant methods: A nucleic acid encoding a particular polypeptide can be fused in-frame with a non-encoding nucleic acid, to the polypeptide $NH_2$— or COO— terminus, or internally. Fusion genes may also be synthesized by conventional techniques, including automated DNA synthesizers. PCR amplification using anchor primers that give rise to complementary overhangs between two consecutive gene fragments that can subsequently be annealed and reamplified to generate a chimeric gene sequence (Ausubel et al., 1987) is also useful. Many vectors are commercially available that facilitate subcloning display polypeptide in-frame to a fusion moiety.

Vectors are tools used to shuttle DNA between host cells or as a means to express a nucleotide sequence. Some vectors function only in prokaryotes, while others function in both prokaryotes and eukaryotes, enabling large-scale DNA preparation from prokaryotes for expression in eukaryotes. Inserting the DNA of interest, such as a nucleotide sequence or a fragment, into a vector is accomplished by ligation techniques and/or mating protocols well known to the skilled artisan. Such DNA is inserted such that its integration does not disrupt any necessary components of the vector. In the case of vectors that are used to express the inserted DNA protein, the introduced DNA is operably-linked to the vector elements that govern its transcription and translation.

Vectors can be divided into two general classes: Cloning vectors are replicating plasmid or phage with regions that are non-essential for propagation in an appropriate host cell, and into which foreign DNA can be inserted; the foreign DNA is replicated and propagated as if it were a component of the vector. An expression vector (such as a plasmid, yeast, or animal virus genome) is used to introduce foreign genetic material into a host cell or tissue in order to transcribe and translate the foreign DNA. In expression vectors, the introduced DNA is operably-linked to elements, such as promoters, that signal to the host cell to transcribe the inserted DNA. Some promoters are exceptionally useful, such as inducible promoters that control gene transcription in response to specific factors. Operably-linking a particular nucleotide sequence or anti-sense construct to an inducible promoter can control the expression of the nucleotide sequence, or fragments, or anti-sense constructs. Examples of classic inducible promoters include those that are responsive to α-interferon, heat-shock, heavy metal ions, steroids such as glucocorticoids (Kaufman, 1990), and tetracycline. Other desirable inducible promoters include those that are not endogenous to the cells in which the construct is being introduced, but, however, are responsive in those cells when the induction agent is exogenously supplied.

Vectors have many different manifestations. A "plasmid" is a circular double stranded DNA molecule into which additional DNA segments can be introduced. Viral vectors can accept additional DNA segments into the viral genome. Certain vectors are capable of autonomous replication in a host cell (e.g., episomal mammalian vectors or bacterial vectors having a bacterial origin of replication). Other vectors (e.g., non-episomal mammalian vectors) are integrated into the genome of a host cell upon introduction into the host cell, and thereby are replicated along with the host genome. In general, useful expression vectors are often plasmids. However, other forms of expression vectors, such as viral vectors (e.g., replication defective retroviruses, adenoviruses and adeno-associated viruses) are contemplated.

Recombinant expression vectors that comprise a particular nucleotide sequence (or fragments) regulate transcription of the polypeptide by exploiting one or more host cell-responsive (or that can be manipulated in vitro) regulatory sequences that is operably-linked to the nucleotide sequence. "Operably-linked" indicates that a nucleotide sequence of interest is linked to regulatory sequences such that expression of the nucleotide sequence is achieved.

Vectors can be introduced in a variety of organisms and/or cells (Table C). Alternatively, the vectors can be transcribed and translated in vitro, for example using T7 promoter regulatory sequences and T7 polymerase.

TABLE C

Examples of hosts for cloning or expression

| Organisms | Examples | Sources and References* |
|---|---|---|
| Prokaryotes Enterobacteriaceae | *E. coli* | |
| | K 12 strain MM294 | ATCC 31,446 |
| | X1776 | ATCC 31,537 |
| | W3110 | ATCC 27,325 |
| | K5 772 | ATCC 53,635 |
| | *Enterobacter* | |
| | *Erwinia* | |
| | *Klebsiella* | |
| | *Proteus* | |
| | *Salmonella* (*S. tyhpimurium*) | |
| | *Serratia* (*S. marcescans*) | |
| | *Shigella* | |
| | *Bacilli* (*B. subtilis* and *B. licheniformis*) | |
| | *Pseudomonas* (*P. aeruginosa*) | |
| | *Streptomyces* | |
| Eukaryotes Yeasts | *Saccharomyces cerevisiae* | |
| | *Schizosaccharomyces pombe* | |
| | *Kluyveromyces* | (Fleer et al., 1991) |
| | *K. lactis* MW98-8C, CBS683, CBS4574 | (de Louvencourt et al., 1983) |
| | *K. fragilis* | ATCC 12,424 |
| | *K. bulgaricus* | ATCC 16,045 |
| | *K. wickeramii* | ATCC 24,178 |
| | *K. waltii* | ATCC 56,500 |
| | *K. drosophilarum* | ATCC 36,906 |
| | *K. thermotolerans* | |
| | *K. marxianus; yarrowia* | (EPO 402226, 1990) |
| | *Pichia pastoris* | (Sreekrishna et al., 1988) |
| | *Candida* | |
| | *Trichoderma reesia* | |
| | *Neurospora crassa* | (Case et al., 1979) |
| | *Torulopsis* | |
| | *Rhodotorula* | |
| | *Schwanniomyces* (*S. occidentalis*) | |
| Filamentous Fungi | *Neurospora* | |
| | *Penicillium* | |
| | *Tolypocladium* | (WO 91/00357, 1991) |
| | *Aspergillus* (*A. nidulans* and *A. niger*) | (Kelly and Hynes, 1985; Tilburn et al., 1983; Yelton et al., 1984) |
| Invertebrate cells | *Drosophila* S2 | |
| | *Spodoptera* Sf9 | |
| Vertebrate cells | Chinese Hamster Ovary (CHO) | |
| | simian COS | ATCC CRL 1651 |
| | COS-7 | |
| | HEK 293 | |

*Unreferenced cells are generally available from American Type Culture Collection (Manassas, VA).

Vector choice is dictated by the organism or cells being used and the desired fate of the vector. Vectors may replicate once in the target cells, or may be "suicide" vectors. In general, vectors comprise signal sequences, origins of replication, marker genes, enhancer elements, promoters, and transcription termination sequences. The choice of these elements depends on the organisms in which the vector will be used and are easily determined. Some of these elements may be conditional, such as an inducible or conditional promoter that is turned "on" when conditions are appropriate. Examples of inducible promoters include those that are tissue-specific, which relegate expression to certain cell types, steroid-responsive, or heat-shock reactive. Some bacterial repression systems, such as the lac operon, have been exploited in mammalian cells and transgenic animals (Fleck et al., 1992; Wyborski et al., 1996; Wyborski and Short, 1991). Vectors often use a selectable marker to facilitate identifying those cells that have incorporated the vector. Many selectable markers are well known in the art for the use with prokaryotes. These are usually antibiotic-resistance genes or the use of autotrophy and auxotrophy mutants.

The terms "host cell" and "recombinant host cell" are used interchangeably. Such terms refer not only to a particular subject cell but also to the progeny or potential progeny of such a cell. Because certain modifications may occur in succeeding generations due to either mutation or environmental influences, such progeny may not, in fact, be identical to the parent cell, but are still included within the scope of the term.

Methods of eukaryotic cell transfection and prokaryotic cell transformation are well known in the art. The choice of host cell will dictate the preferred technique for introducing the nucleic acid of interest. Table D, which is not meant to be limiting, summarizes many of the known techniques in the art. Introduction of nucleic acids into an organism may also be done with ex vivo techniques that use an in vitro method of transfection, as well as established genetic techniques, if any, for that particular organism.

TABLE D

Methods to introduce nucleic acid into cells

| Cells | Methods | References | Notes |
|---|---|---|---|
| Prokaryotes (bacteria) | Calcium chloride | (Cohen et al., 1972; Hanahan, 1983; Mandel and Higa, 1970) | |
| | Electroporation | (Shigekawa and Dower, 1988) | |
| Eukaryotes Mammalian cells | Calcium phosphate transfection | N-(2-Hydroxyethyl)piperazine-N'-(2-ethanesulfonic acid (HEPES) buffered saline solution (Chen and Okayama, 1988; Graham and van der Eb, 1973; Wigler et al., 1978) BES (N,N-bis(2-hydroxyethyl)-2-aminoethanesulfonic acid) buffered solution (Ishiura et al., 1982) | Cells may be "shocked" with glycerol or dimethylsulfoxide (DMSO) to increase transfection efficiency (Ausubel et al., 1987). |
| | Diethylaminoethyl (DEAE)-Dextran transfection | (Fujita et al., 1986; Lopata et al., 1984; Selden et al., 1986) | Most useful for transient, but not stable, transfections. Chloroquine can be used to increase efficiency. |
| | Electroporation | (Neumann et al., 1982; Potter, 1988; Potter et al., 1984; Wong and Neumann, 1982) | Especially useful for hard-to-transfect lymphocytes. |
| | Cationic lipid reagent transfection | (Elroy-Stein and Moss, 1990; Felgner at al., 1987; Rose et al., 1991; Whitt et al., 1990) | Applicable to both in vivo and in vitro transfection. |
| | Retroviral | Production exemplified by (Cepko et al., 1984; Miller and Buttimore, 1986; Pear et al., 1993) Infection in vitro and in vivo: (Austin and Cepko, 1990; Bodine et al., 1991; Fekete and Cepko, 1993; Lemischka et al., 1986; Turner et al., 1990; Williams et al., 1984) | Lengthy process, many packaging lines available at ATCC. Applicable to both in vivo and in vitro transfection. |
| | Polybrene | (Chaney et al., 1986; Kawai and Nishizawa, 1984) | |
| | Microinjection | (Capecchi, 1980) | Can be used to establish cell lines carrying integrated copies of AAP DNA sequences. |
| | Protoplast fusion | (Rassoulzadegan et al., 1982; Sandri-Goldin et al., 1981; Schaffner, 1980) | |
| Insect cells (in vitro) | Baculovirus systems | (Luckow, 1991; Miller, 1988; O'Reilly et al., | Useful for in vitro production of |

TABLE D-continued

Methods to introduce nucleic acid into cells

| Cells | Methods | References | Notes |
|---|---|---|---|
| | | 1992) | proteins with eukaryotic modifications. |
| Yeast | Electroporation | (Becker and Guarente, 1991) | |
| | Lithium acetate | (Gietz et al., 1998; Ito et al., 1983) | |
| | Spheroplast fusion | (Beggs, 1978; Hinnen et al., 1978) | Laborious, can produce aneuploids. |
| Plant cells (general reference: (Hansen and Wright, 1999)) | Agrobacterium transformation | (Bechtold and Pelletier, 1998; Escudero and Hohn, 1997; Hansen and Chilton, 1999; Touraev and al., 1997) | |
| | Biolistics (microprojectiles) | (Finer et al., 1999; Hansen and Chilton, 1999; Shillito, 1999) | |
| | Electroporation (protoplasts) | (Fromm et al., 1985; Ou-Lee et al., 1986; Rhodes et al., 1988; Saunders et al., 1989) May be combined with liposomes (Trick and al., 1997) | |
| | Polyethylene glycol (PEG) treatment | (Shillito, 1999) | |
| | Liposomes | May be combined with electroporation (Trick and al., 1997) | |
| | in planta microinjection | (Leduc and al., 1996; Zhou and al., 1983) | |
| | Seed imbibition | (Trick and al., 1997) | |
| | Laser beam | (Hoffman, 1996) | |
| | Silicon carbide whiskers | (Thompson and al., 1995) | |

Vectors often use a selectable marker to facilitate identifying those cells that have incorporated the vector. Many selectable markers are well known in the art for the use with prokaryotes, usually antibiotic-resistance genes or the use of autotrophy and auxotrophy mutants. Table E lists often-used selectable markers for mammalian cell transfection.

TABLE E

Useful selectable markers for eukaryote cell transfection

| Selectable Marker | Selection | Action | Reference |
|---|---|---|---|
| Adenosine deaminase (ADA) | Media includes 9-β-D-xylofuranosyl adenine (Xyl-A) | Conversion of Xyl-A to Xyl-ATP, which incorporates into nucleic acids, killing cells. ADA detoxifies | (Kaufman et al., 1986) |
| Dihydrofolate reductase (DHFR) | Methotrexate (MTX) and dialyzed serum (purine-free media) | MTX competitive inhibitor of DHFR. In absence of exogenous purines, cells require DHFR, a necessary enzyme in purine biosynthesis. | (Simonsen and Levinson, 1983) |
| Aminoglycoside phosphotransferase ("APH", neomycin, "G418") | G418 | G418, an aminoglycoside detoxified by APH, interferes with ribosomal function and consequently, translation. | (Southern and Berg, 1982) |

TABLE E-continued

Useful selectable markers for eukaryote cell transfection

| Selectable Marker | Selection | Action | Reference |
|---|---|---|---|
| Hygromycin-B-phosphotransferase (HPH) | hygromycin-B | Hygromycin-B, an aminocyclitol detoxified by HPH, disrupts protein translocation and promotes mistranslation. | (Palmer et al., 1987) |
| Thymidine kinase (TK) | Forward selection (TK+): Media (HAT) incorporates aminopterin. Reverse selection (TK−): Media incorporates 5-bromodeoxyuridine (BrdU). | Forward: Aminopterin forces cells to synthesze dTTP from thymidine, a pathway requiring TK. Reverse: TK phosphorylates BrdU, which incorporates into nucleic acids, killing cells. | (Littlefield, 1964) |

Exemplary Fusions Containing a Capture Polypeptide

A display polypeptide moiety may be fused to any capture polypeptide which can form a covalent bond with a reactant ligand which corresponds to the capture polypeptide. Preferably, both the display polypeptide moiety and the capture polypeptide retain their respective biochemical properties in the fusion polypeptide.

Figure 2:
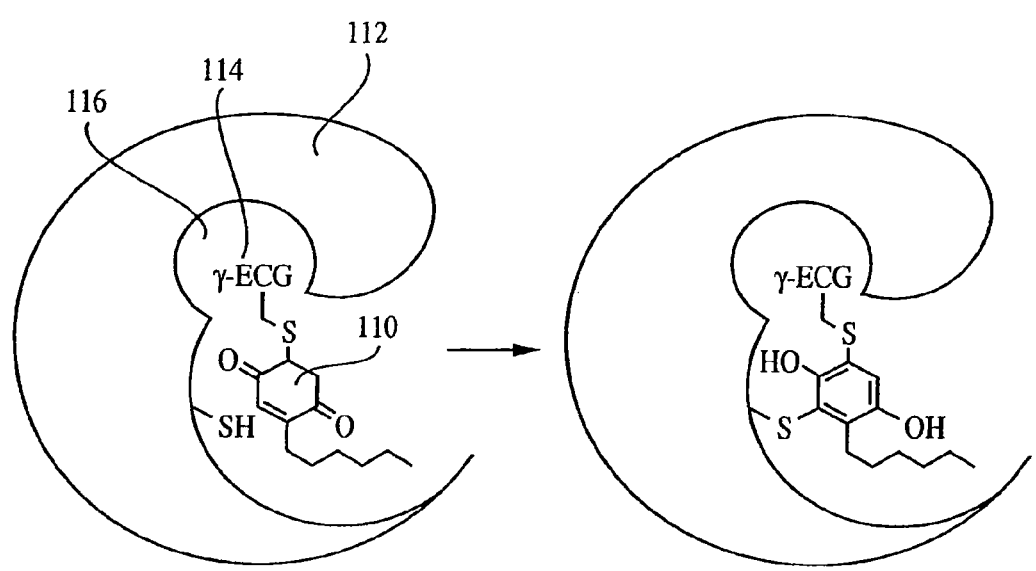
FIG. 2 illustrates a diagram of the irreversible inhibition of GST by a glutathione-quinone conjugate.

For example, glutathione-S-transferase (GST) is an enzyme which is commonly used as an affinity handle for the purification of recombinant proteins. The target protein is expressed and purified as a GST fusion and may then be treated with a protease to remove the GST domain (Smith and Johnson, 1988). The peptide glutathione is the natural cofactor which binds to GST with an affinity of approximately 100 µM (van Ommen et al., 1989). While this binding is specific in that glutathione does not bind to other enzymes, the affinity is too low for the enzyme to remain bound to the peptide. Rather, the affinity of 100 µM corresponds to a lifetime of about one minute for the bound complex. Conjugates of glutathione and benzoquinone, however, are potent reactant ligands of GST (van Ommen et al., 1991). As illustrated in FIG. 2, the glutathione portion 114 of this GST reactant ligand 110 is believed to interact with the active site 116 of GST 112. A covalent bond is formed between the reactant ligand (glutathione-benzoquinone conjugate) and the enzyme (GST), linking the reactant ligand to the GST. Although several conjugates of glutathione and benzoquinone may be used in this method, the conjugate of formula (6) is preferred.

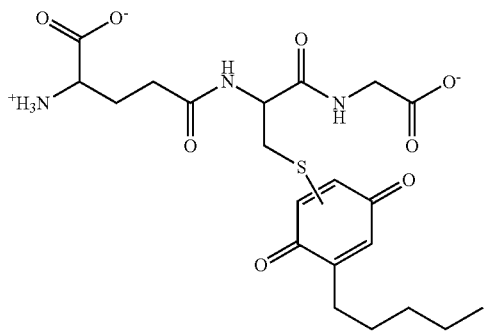

(6)

When immobilized on a surface, a compound containing the conjugate of formula (6) can react with a GST moiety, forming a covalent bond. If the GST moiety is a fusion with a display moiety, the display moiety will then be presented in a well defined orientation.

Other polypeptides which are useful as capture polypeptides include the class of highly homologous hydrolases capable of hydrolyzing a variety of natural and synthetic esters, including cutinases and lipases. These are small, globular monomeric enzymes ranging in molecular weight from 20 kD-30 kD (Longhi and Cambillau, 1999; Martinez et al., 1992). These enzymes can be expressed as a fusion polypeptide with a broad range of display moieties. The nitrophenyl phosphonate of formula (7) is an effective reactant ligand for cutinase (Deussen et al., 2000b; Martinez et al., 1994).

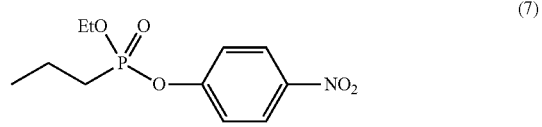 [SMILES: CCCP(=O)(OCC)Oc1ccc([N+](=O)[O-])cc1]

(7)

Several considerations make the nitrophenyl phosphonate-cutinase pair a preferred system for use in the present method. The enzyme is small (20 kD); its rate of inhibition by the reactant ligand is fast; it has been expressed in high levels in both $E.\ coli$ and yeast; and it shows excellent stability, even in organic solvents. Cutinase forms a stable, covalent adduct with immobilized phosphonate ligands which is site-specific and resistant to hydrolysis. Recombinant techniques can be used to provide fusions of cutinase with a display polypeptide (Bandmann et al., 2000; Berggren et al., 2000). The display moiety of a fusion having cutinase as the capture polypeptide will present in a well defined orientation at the interface when the cutinase is reacted with the reactant ligand on the surface. Preferably, a cutinase fusion of the invention does not comprise a purification partner. Most preferably, excluded purification partners are GST, His tag, lacZ, trpE, maltose binding protein (MBP), thioredoxin, or the Fc portion of an immunoglobulin.

Another example of a useful capture polypeptide is His-tag. The relatively small polypeptide, containing, for example, about 6 histidine units linked together, can be expressed as a fusion polypeptide with a broad range of display moieties. His-tag is typically used in the purification of recombinant proteins due to the binding of the chain of histidine amino acids with Ni(II) complexes. This binding, however, is non-covalent and relatively weak. A reactant ligand for the His-tag capture polypeptide is the conjugate of formula (8):

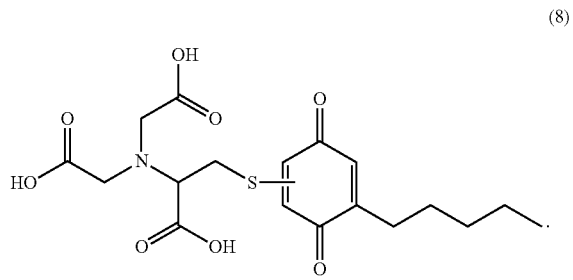

(8)

When immobilized on a surface, a compound containing the conjugate of formula (8) can react with a modified His-tag moiety, forming a covalent bond. The modified His-tag moiety for the conjugate of formula (8), is a chain of glycine-glycine-cysteine-histidine-histidine-histidine-cysteine (GGCHHHC). If the modified His-tag moiety is a fusion with a display moiety, the display moiety will then be presented in a well defined orientation.

The immobilization of fusion polypeptides containing a capture polypeptide such as GST, cutinase, or His-tag can also be applied to other polypeptide and proteins, or portions of proteins, and their corresponding reactant ligands.

The immobilization can be applied to membrane-bound proteins, which typically lose activity if removed from the membrane environment. FIG. 3 illustrates a general strategy for confining membrane associated proteins to monolayers by immobilization of a capture polypeptide. Slight modifications may be necessary for different classes of membrane proteins. Type I and II integral-membrane proteins may be modified with an N- and C-terminal capture polypeptide, respectively. For intracellular membrane-associated proteins, such as ras proteins, which are modified with a carboxy-terminal lipid, fusions may be prepared with a capture polypeptide linked by a minimal transmembrane segment flanked by charged amino acids. For membrane associated proteins, a Type II insertion sequence adjacent to the capture polypeptide may be used to pass the capture polypeptide through the membrane to lodge it on the luminal face of the E.R. during post-translational membrane insertion. The proteins may be isolated as large proteoliposomes, consisting of a relatively homogenous population of "right-side out" liposomes into which proteins are inserted with known topology using the capture polypeptide moiety, so that the capture polypeptide is on the extraluminal face. These may then be arrayed onto a monolayer substrate presenting the reactant ligand.

Referring to FIG. 3, reactant ligands 160 may be fused to the substrate 162 to install a supported lipid bilayer 164, in which the display polypeptide 166 is homogenously oriented with its cytoplasmic face available for biochemical interrogation. The bilayer is immobilized on the surface due to formation of a covalent bond between the reactant ligands 160 and the capture polypeptide 168 which is present as a fusion of the display polypeptide 166. With such surfaces, the physiological state of cells can be examined by the ability of cell extracts to phosphorylate specific membrane protein cytoplasmic domains and to assemble soluble cytoplasmic proteins into complexes onto the test surface. These post-translational modifications and/or protein binding events can readily be detected.

For display polypeptides that interact with extracellular ligands, arrays may be constructed having membrane proteins arranged with their extracellular domains facing "up" by placing the capture polypeptide moiety on the cytoplasmic domains of the target proteins. For integral membrane display polypeptides, the capture polypeptide sequence may be linked to the N or C terminus, as appropriate, to add a cytoplasmic capture polypeptide moiety. In turn, GPI-linked secreted display polypeptides, like lipid-linked intracellular proteins, can be studied by cloning a minimal transmembrane segment with charged borders onto the C-terminus of the display polypeptide that connects the display polypeptide to a capture polypeptide moiety. The resulting fusion polypeptide may be expressed as a transmembrane protein with an intracellular capture polypeptide domain. These fusion polypeptides may be solubilized, purified, and fused into oriented liposomes or vesicles. These liposomes may again be applied to the substrate to form a supported bilayer.

Formation of Fusion Polypeptides

The fusion may contain a polypeptide as the display moiety. Although some fusion polypeptides of useful capture polypeptides and display polypeptides are known, the invention is not limited to these fusion polypeptides. Rather, a fusion polypeptide of any display polypeptide and any capture polypeptide may be made. Fusion polypeptides can be produced, for example, by native chemical ligation or by recombinant methods. Recombinant approaches to fusion polypeptides involve the action of a host cell, such as a prokaryotic or eukaryotic host cell in culture.

1. Mature

A nucleotide sequence can encode a mature polypeptide. A "mature" form of a polypeptide is the product of a precursor form or proprotein. The precursor or proprotein includes, by way of non-limiting example, the full-length gene product, encoded by the corresponding gene. Alternatively, it may be defined as the polypeptide, precursor or proprotein encoded by an open reading frame described herein. The product "mature" form arises, again by way of nonlimiting example, as a result of one or more naturally occurring processing steps as they may take place within the cell, or host cell, in which the gene product arises. Examples of such processing steps leading to a "mature" form of a polypeptide include the cleavage of the N-terminal methionine residue encoded by the initiation codon of an open reading frame, or the proteolytic cleavage of a signal peptide or leader sequence. Thus a mature form arising from a precursor polypeptide that has residues 1 to N, where residue 1 is the N-terminal methionine, would have residues 2 through N remaining after removal of the N-terminal methionine. Alternatively, a mature form arising from a precursor polypeptide or protein having residues 1 to N, in which an N-terminal signal sequence from residue 1 to residue M is cleaved, would have the residues from residue M+1 to residue N remaining. Further as used herein, a "mature" form of a polypeptide or protein may arise from a step of post-translational modification other than a proteolytic cleavage event. Such additional processes include, by way of non-limiting example, glycosylation, myristoylation or phosphorylation. In general, a mature polypeptide or protein may result from the operation of only one of these processes, or a combination of any of them.

2. Active

An active polypeptide or polypeptide fragment, including an active protein or active protein fragment, retains a biological and/or an immunological activity similar, but not necessarily identical, to an activity of the naturally-occurring (wild-type) polypeptide, such as a display polypeptide, including mature forms. A particular biological assay, with or without dose dependency, can be used to determine polypeptide activity. A nucleic acid fragment encoding a biologically-active portion of a polypeptide can be prepared by isolating a portion of the sequence that encodes a polypeptide having the corresponding biological activity, expressing the encoded portion of the polypeptide (e.g., by recombinant expression in vitro) and assessing the activity of the encoded portion of the polypeptide. Immunological activity refers to the ability to induce the production of an antibody against an antigenic epitope possessed by a native polypeptide; biological activity refers to a function, either inhibitory or stimulatory, caused by a native polypeptide that excludes immunological activity.

3. Isolated/Purified Polypeptides

An "isolated" or "purified" polypeptide, protein or biologically active fragment is separated and/or recovered from a component of its natural environment. Contaminant components include materials that would typically interfere with diagnostic or therapeutic uses for the polypeptide, and may include enzymes, hormones, and other proteinaceous or non-proteinaceous materials. Preferably, the polypeptide is purified to a sufficient degree to obtain at least 15 residues of N-terminal or internal amino acid sequence. To be substantially isolated, preparations having less than 30% by dry weight of contaminating material (contaminants), more preferably less than 20%, 10% and most preferably less than 5% contaminants. An isolated, recombinantly-produced polypeptide or biologically active portion is preferably substantially free of culture medium, i.e., culture medium represents less than 20%, more preferably less than about 10%, and most preferably less than about 5% of the volume of the polypeptide preparation. Examples of contaminants include cell debris, culture media, and substances used and produced during in vitro synthesis.

4. Biologically Active

Biologically active portions of a polypeptide include peptides comprising amino acid sequences sufficiently homologous to or derived from the amino acid sequences of the polypeptide that include fewer amino acids than the full-length polypeptide, and exhibit at least one activity of the polypeptide. Biologically active portions comprise a domain or motif with at least one activity of the native polypeptide. A biologically active portion of a particular polypeptide can be a polypeptide that is, for example, 10, 25, 50, 100 or more amino acid residues in length. Other biologically active portions, in which other regions of the polypeptide are deleted, can be prepared by recombinant techniques and evaluated for one or more of the functional activities of a native polypeptide.

Immobilization of Reactant Ligands

The present invention includes the immobilization of a reactant ligand onto a surface. The reactant ligand may be any moiety which interacts with a corresponding capture polypeptide to form a covalent bond. For example, the reactant ligand may be a transition metal complex, an organic compound, or a polypeptide.

Immobilization of reactant ligands to a surface may be achieved by a variety of methods. Typically, the reactant ligand is chemically modified with a linking group, which is a chemical moiety which can bind to the surface. For example, the linking group may contain an organometallic group such as a silane or an organotitanate. The linking group may contain a polymerizable group which can form a covalent bond with a surface, such as through a photolytic reaction or a thermal reaction. The linking group may contain a diene or a dienophile which is capable of undergoing a Diels-Alder reaction with a dienophile or diene (respectively) on the surface. The linking group may contain an amine moiety (—NHR, —NH$_2$, —NR$_2$) which can react with an acid surface (Chapman et al., 2000). For example, a reactant ligand containing an amine linking group can be immobilized on a dextran polymer which has acidic groups on the surface. The linking group may be a thiol or a disulfide which may bond with metallic surfaces including gold. The linking group may also contain a group which is capable of releasing the ligand from a portion or all of the linking group when subjected to a specific stimulus (Hodneland and Mrksich, 2000).

The surface may be any material to which a reactant ligand can be immobilized. For example, the surface may be metal, metal oxide, glass, ceramic, polymer, or biological tissue. The surface may include a substrate of a given material and a layer or layers of another material on a portion or all of the surface of the substrate. The surfaces may be any of the common surfaces used for affinity chromatography, such as those used for immobilization of glutathione for the purification of GST fusion polypeptides. The surfaces for affinity chromatography include, for example, sepharose, agarose, polyacrylamide, polystyrene, and dextran. The surface need not be a solid, but may be a colloid, an exfoliated mineral clay, a lipid monolayer, a lipid bilayer, a gel, or a porous material.

The immobilization method preferably provides for control of the position of the reactant ligand on the surface. By controlling the position of individual reactant ligands, patterns or arrays of the ligands may be produced. The portions of the surface which are not occupied by the reactant ligand preferably do not interfere with the ligand or with the polypeptides with which the ligand interacts. More preferably, the portions of the surface which are not occupied by the reactant ligand do not allow nonspecific adsorption of polypeptides or polynucleotides. Surfaces presenting reactant ligands can be made into polypeptide or protein chips if they are contacted with fusions containing the corresponding capture polypeptide and another polypeptide or protein. Surfaces presenting reactant ligands can be made into polynucleotide chips if they are contacted with fusions containing the corresponding capture polypeptide and a polynucleotide.

Self Assembled Monolayers

Self assembled monolayers (SAMs) of alkanethiolates on gold are an important class of model surfaces for mechanistic studies of the interactions of proteins and cells with surfaces. SAMs can be inert in biological fluids, in that they prevent protein adsorption and cell adhesion, and provide surfaces for patterning the positions and shapes of attached biological substances (Chen et al., 1997; Mrksich et al., 1997). The attachment of ligands to these inert SAMs provides surfaces to which proteins and other receptors selectively bind. Monolayers presenting peptide ligands, for example, have been used to control the adhesion of cells (Houseman and Mrksich, 2001; Mrksich, 2000; Roberts et al., 1998; Yousaf et al., 2001) and monolayers presenting oligonucleotides have been used for probing gene expression in cells (Bamdad, 1998).

Alkanethiols useful in the present invention include those having the structure shown in formula (9):

HS-L-Q-T    (9)

where -L- is -(A$_x$-B$_y$-E$_z$-D)$_w$-; each A, B, E and D is individually C(R$_A$R$_A$')—, —C(R$_B$R$_B$')—, —C(R$_E$R$_E$')—, and —C(R$_D$R$_D$')—, respectively; each R$_A$, R$_B$, R$_E$ and R$_D$ is selected from the group consisting of H, alkyl, alkenyl, alkynyl, aryl and heterocyclic radical, or any two of $R_A$, $R_B$, $R_E$ and $R_D$ together form a bond, or any two of $R_A$, $R_B$, $R_E$ and $R_D$ together with the atoms to which they are bonded form a ring; each $R_A'$, $R_B'$, $R_E'$ and $R_D'$ is selected from the group consisting of H, alkyl, alkenyl, alkynyl, aryl and heterocyclic radical, or any two of $R_A'$, $R_B'$, $R_E'$ and $R_D'$ together form a bond, or any two $R_A'$, $R_B'$, $R_E'$ and $R_D'$ together with the atoms to which they are bonded form a ring; each x, y and z is individually either 0 or 1; and w is 1 to 5;

-Q- is selected from the group consisting of

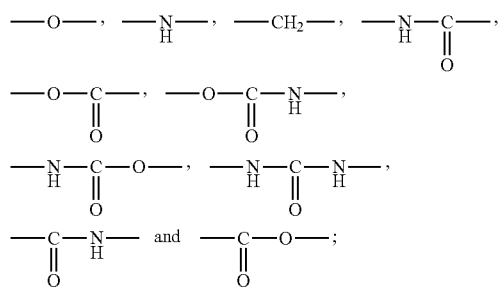

and -T contains a reactant ligand.

Disulfides useful in the present invention include those having the structure shown in formula (10):

where -L-, -Q- and -T have the same meaning as in formula (9), and -J is selected from the group consisting of H, halogen, R, —OR, —NRR', —C(O)R, and —C(O)OR; R is selected from the group consisting of alkyl, alkenyl, alkynyl, aryl and heterocyclic radical; R' is selected from the group consisting of H, alkyl, alkenyl, alkynyl, aryl and heterocyclic radical; such that the disulfide does not selectively bind avidin or streptavidin.

Preferably, -L- contains 6 to 20 carbon atoms, more preferably 8 to 18 carbon atoms. Preferably, -L- contains 1 or 0 double bonds, or 1 triple bond.

Most preferably, -L- is an alkylene containing 6 to 18 carbon atoms.

Preferably, -Q- is —O— or —CH$_2$—.

Preferably, J- is a moiety of formula (II):

or is an alkyl having 1 to 4 carbon atoms, or is —(CH$_2$)$_c$(OCH$_2$CH$_2$)$_n$OH, or is a pyridyl group (—NC$_5$H$_5$); where -L'-, -Q'-, and -T' have the same meaning as -L-, -Q-, and -T respectively, c is 2 to 20, and n is 1 to 10. Most preferably -J is a moiety of formula (II).

Alkanethiols and disulfides may be synthesized using reagents and reactions well known to those of ordinary skill in the art, such as those described in (March, 1994; Morrison and boyd, 1983). For example, the following reaction scheme may be used:

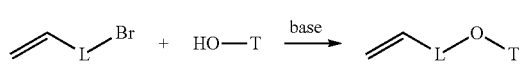

Further photolysis with thioacetic acid and AIBN (2,2'-azobisisobutyronitrile) in THF (tetrahydrofuran) forms the thioester of the alkanethiol of formula (9). Hydrolysis then gives alkanethiols of formula (9) with -Q- being —O—.

Optionally, —OH groups, carbonyl groups (>C=O), and N—H groups in -T may be protected using standard protecting groups, and deprotection may take place before, after, or during hydrolysis of the thioester. Protection and deprotection methods are described in (Greene and Wuts, 1991). For alkanethiols of formula (9) where -Q— is —NH—, Br in the above reaction scheme above may be replaced with NH$_2$, and the OH may be converted to a tosylate or mesylate. For alkanethiols of formula (9) where -Q- is —CH$_2$—, the OH may be converted to a tosylate or mesylate, and Br converted to the corresponding Grignard. For alkanethiols of formula (9) where -Q- is —CO—O—, Br in the above reaction scheme may be replaced with CO$_2$H. For alkanethiols of formula (9) where -Q- is —O—00-, Br in the above reaction scheme may be replaced with OH, and the OH may be converted to the corresponding acid. For alkanethiols of formula (9) where -Q- is —NH—CO—, Br in the above reaction scheme may be replaced with NH$_2$, and the OH may be converted to the corresponding acid. For alkanethiols of formula (9) where -Q- is —CO—NH—, Br in the above reaction scheme may be replaced with CO$_2$H, and the OH may be converted to the corresponding primary amine (for example, by tosylation or mesylation followed by reaction with ammonia). For alkanethiols of formula (9) where -Q- is —NH—CO—NH—, Br in the above reaction scheme may be replaced with NH$_2$, and the OH may be converted to the corresponding isocyanate. For alkanethiols of formula (9) where -Q- is —NH—CO—O—, Br in the above reaction scheme may be replaced with —N=C=O to give an isocyanate, which is then reacted with the hydroxyl as shown. Similarly, the disulfides may be formed by first forming alkanethiols, followed by oxidative coupling. When the disulfide is not symmetric, two different alkanethiols are oxidized together.

Any reactant ligand may be modified to facilitate immobilization to a surface. For example, a reactant ligand for phosphatase enzymes is a compound of formula (12), which may be ionized as shown, depending on the pH of the environment:

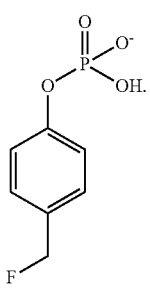

This reactant ligand may be modified and immobilized as illustrated in the following reaction scheme:

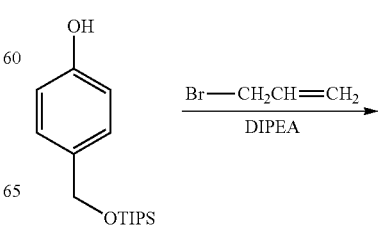

27
-continued
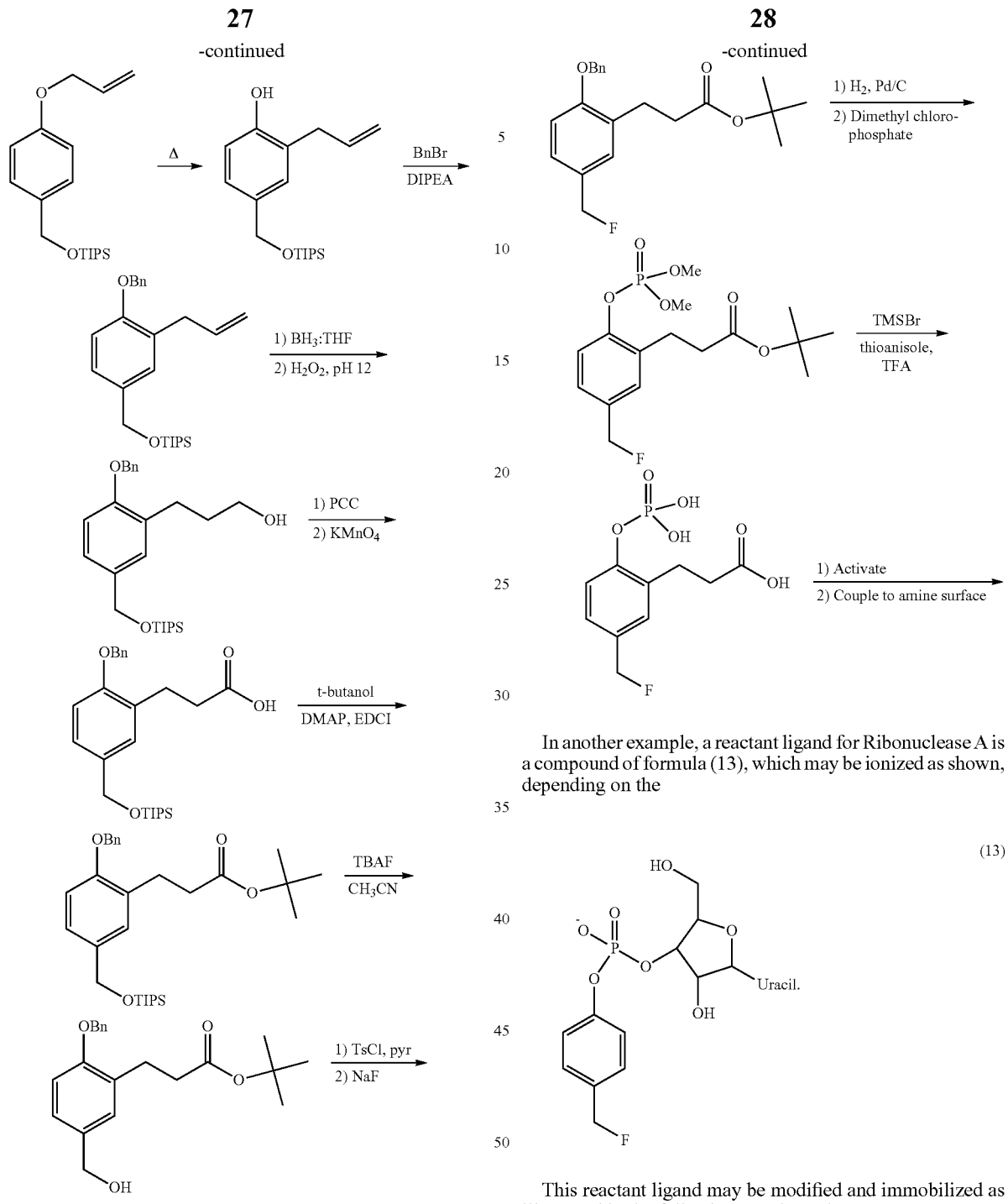
28
-continued
In another example, a reactant ligand for Ribonuclease A is a compound of formula (13), which may be ionized as shown, depending on the
This reactant ligand may be modified and immobilized as illustrated in the following reaction scheme:
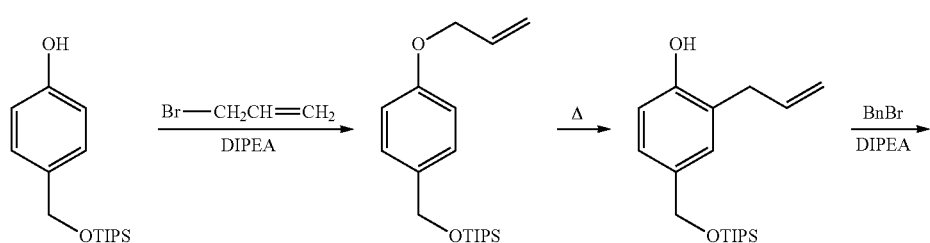

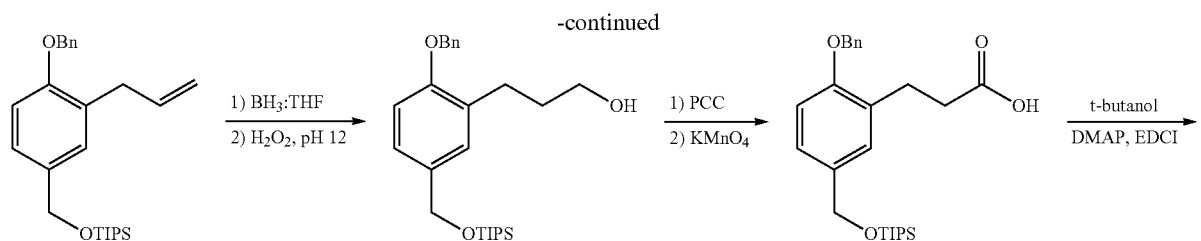
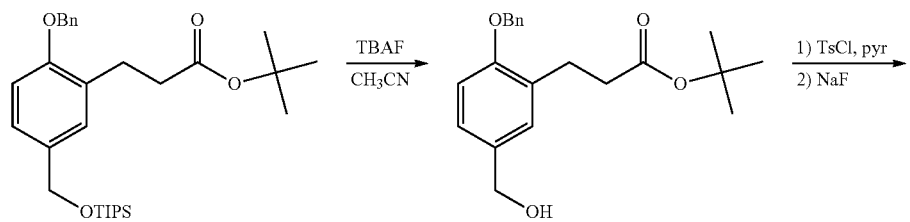
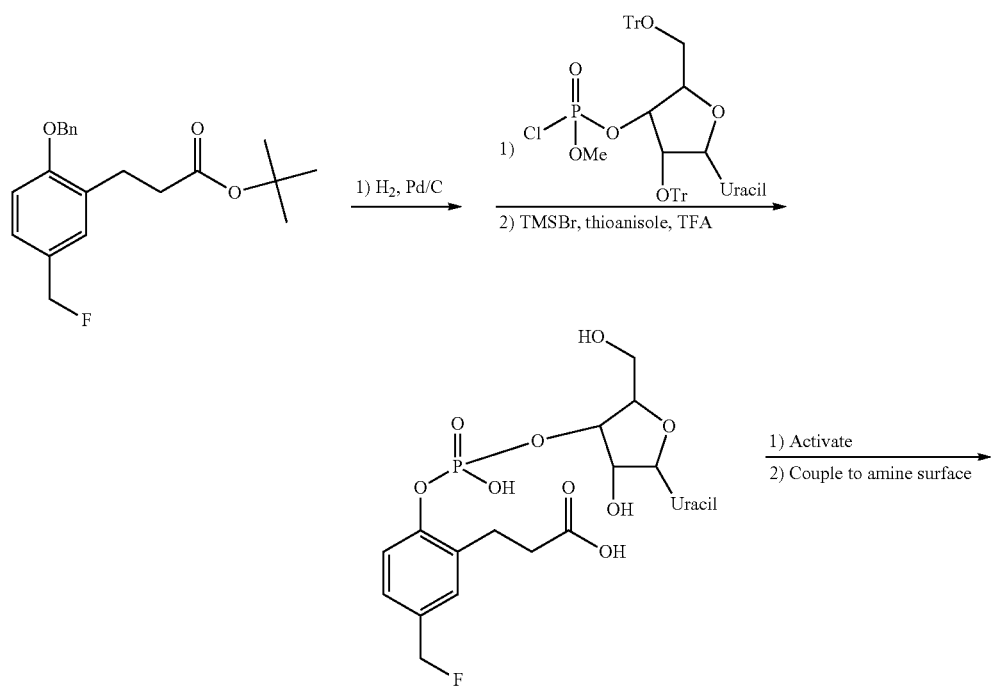
In another example, reactant ligands for cystein proteases, such as cruzain, papain, and cathepsin B, include compounds of formulae (4) and (5):
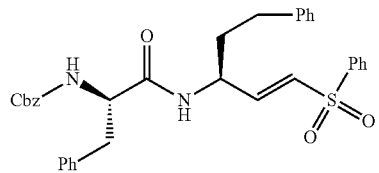
(4)
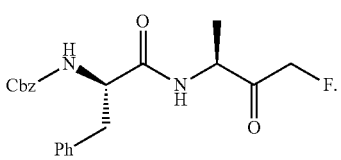
(5)
The reactant ligand of formula (4) may be modified with an alkyldisulfide as illustrated in the following reaction scheme:

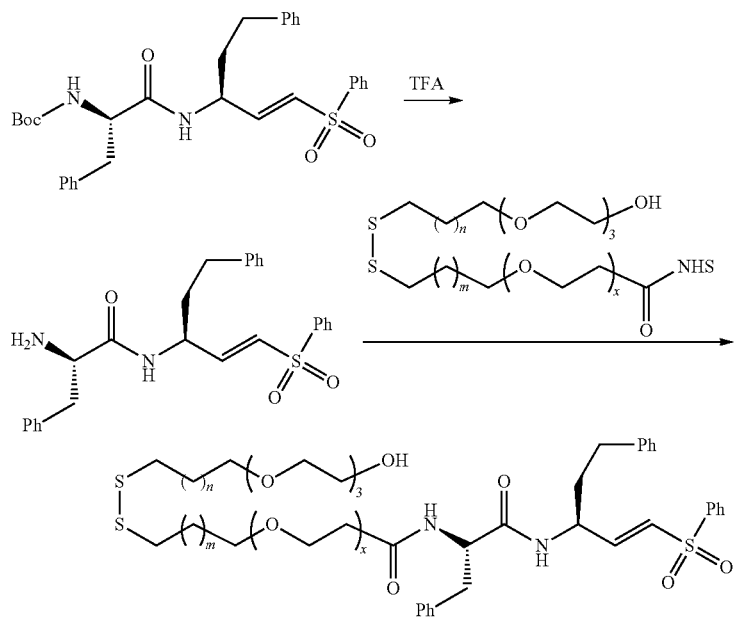

Alternatively, the reactant ligand of formula (4) may be modified and immobilized as illustrated in the following reaction scheme:

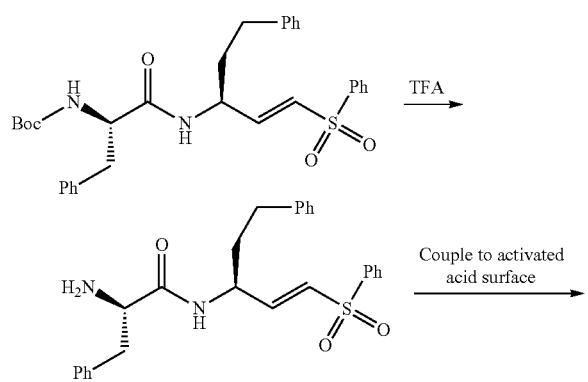

The reactant ligand of formula (5) may be modified with an alkanethiol as illustrated in the following reaction scheme:

Preparation of SAMs

When applied to a surface containing gold, the alkanethiols and disulfides will form SAMs. In the case of the alkanethiols, the moiety attaches to the surface through the sulfur atom, and the hydrogen is believed to be lost or bound to the interface. In the case of the disulfides, the disulfide bridge is broken, and the remaining moieties attach to the surface through the sulfur atoms. The surface preferably has a plurality of alkanethiolate moieties shown in formula (14):

Surf-S-L-Q-T           (14)

where -L-, -Q-, and -T have the same meaning as in formula (4), and Surf designates where the moiety attaches to the surface. The density of moieties on the surface is typically $10^{10} \pm 50\%$ per square centimeter. The moieties of the present invention may cover the entire surface alone or with other moieties, or may be patterned on the surface alone or with other moieties. Patterning may be carried out, for example, by microprinting (Chen et al., 1997; Mrksich et al., 1997; Mrksich and Whitesides, 1995).

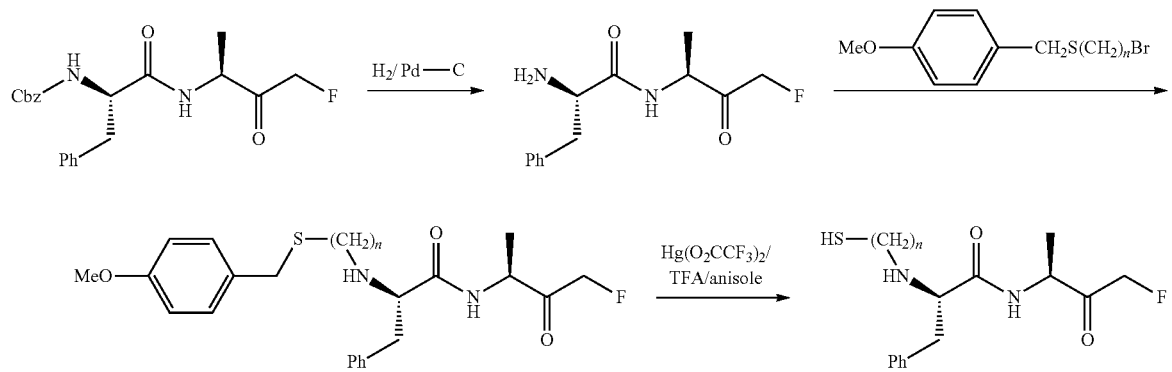

Preferably the surface contains gold. More preferably, the surface contains 50 to 100 atom percent gold. Preferably, the surface is pure or fine gold, or an alloy of gold with copper, and/or silver.

The surface may be on a substrate. The substrate may have the same composition as the surface (for example a gold surface on a gold plate), or the surface may be, for example, a film, foil, sheet, or plate, on a substrate having a different composition. The substrate may be any material, such as metal, metal oxide, glass, ceramic, plastic, or a natural material such as wood. Examples of substrates include glass, quartz, silicon, transparent plastic, aluminum, carbon, polyethylene, polypropylene, sepharose, agarose, dextran, polysytrene, polyacrylamide, a gel, and porous materials.

The surface material may be attached to the substrate by any of a variety of methods. For example, a film of the surface material may be applied to the substrate by sputtering or evaporation. If the surface material is a foil or sheet, it could be attached with an adhesive. Furthermore, the surface need not completely cover the substrate, but may cover only a portion of the substrate, or may form a pattern on the substrate. For example, sputtering the substrate, covering those portions of the substrate where no surface material is desired, may be used to pattern portions of the substrate. These patterns may include an array of regions containing, or missing, the surface material.

Arrays of Immobilized Proteins

A protein chip is an array of regions containing immobilized protein, separated by regions containing no protein or immobilized protein at a much lower density. For example, a protein chip may be prepared by applying SAMs containing the reactant ligand and/or SAMs containing a mixture of the moiety of formula (4) and a moiety that produces an inert surface on regions of the surface that are to have proteins attached or are intended to have proteins at a higher density. Inert SAMs include those containing moieties which are terminated in short oligomers of the ethylene glycol group (($OCH_2CH_2$)$_n$OH, n=3-6)) or a moiety which is terminated in a group having multiple hydroxyl groups, such as mannitol (Luk et al., 2000). The remaining regions could be left uncovered, or could be covered with SAMs that are inert. The rapid kinetics of binding and covalent immobilization of polypeptide moieties to a surface, by way of a covalent reaction with a reactant ligand, facilitates the use of spotting to deposit proteins onto the surfaces. The arrays can be rinsed to remove all but the specifically immobilized fusion polypeptides.

Figure 4:
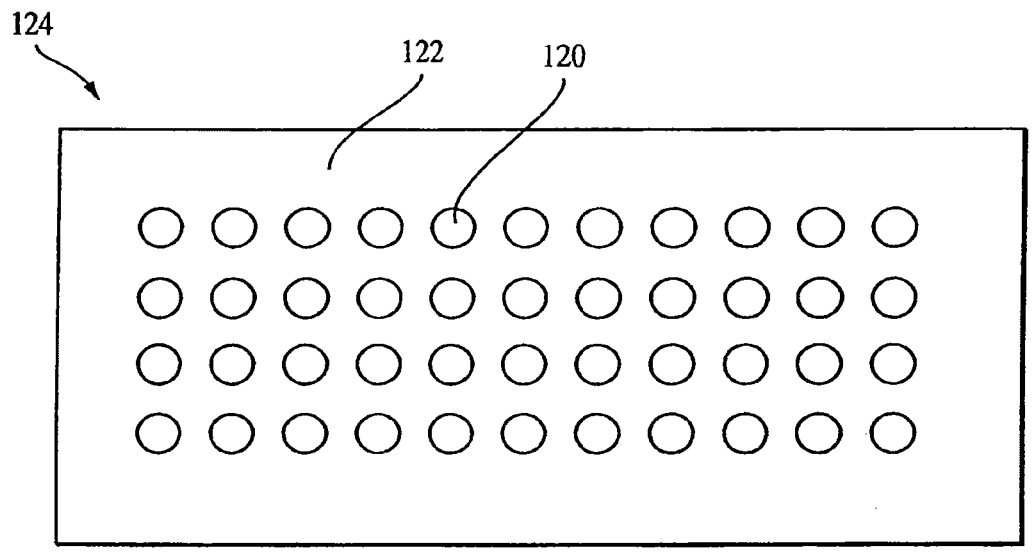
FIG. 4 illustrates a patterned substrate.
Figure 5:
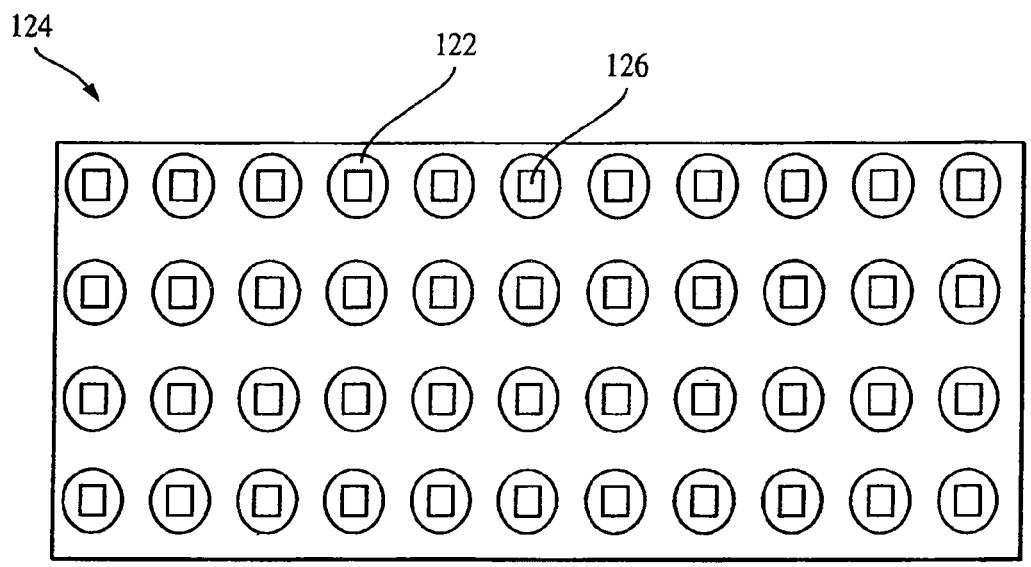
FIG. 5 illustrates another patterned substrate.

For example, FIG. 4 illustrates one possible pattern, where circles 120 contain a SAM of the present invention, and the remainder 122 of the surface is covered with a SAM that presents an inert surface, all on a surface 124. Another example, FIG. 5 illustrates another possible pattern, where squares 126 contain a SAM of the present invention, and regions 128 surrounding the squares contain a SAM that presents an inert surface, all on a surface 124. Once the surface is patterned as desired, the proteins may be allowed to attach in the regions containing SAMs of the present invention, by contacting those regions with proteins.

Since the covalent binding of the capture polypeptide is specific to the reactant ligand on the surface, only the desired fusion polypeptide is immobilized when the surface is otherwise inert to the adsorption or binding of polypeptides. It is not necessary to passivate the surface through adsorption of BSA or casein, which can often interfere with selective binding interactions at the surface. Additionally, the fusion polypeptides do not require purification because only polypeptides containing the capture polypeptide will become immobilized to the surface. This strategy gives excellent control over both the orientation and the density of immobilized polypeptide, the latter being determined by the density of the capture polypeptide on the monolayer. The rapid rate of polypeptide immobilization can result in low consumption of the fusion polypeptide.

Applications of Immobilized Polypeptides

Immobilized polypeptides are useful for a broad range of applications. For example, analysis of the interaction of a composition on a polypeptide is useful in screening the composition for bioactivity and/or pharmaceutical utility. Surfaces containing immobilized polypeptides which are reactive, such as enzymes, can be used as catalytic surfaces for influencing the reactions of biochemical systems as well as other chemical reactions, such as esterifications and polymerizations. For a given application, the immobilized polypeptides may be organized into an array or may be distributed randomly on the surface.

Immobilized polypeptides may, for example, be used to assay the presence, the concentration, and/or the behavior of particular biomolecules. Typical assays assess physiological responses in cells by quantifying polypeptide abundance. Activity assays provide for detection of activation or repression of intracellular signaling pathways as well as activation of cell to cell signaling. In general, cellular signaling is mediated by enzymes that phosphorylate, proteolyse or ubiquitinate polypeptides. The activated state of a cell is usually best determined through the kinetic measurement of the activity of such modifying enzymes. Polypeptide arrays made by the present method can be used to quantify specific enzymatic activities in a sample by their specific and differential modification of the immobilized and arrayed polypeptides.

A protein chip preferably uses surface-immobilized display polypeptides which are available for physiologic interaction with proteins in a sample. The protein in a sample is referred to as a protein partner. For example, the rates and extent of post-translational modifications of the display polypeptides by purified enzymes and cell extracts can then be measured. Antibodies can be used to detect post-translational modifications of the display polypeptides. Phosphorylation, acetylation, ubiquitination, proteolysis and other protein modifications each create specific epitopes (Blaydes et al., 2000; White et al., 1999).

An example of regulated protein modification that can readily be assayed by this strategy is tyrosine phosphorylation (Hunter, 1998). Monoclonal antibodies specific to phosphotyrosine are commercially available. The two protein domains, SH2 (Sawyer, 1998) and PTB (Eck, 1995) also bind specifically to phosphotyrosines and can be used to detect tyrosine kinase activity. Fusion polypeptides containing the capture polypeptide may be immobilized onto monolayer surfaces such that the display polypeptide may be modified by kinase enzymes. Surface plasmon resonance spectroscopy (SPR) may then be used to measure the binding of antibodies to quantitate the yield of phosphorylation. SPR is an excellent analytical technique for characterizing protein-protein interactions because it can monitor the reactions in real time, providing kinetic information, and it does not require modification of proteins with fluorophores or other labels. Fluorescently labeled antibodies and binding proteins may also be used in order to access information on the homogeneity and/or distribution of protein modification. Fluorescent surfaces may then be imaged by epi-fluorescence microscopy and/or scanned, for example using an AFFYMETRIX GMS428 array scanner (AFFYMETRIX; Santa Clara, Calif.) or a chip-reading machine.

To detect the binding of an antibody to the display polypeptide, a label may be used. The label may be coupled to the binding antibody, or to a second antibody that recognizes the first antibody, and is incubated with the sample after the primary antibody incubation and thorough washing. Suitable labels include fluorsescent moieties, such as fluorescein isothiocyanate; fluorescein dichlorotriazine and fluorinated analogs of fluorescein; naphthofluorescein carboxylic acid and its succinimidyl ester; carboxyrhodamine 6G; pyridyloxazole derivatives; Cy2, 3 and 5; phycoerythrin; fluorescent species of succinimidyl esters, carboxylic acids, isothiocyanates, sulfonyl chlorides, and dansyl chlorides, including propionic acid succinimidyl esters, and pentanoic acid succinimidyl esters; succinimidyl esters of carboxytetramethylrhodamine; rhodamine Red-X succinimidyl ester; Texas Red sulfonyl chloride; Texas Red-X succinimidyl ester; Texas Red-X sodium tetrafluorophenol ester; Red-X; Texas Red dyes; tetramethylrhodamine; lissamine rhodamine B; tetramethylrhodamine; tetramethylrhodamine isothiocyanate; naphthofluoresceins; coumarin derivatives; pyrenes; pyridyloxazole derivatives; dapoxyl dyes; Cascade Blue and Yellow dyes; benzofuran isothiocyanates; sodium tetrafluorophenols; 4,4-difluoro-4-bora-3a,4a-diaza-s-indacene. Suitable labels further include enzymatic moieties, such as alkaline phosphatase or horseradish peroxidase; radioactive moieties, including $^{35}$S and $^{125}$I-labels; avidin (or streptavidin)-biotin-based detection systems (often coupled with enzymatic or gold signal systems); and gold particles. In the case of enzymatic-based detection systems, the enzyme is reacted with an appropriate substrate, such as 3,3'-diaminobenzidine (DAB) for horseradish peroxidase; preferably, the reaction products are insoluble. Gold-labeled samples, if not prepared for ultrastructural analyses, may be chemically reacted to enhance the gold signal; this approach is especially desirable for light microscopy. The choice of the label depends on the application, the desired resolution and the desired observation methods. For fluorescent labels, the fluor is excited with the appropriate wavelength, and the sample observed with a microscope, confocal microscope, or FACS machine. In the case of radioactive labeling, the samples are contacted with autoradiography film, and the film developed; alternatively, autoradiography may also be accomplished using ultrastructural approaches.

To use antibodies to detect the presence of an epitope, the approach can be summarized as the steps of:
(1) Preparing the surface by washing with buffer or water
(2) Applying the antibody
(3) Detecting bound antibody, either via a detectable label that has been added to the antibody, or a labeled-secondary antibody.

Surfaces may be washed with any solution that does not interfere with the epitope structure. Common buffers include salines and biological buffers, such as bicine, tricine, and Tris.

The surface is then reacted with the antibody of interest. The antibody may be applied in any form, such as $F_{ab}$ fragments and derivatives thereof, purified antibody (affinity, precipitation, etc.), supernatant from hybridoma cultures, ascites or serum. The antibody may be diluted in buffer or media, preferably with a protein carrier, such as the solution used to block non-specific binding sites. The antibody may be diluted, and the appropriate dilutions are usually determined empirically. In general, polyclonal sera, purified antibodies and ascites may be diluted 1:50 to 1:200,000, more often, 1:200 to 1:500. Hybridoma supernatants may be diluted 1:0 to 1:10, or may be concentrated by dialysis or ammonium sulfate precipitation and diluted if necessary. Incubation with the antibodies may be carried out for as little as 20 minutes at 37° C., 2 to 6 hours at room temperature (approximately 22° C.), or 8 hours or more at 4° C. Incubation times can easily be empirically determined by one of skill in the art.

For example, an assay for the presence of kinase activity in a biological sample using tyrosine kinases is useful, because these enzymes exhibit well-documented specificities to a large number of protein substrates. A fusion polypeptide containing a display polypeptide having a polypeptide tail containing the consensus phosphorylation substrate IYGEF for the soluble tyrosine kinase src, and a capture polypeptide may be made (Brown and Cooper, 1996; Thomas and Brugge, 1997). Src is a well-known protein tyrosine kinase that functions in growth-factor signaling. Incubation of the substrate with a biological sample containing Src and ATP results in phosphorylation of the display peptide, and the resulting phosphotyrosine epitope is detected through the binding of an anti-phosphotyrosine antibody.

This strategy may be expanded to assay the phosphorylation of full length targets (FIG. 6). For example, Shc, a 450 residue adapter molecule in tyrosine kinase signaling having a central domain of ~150 residues, can be multiply phosphorylated by Src. Once phosphorylated, this domain recruits GRB2 via SH2-mediated phosphotyrosine binding to promote downstream signal transduction through Ras and other effectors. A GST-Shc fusion is a well-characterized reagent that can be readily expressed in bacteria (Okabayashi et al., 1996). A GST-Shc mutant fusion polypeptide with phenylalanines replacing the tyrosines at Src phosphorylation sites is a useful control. Surfaces coated with the two fusion polypeptides may be treated with buffer solutions containing Src and ATP, and phosphorylation may be detected with an anti-phosphotyrosine monoclonal antibody and monitored by SPR. The binding of the monoclonal antibody to the phosphotyrosines of the immobilized GST-Shc may also be detected with a fluorescently labeled secondary antibody specific for the monoclonal antibody. The surfaces can be scanned to determine the distribution of phospho-epitopes over the surface. As a complementary test, the binding of GRB2 to the surface after treatment with Src and ATP may be assayed, also using SPR.

Another useful activity assay involves proteolysis. Proteolysis is an important form of protein modification that is involved in protein maturation, processing and destruction. Proteases cleave the peptide bond adjacent to or within a specific recognition sequence, often leading to dissociation of a protein into two or more separate peptides. SPR can detect the dissociation of a cleaved protein directly. Fusion polypeptides can be prepared with a capture polypeptide fused to a reporter domain by way of a display polypeptide that is a substrate for the protease of interest. In this way, the presence of the protease will lead to cleavage of the fusion polypeptide and release of the reporter from the surface. In one strategy, a peptide antigen can be used as the reporter, and antibody binding experiments may be performed as described above to determine whether the immobilized fusion polypeptide underwent proteolysis. Alternatively, green fluorescent protein (GFP) or red fluorescent protein (RFP) may be used to quantify protease activity by fluorescence imaging (FIG. 7).

For example, the protease caspase-3, which is involved in the propagation of programmed cell death (apoptosis) may be used as a display polypeptide. In the cell, caspase-3 cleaves gelsolin, an 80 kD actin filament severing protein, to release an unregulated 41 kD N-terminal domain. A carboxyl-terminal fusion of a linking polypeptide with gelsolin may be immobilized to the monolayer surface. Treatment of the surface with caspase-3 or a cellular extract and monitoring proteolysis in real time by release of the 41 kD fragment from the substrate as measured by SPR. With this model system, the density and environment of the immobilized protein can readily be optimized to yield efficient and complete proteolysis of the gelsolin in the presence of physiologically relevant concentrations of activated caspase-3. Fusion polypeptides can be prepared such that the proteolysis will result in release of antigenic peptides such as HA and RFP.

Another substrate for proteases is poly-ADP ribose polymerase (PARP). This 116 kD protein is cleaved into 24 kD and 89 kD peptides by caspase-3. Polyclonal antibodies are commercially available that recognize only the cleaved 89 kD carboxyl-terminus of PARP. A surface modified with PARP-GST can be treated with a cell extract from apoptotic cells and then washed free of extract. The surface can then be probed with the anti-cleaved PARP antibody and the binding detected with SPR, providing a positive signal for proteolysis. Alternatively, the binding of the anti-cleaved PARP primary antibody can be detected with a fluorescent secondary antibody and the surface scanned to detect the distribution of 89 kD cleavage product.

The activity of serine-threonine kinases may be determined by arraying a number of physiological substrates. Proline-directed kinases are a class of serine threonine-kinases that participate in at least two important signaling and cell growth pathways. MAP kinases integrate growth factor signals and stress signals to determine gene expression responses of cells to their environment. The cyclin-dependent kinases (CDK's) are the final target of all growth factor, stress and checkpoint signaling. These kinases are regulated by cyclin subunits that bind to the catalytic subunit both to activate their phosphotransferase activity and to guide them to specific substrates. Importantly, the cyclins present in the cell and therefore the cyclin-dependent kinase activities that can be detected are determined by physiological parameters such as growth status, presence of positive or negative growth factors, cell stresses and nutrient availability. Thus, the proliferative state of a cell is defined by the abundance and activity of the different cyclin/CDK complexes.

As a sensitive detector of cell stress, a probe for general activation of apoptotic pathways may be carried out by arraying 24-48 different caspase substrates as GST-RFP sandwich fusion polypeptides. A large number of substrates cleaved by caspases during apoptotic cell death are now known. Substrates include, for example, cytoskeletal proteins, nuclear lamins and other nuclear structural proteins, DNAses, transcription factors, signaling proteins, and cell cycle and checkpoint regulators. Many such substrates may be preferentially or specifically cleaved by one or another of the apoptotic caspases (-2, -3, -6, -7, -8, -9 and -10).

EXAMPLES

Materials $^1$H NMR spectra were recorded on BRUKER 400 MHz and 500 MHz spectrometers (BRUKER NMR, Billerica, Mass.) in CDCl$_3$ or D$_2$O, with chemical shifts reported relative to the residual peak of the perspective solvent. $^{31}$P NMR was recorded on a BRUKER 500 MHz spectrometer in CDCl$_3$ with chemical shifts reported relative to H$_3$PO$_4$.

Reactions were performed under a nitrogen atmosphere. Reagents were used as received unless otherwise stated. THF was distilled under argon from sodium/benzophenone, and dichloromethane (CH$_2$Cl$_2$) was distilled from CaH$_2$. Absolute ethanol was purchased from AAPER ALCOHOL AND CHEMICAL COMPANY, Shelbyville, Ky. Flash chromatography was carried out using Merck Silica gel 60 (230-400) mesh (Merck KGaA, Darmstadt, Germany). Thin-layer chromatography (TLC) was performed on Whatman silica gel plates (0.25 mm thickness) (Whatman Inc., Clifton, N.J.). All compounds were visualized with either short-wave ultraviolet light or a cerium sulfate/ammonium heptamolybdenate tetrahydrate staining solution. All reagents were purchased from either ALDRICH (Milwaukee, Wis.), LANCASTER (Windham, N.H.) or FISHER SCIENTIFIC (Hampton, N.H.).

*Fusarium solani f. pisi* was purchased from American Type Culture Collection (ATCC No. 38136). All oligonucleotides were purchased from LIFE TECHNOLOGIES (Rockville, Md.). *E. coli* strains were obtained from NOVAGEN (Madison, Wis.). PCR reactions were performed using Vent® thermopolymerase (NEW ENGLAND BIOLABS, Beverly, Mass.). All other enzymes used in plasmid construction were purchased from PROMEGA (Madison, Wis.) unless otherwise noted.

Example 1

Synthesis of Soluble Reactant Ligand for GST n-Pentyldimethoxybenzene 1. 3.12 g (22.58 mmol) of 1,4-dimethoxybenzene was dissolved in 25 ml of THF. To this solution was added 10.8 ml of 2.5 M n-butyllithium solution in pentane. The addition was carried out dropwise at 0° C. under nitrogen over 20 min. The reaction mixture was stirred for 1 hour at room temperature, after which 3.36 ml of n-bromopentane at 0° C. was added, and the resultant mixture stirred for 15 hours at room temperature. Solvent was removed under reduced pressure, and the reaction mixture was dissolved in ethyl acetate, washed with water and brine, and dried over MgSO$_4$. Removing the solvent under vacuum gave 4.4 g (93.5% yield) of 1 as a clear oil.

n-Pentyltetrachlorodimethoxybenzene 2. 520 mg (2.496 mmol) of n-pentyldimethoxybenzene 1 was dissolved in 10 ml of acetic acid. To this solution was added 3.14 g (3 eq) benzyltrimethylammonium tetrachloroiodate. The reaction mixture was stirred overnight at 70° C. and concentrated to yellow oil. The reaction mixture was dissolved in CH$_2$Cl$_2$ and washed with water, saturated NaHCO$_3$, and brine. Silicagel chromatography using a 20:1 mixture of hexane to ethyl acetate (EA) gave 610 mg (78% yield) of 2 as a white solid.

n-Pentyltetrachlorohydroquinone 3. To a solution of 190 mg (0.61 mmol) of 2 in CH$_2$Cl$_2$ at −78° C., 0.3 ml (5 eq) of BBr$_3$ was added dropwise. After warming to room temperature, the reaction mixture was stirred for 4 hr. The BBr$_3$ was quenched with ethyl ether at −78° C. and with water at room temperature. Extraction with CH$_2$Cl$_2$ and silicagel chromatography (hexane:EA=8:1) gave 136 mg (79% yield) of 3 as a white solid.

n-Pentyltetrachlorobenzoquinone 4. To a solution of 110 mg (0.388 mmol) of 3 in methanol, 880 mg (10 eq) of 2,3-Dichloro-5,6-dicyano-1,4-benzoquinone (DDQ) was added. The reaction mixture was stirred for 2 hr, and then the solvent was removed. Silicagel chromatography (hexane:EA=20:1) gave 4 as an orange solid with quantitative yield.

Glutathione-dichtoroquinone conjugate 5. To a solution of 10 mg (0.0355 mmol) of 4 in methanol, 11 mg (1 eq) of glutathione in water was added. The reaction mixture was stirred for 1 hr, and then the solvent was removed. Trituration with hexane and ethyl ether (1:1 solution) gave the adduct 5 as an orange solid.

This synthesis may be illustrated by the following reaction scheme:

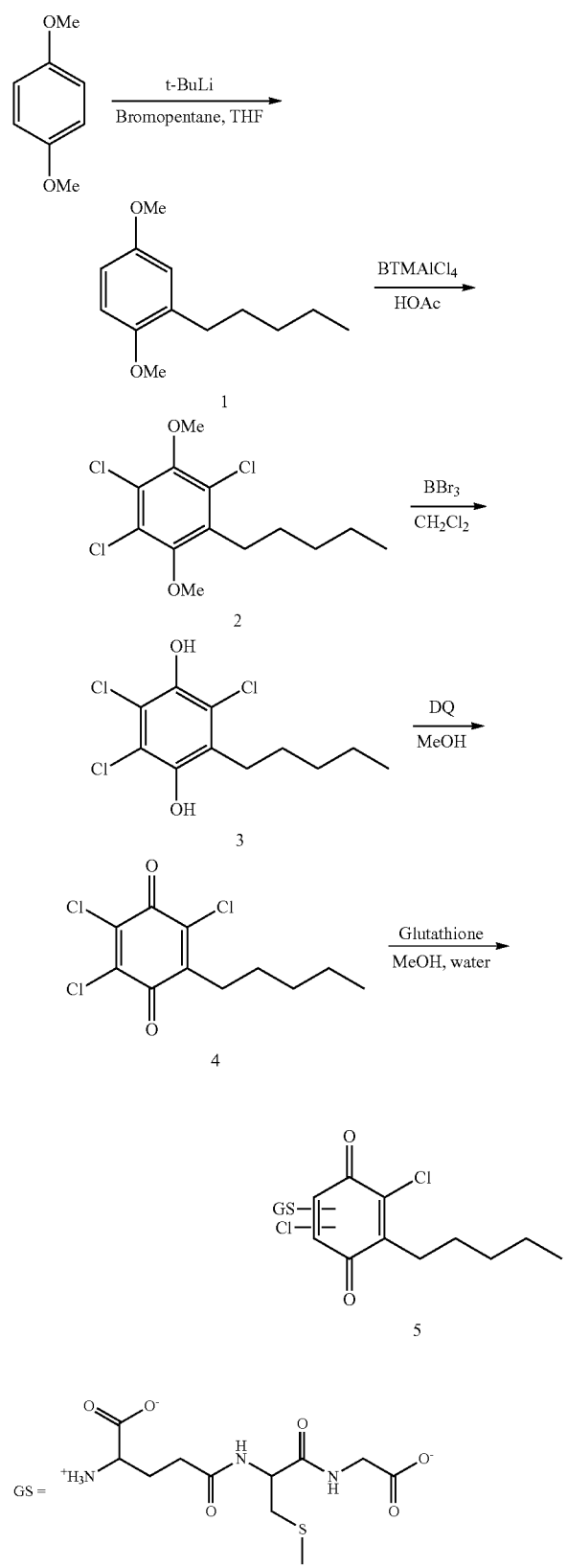

Example 2

Inhibition Studies

Figure 8A:
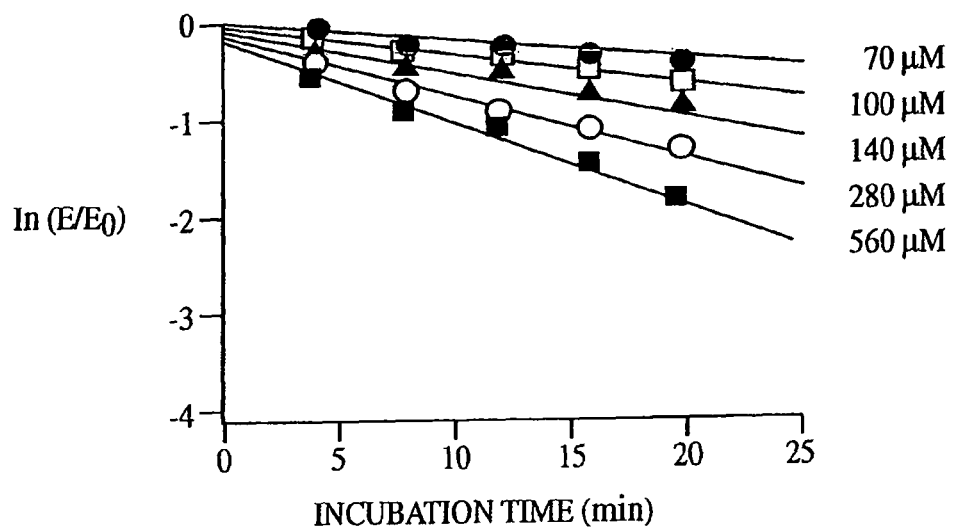
FIG. 8 is a graph of the binding behavior of a reactant ligand with GST.
Figure 8B:
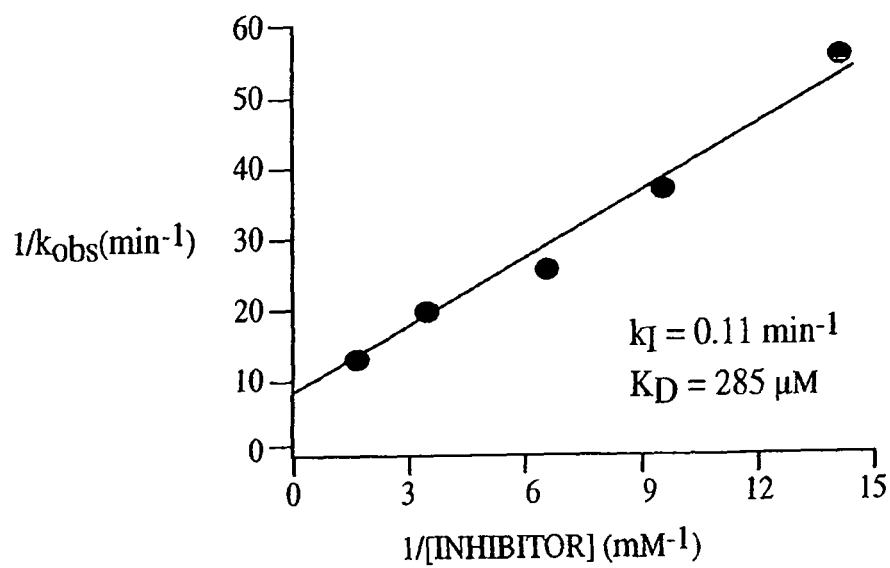

The binding and covalent bonding of a conjugate of formula (6) to GST was measured using the method described (Kitz and Wilson, 1962). FIG. 8 presents a graph of the results. This analysis showed that the inhibitor binds GST with a dissociation constant of 285±120 mM, and that the bound complex undergoes an irreversible cross-linking reaction with a first-order rate constant of 0.11±0.03 min$^{-1}$ (FIG. 8B). These mechanistic constants predicted that the immobilization of GST to surfaces presenting the reactant ligand would proceed with a half-life of 8 minutes when a 1 mM solution of protein was used.

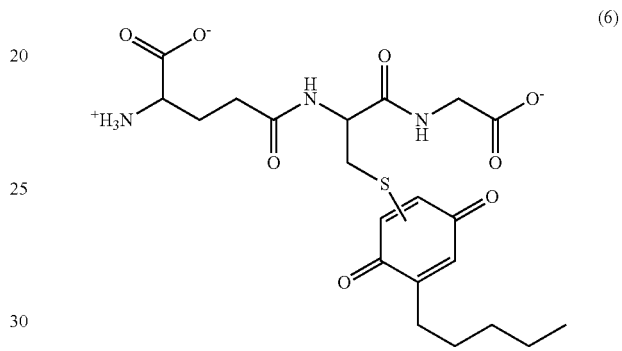

(6)

Example 3

Synthesis of Immobilizable Reactant Ligand for GST

Ditetrahydropyran-hydroquinone 7. To a solution of hydroquinone (5 g, 45.4 mmol) in THF was added dihydropyran (17 ml, 4 eq) and HCl (2 ml). The mixture was stirred for 8 hr. The solvent was removed, and the mixture was mixed with ethyl acetate (EA), washed with saturated NaHCO$_3$, water and brine, and dried over MgSO$_4$. Silicagel chromatography (hexane:EA=4:1) and washing with hexane gave 2.5 g (20% yield) of 7 as a white solid.

Ditetrahydropyran-hydroquinone-hexylbromide 8. 503 mg (1.81 mmol) of ditetrahydropyran-hydroquinone 7 was dissolved in 25 ml of THF. To this solution was added 1.6 ml (1.5 eq) of 1.7 M t-butyllithium solution in pentane. This addition was dropwise at 0° C. under nitrogen over 20 min. The reaction mixture was then stirred for 1 hr at room temperature. To this mixture was added 1.1 ml (4 eq) of 1,6-dibromohexane at 0° C., followed by stirring for 15 hr at room temperature. The solvent was removed under reduced pressure, and the reaction mixture was mixed with ethyl acetate, washed with water and brine, and dried over MgSO$_4$. The silicagel chromatography (hexane:EA=20:1) gave 738 mg (92% yield) of 8 as a white solid.

Ditetrahydropyran-hydroquinone-EG5-alkanethiol-trityl 9. 1.43 g (2.144 mmol) of EG5-alkanethol-trityl 14 was dissolved in 5 ml of DMF. To this solution was added 250 mg (3 eq) of sodiumhydride (60% in mineral oil) at 0° C. under nitrogen over 20 min. The reaction mixture was stirred for 1 hr at 0° C., and then for 2 hr at room temperature. To this mixture was added 1.07 g (1.1 eq) of the bromide 8 in THF at 0° C., and the mixture was stirred overnight at room temperature. The excess hydride was quenched with water, the solvent was removed under reduced pressure, the reaction mixture was mixed with ethyl acetate, washed with water and brine, and dried over MgSO$_4$. The silicagel chromatography (hexane:EA=1:1) gave 965 mg (44% yield) of 9 as a clear oil.

Hydroquinone-EG5-alkanethiol-trityl 10. 965 mg (0.939 mmol) of 9 was dissolved in a 3:1:1 mixture of acetic acid, THF, and water. The reaction mixture was stirred overnight. Removing the solvent under vacuum gave 801 mg (quantitative) of 10 as a clear oil.

Benzoquinone-EG5-alkanethiol-trityl 11. 840 mg (0.977 mmol) of 10 was dissolved in methanol, and to this solution was added 317 mg (2 eq) of ferric chloride. The reaction mixture was stirred for 1 hr, and the solvent was removed. The silicagel chromatography (hexane:EA=1:1) gave 235 mg (28% yield) of 11 as a brown oil.

Hydroquinone-glutathione-EG5-alkanethiol-trityl 12. 93 mg (0.108 mmol) of 11 was dissolved in methanol, and to this solution was added 30 mg (1 eq) of glutathione in water. The reaction mixture was stirred for 1 hr, and the solvent was removed. The trituration with hexane and ethyl ether (1:1 solution) gave 82 mg (72% yield) of the adduct 12 as an brown solid.

Hydroquinone-glutathione-EG5-alkanethiol 13. 10 mg (0.00858 mmol) of 12 was dissolved in CH$_2$Cl$_2$. To this solution was added 3.6 µL (2 eq) of triethylsilane and 1 ml of TFA. The reaction mixture was stirred for 2 hr, and the solvent was removed. The trituration with hexane and ethyl ether (1:1 solution) gave 13 as a brown solid.

This synthesis may be illustrated by the following reaction scheme:

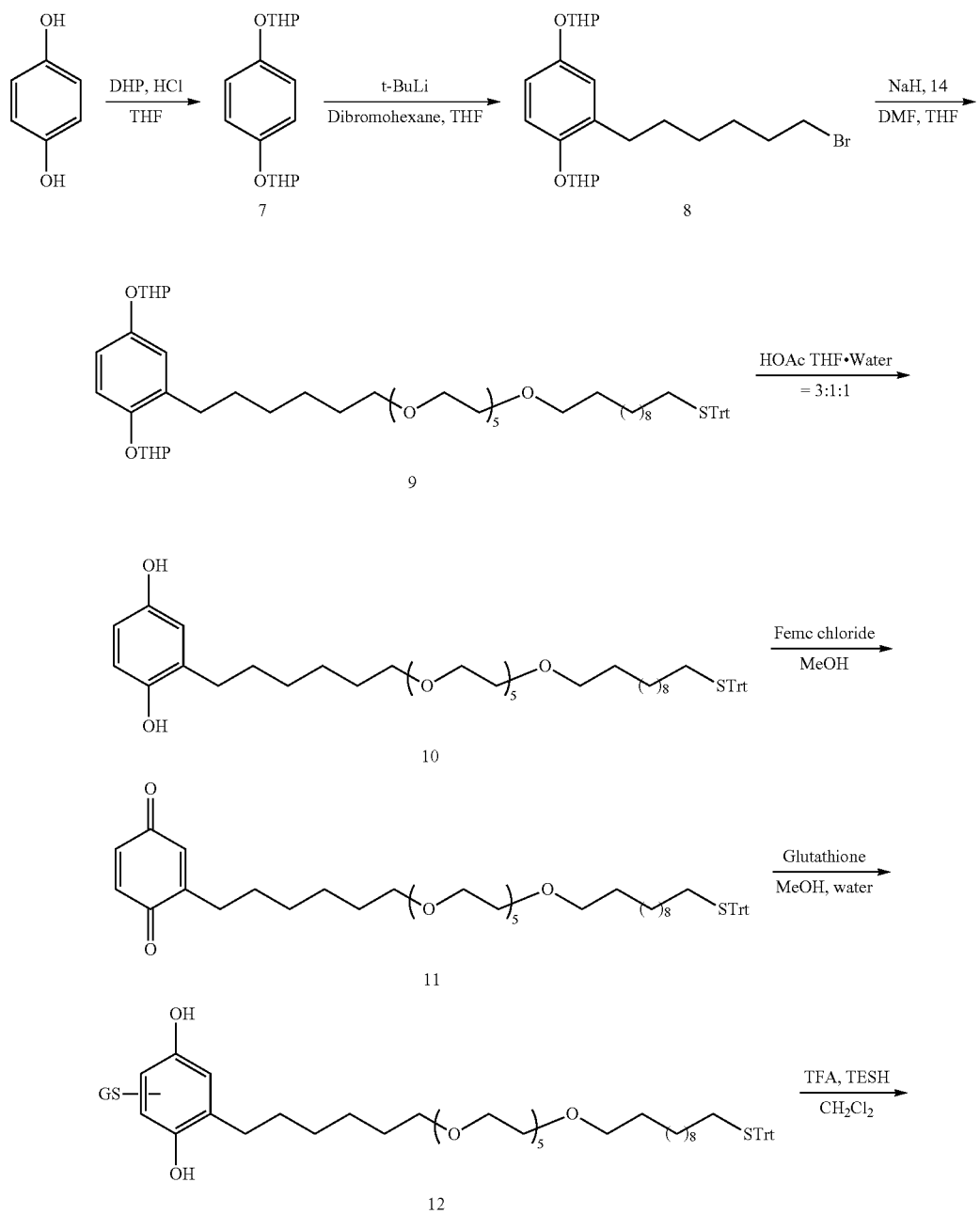

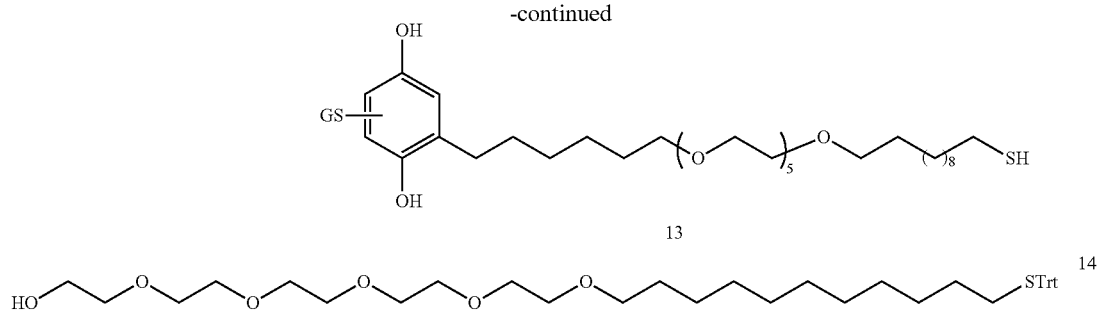

Example 4

Surface Preparation & Characterization

Gold surfaces were prepared by evaporation of an adhesive layer of titanium (5.5 nm) followed by a layer of gold (55 nm) onto microscope cover glass (FISHERBRAND 24×50-2, FISHER SCIENTIFIC). Evaporations were performed using an electron beam evaporator (THERMIONICS VE-100, THERMIONICS VACUUM PRODUCTS, Port Townsend, Wash.) at a pressure of $9 \times 10^{-7}$ Torr and a rate of 0.3 nm/s. The gold-coated wafers were cut into 1 cm×2 cm pieces, washed with absolute ethanol, and dried under a stream of nitrogen. The monolayers were formed by immersion of the clean gold surfaces in ethanolic solutions of thiols or disulfides (1.0 mM total concentration). After 12 h, the monolayers were rinsed with absolute ethanol and dried under a stream of nitrogen gas.

Surface Plasmon Resonance Spectroscopy (SPR) was performed with a BIACORE 1000 instrument (BIACORE INTERNATIONAL AB, Uppsala, Sweden). Gold-coated glass surfaces (5.5 nm Ti, 55 nm Au) presenting SAMs to be analyzed were mounted in SPR cartridges. All experiments used a flow rate of 5 µL/min.

Example 5

Immobilization of GST to SAM

Figure 9:
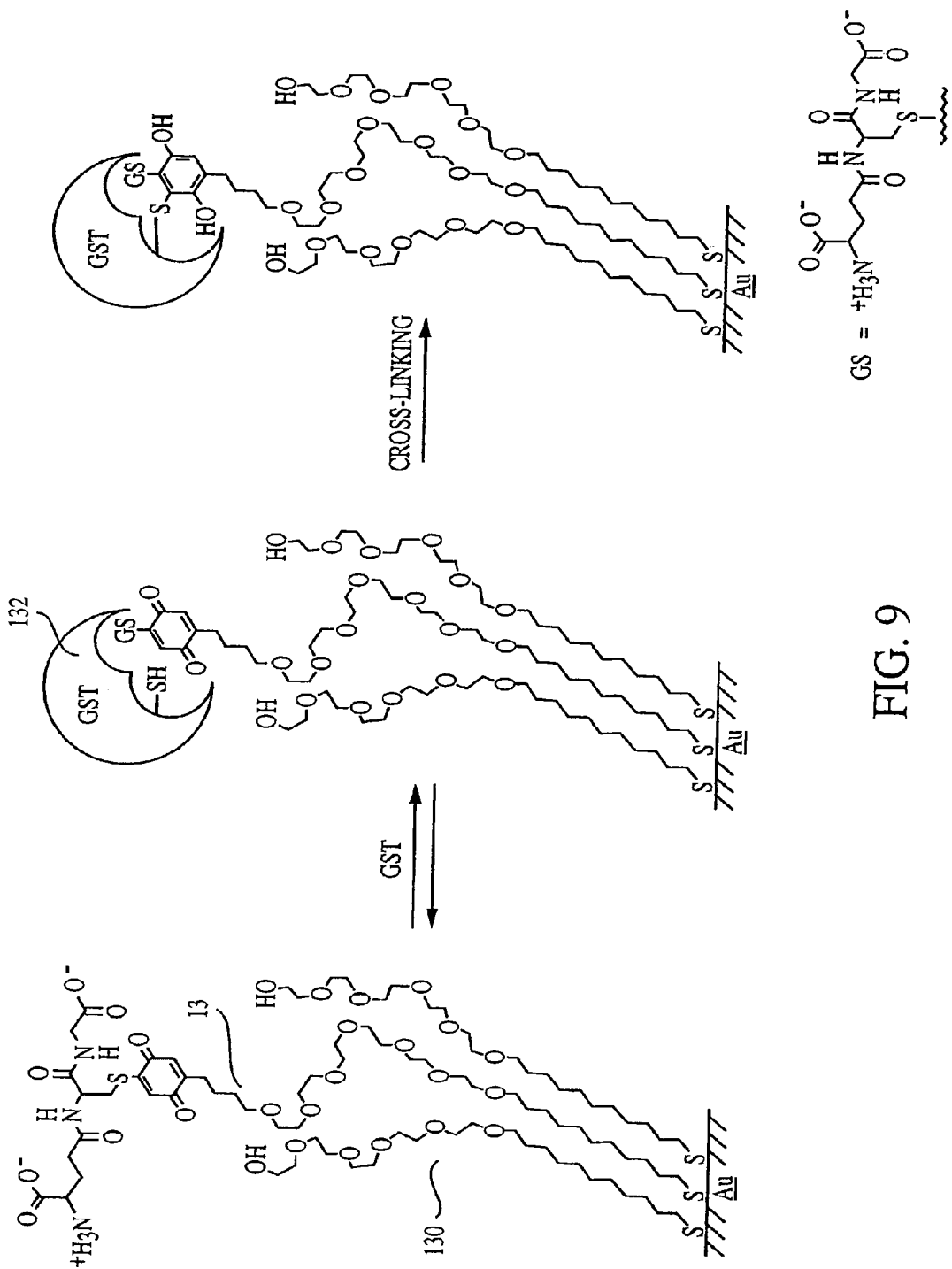
FIG. 9 is an illustration of the immobilization of GST.
Figure 10A:
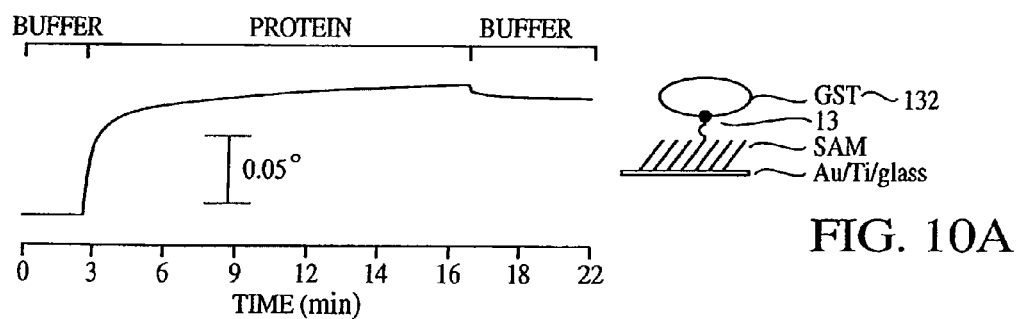
FIG. 10 is an illustration of the immobilization of GST with SPR spectroscopy data shown.
Figure 10B:
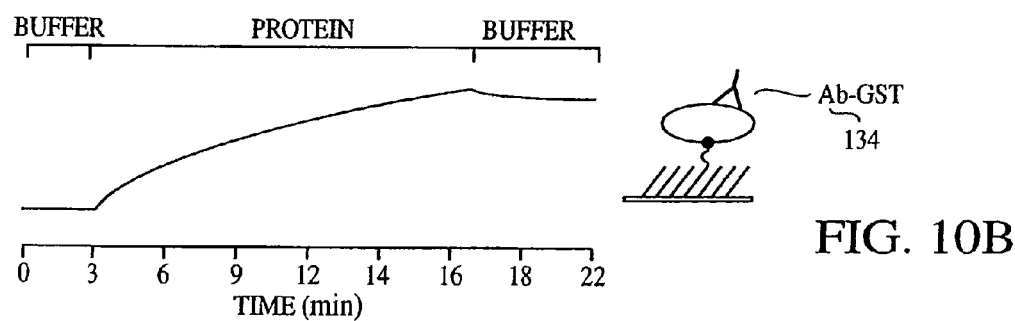
Figure 10C:
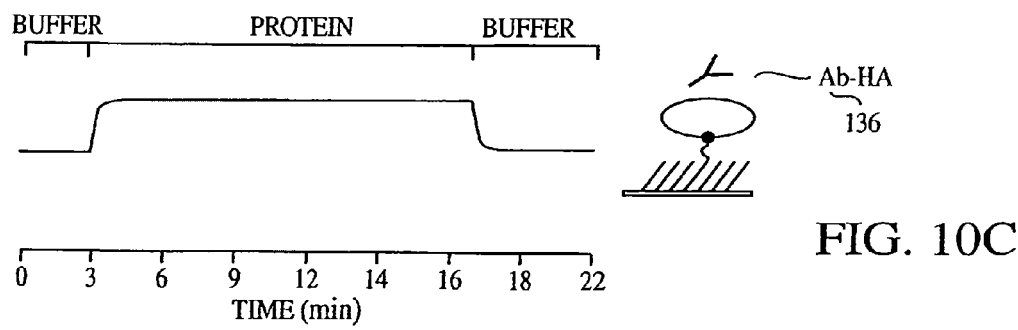
Figure 10D:
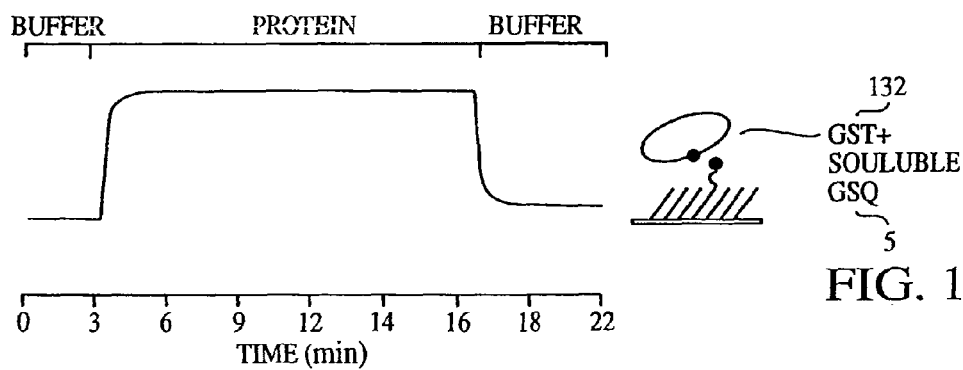

Immobilization of GST to a self-assembled monolayer was accomplished by preparing a monolayer from a 1:99 mixture of alkanethiol 13 and an alkanethiol 130 terminated in the penta(ethylene glycol) group. The alkanethiol 130 was used because it is highly effective at preventing the non-specific adsorption of protein (FIG. 9). Surface plasmon resonance (SPR) spectroscopy was used to characterize the immobilization of GST 132 to this monolayer. In these experiments, phosphate buffered saline (pH 7.4) was flowed over the monolayer for 2 minutes to establish a baseline. A solution of GST (100 µM) in the same buffer was then flowed over the monolayer for 15 minutes to observe binding. Finally the protein solution was replaced with buffer for 5 minutes to quantitate the amount of protein that was irreversibly immobilized. FIG. 10A shows that GST did bind to the monolayer, and that this binding was irreversible (that is, it did not dissociate when buffer was flowed through the cell). Further, treatment of this surface with a solution of sodium dodecyl sulfate (5 mM) for 30 min did not result in removal of protein from the surface, showing that the protein-ligand interaction was covalent (data not shown). When an antibody against GST 134 (30 µg/ml) was flowed through the cell, it bound to the immobilized GST (FIG. 10B) but showed no binding to a surface to which GST had not been immobilized. A control experiment showed that an anti-hemagglutinin antibody 136 (50 µg/ml) did not bind to monolayers to which GST was immobilized (FIG. 10C), indicating that the interaction between the antibody and immobilized GST was specific. Finally, treatment of GST with a soluble inhibitor of formula (6) prior to immobilization resulted in a near complete loss of immobilization, demonstrating the attachment of GST is specific (FIG. 10D).

Example 6

Immobilization of Display Polypeptide via GST Inhibition

Figure 10E:
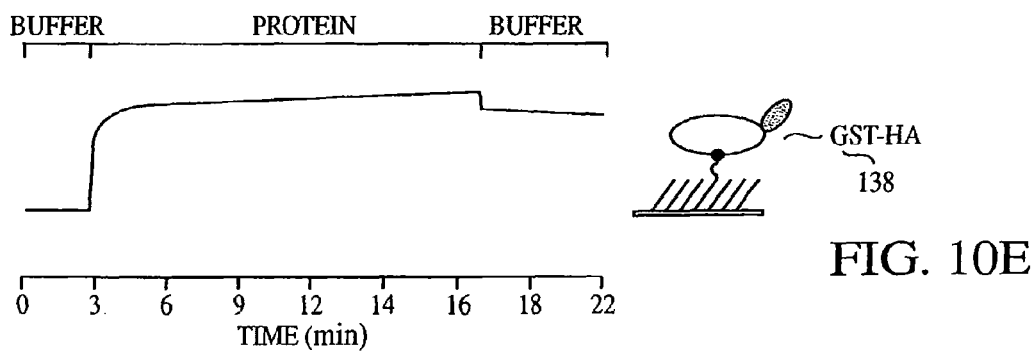
Figure 10F:
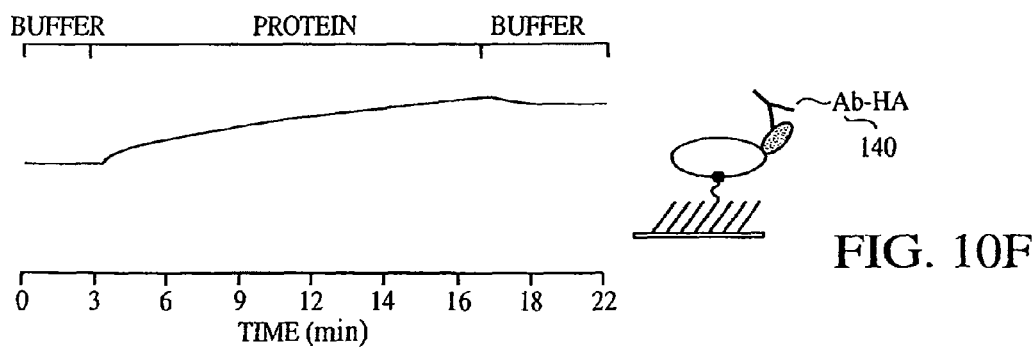

This method may be used to install peptide and protein ligands on the monolayer. A fusion of GST and the peptide hemagglutinin (GST-HA, 138), for which an antibody 140 is available, was used as a model system. FIG. 10E shows that the GST-HA fusion was efficiently immobilized to the monolayer and that the anti-HA antibody bound to the immobilized peptide (FIG. 10F). This antibody did not bind, however, to monolayers to which only GST had been immobilized, again demonstrating the specificity that is afforded with the inert monolayers.

Example 7

Preparation of Cutinase

Figure 11:
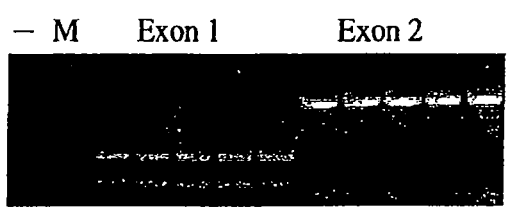
FIG. 11 is a view of an electrophoretic gel after exon amplification of cutinase.

The *Fusarium solani pisi* cutinase gene includes two exons separated by a 50 bp intron. To remove the intron each exon was amplified using primer sets containing restriction endonuclease sites. FIG. 11 shows the electrophoretic gel after exon amplification. The bands at 150 bp and 650 bp are the expected sizes of each exon. After PCR amplification and restriction digestion of the PCR products, the two exons were ligated, resulting in the intron free cutinase gene. The gene was then inserted into a plasmid using recombinant methods.

Plasmids were maintained and propagated in DH5a *E. coli*. The *F. solani* cutinase gene (SEQ ID NO:5) containing two exons and an intron was amplified from *F. solani* genomic DNA using primers Exon IF (SEQ ID NO:1) and Exon2B (SEQ ID NO:4). Two cutinase exons were then separately amplified from the purified cutinase gene using primers (SEQ ID NOS:2,3). During the PCR, a Kpn I restriction enzyme-recognition site was incorporated to each exon. Following agarose-gel purification and Kpn I restriction digestion, these exons were ligated using T4 DNA ligase, and the correctly ligated DNA was purified using 1.5% agarose-gel electrophoresis. The ligated DNA was digested with Nco I and BamH I and ligated to corresponding sites of pET-22b(+)

(NOVAGEN, INC., Madison, Wis.). The resulting plasmid, pCut22b, codes a gene for the recombinant cutinase whose N-terminal leader sequence is replaced by a pelB leader sequence for periplasmic localization of the expressed protein. Plasmid constructions were confirmed by restriction analysis and deoxynucleotide sequencing.

TABLE F

Primer oligonucleotide sequences. Restriction sites are underlined.

SEQ ID NO. 1-4:
Exon1F
GCC ACG <u>GCC ATG</u> GGC CTG CCT ACT TCT AAC CCT GCC
      Nco I

CAG GAG

Exon1B
CC <u>GGT ACC</u> CAA GTT GCC CGT CTC TGT TGA ACC TCG
   Kpn I

GGC

Exon2F
CC <u>GGT ACC</u> CTC GGT CCT AGC ATT GCC TCC AAC CTT
   Kpn I

GAG

Exon2B
CCG <u>GGA TCC</u> TCA AGC AGA ACC ACG GAC AGC CCG AAC
    BamH I

The cutinase gene was expressed in *E. coli*. Cutinase contains two disulfide bridges that are critical to its function. Since the cytoplasm of *E. coli* is reducing, the protein was exported to the oxidative environment of the periplasm to allow the disulfide bonds to form properly. Incorporation of a pelB leader sequence in place of the original leader sequence allowed cutinase to be transported to the periplasm of *E. coli*, which is an environment that facilitates proper folding of enzymes containing disulfide bonds, using the natural machinery of the bacteria.

Recombinant cutinase was expressed in *E. coli* strain BL21 (DE3) harboring pCut22b using a T7 expression system. Cells harboring pCut22b were grown in 10 mL Luria-Bertani (LB) broth supplemented with 50 μg/ml ampicillin at 37° C. The overnight culture was diluted 100-fold in a 2 L-baffled flask and grown further at 37° C. at 240 rpm. Cutinase expression was induced when OD600=0.3 by the addition of IPTG to 0.5 mM, and the expression of cutinase was allowed for 4 more hours at 37° C. with continuous shaking. Cells were then collected by centrifugation at 5,000×g for 30 min (SORVALL SLA-3000 rotor, KENDRO, Newtown, Conn.), and periplasmic proteins were collected using a sucrose osmotic shock method as described in the literature. Periplasmic fractions were further purified using a size-exclusion chromatographic method. Briefly, periplasmic fractions were loaded on a SEPHADEX G-75 column (1.8 cm×75 cm, AMERSHAM PHARMACIA BIOTECH, Piscataway, N.J.) equilibrated in buffer A (50 mM bicine, pH 8.3) at 4° C. and purified isocratically (flow rate=1 mL/min). Fractions having esterase activity were analyzed by 15% SDS-PAGE and concentrated using CENTRIPREP YM-10 (MILLIPORE, MA). Protein concentrations were determined using calculated extinction coefficient ($\epsilon_{280}$=13,370 M$^{-1}$ cm$^{-1}$) in denaturing conditions (10 mM sodium phosphate, pH 6.5, 6.0 M guanidine-HCl).

Figure 12:
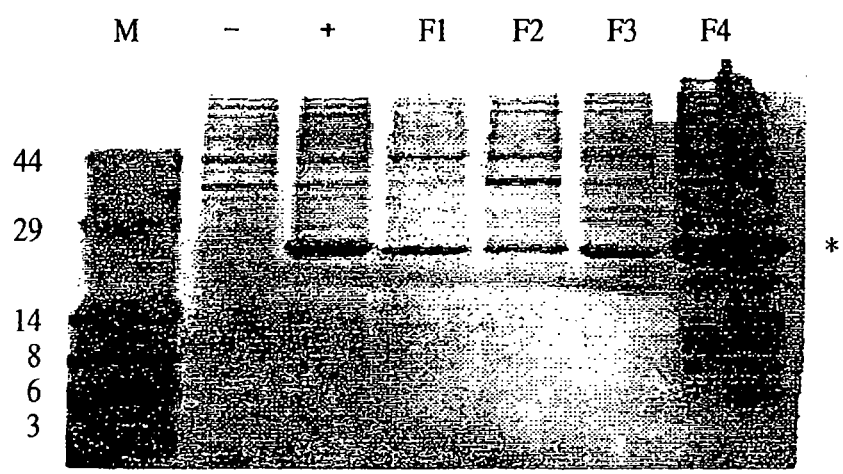
FIG. 12 is a view of an electrophoretic gel of *E. coli* lysates.

To characterize the expression of cutinase, *E. coli* lysate fractions were analyzed by SDS PAGE. All fractions of *E. coli* lysate showed a band corresponding to a molecular weight of 22 kDa, which is the expected migration of cutinase. The enzyme was efficiently expressed in *E. coli*, and the expressed protein was exported to the periplasm as shown in FIG. 12 (F1-F3). Even before purification, the periplasmic fractions showed more than 80% purity. The cutinase was further characterized by MALDI-TOF mass spectrometry, which was consistent with the calculated value (m/$z_{exp}$=22,515.89, m/$z_{calc}$=22,421). A large fraction of the expressed proteins partitioned in the cytosolic fraction.

To determine whether the protein was functional, a kinetic study of the enzymatic hydrolysis of 4-nitrophenyl butyrate, a highly active substrate of cutinase, was performed. The cutinase concentration was 1 μM. The release of PNP was followed using absorbance spectroscopy. A plot of the initial rate of the hydrolysis reaction versus substrate concentration confirmed that the reaction followed standard Michaelis-Menten kinetics with a Michaelis constant ($K_M$) of 1 mM, which is comparable to the reported value.

Spectrophotometric measurement was performed at room temperature using BECKMAN DU-640 spectrophotometer (BECKMAN COULTER, INC., Fullerton, Calif.). Esterase activity of purified recombinant cutinase was measured by monitoring p-nitrophenol butyrate (PNB) hydrolysis rates at 410 nm ($\epsilon$=8,800 M$^{-1}$cm$^{-1}$) in buffer A.

Example 8

Inhibition Studies

We first characterized the binding of soluble inhibitor 20 with cutinase. The rate of inactivation of cutinase (12 μM) was followed by the release of p-nitrophenol (PNP), for several concentrations of 20, by absorbance spectroscopy. The inhibition reaction followed Michaelis-Menten kinetics with $K_i$=65.5 μM and $k_i$=0.02 s$^{-1}$. To establish that the loss of PNP was due to inhibition, and not to enzymatic hydrolysis, we submitted the inhibited enzyme to a solution of p-nitrophenyl butyrate, which is a highly active substrate for cutinase. The enzyme was completely inhibited by one equivalent of phosphonate 20.

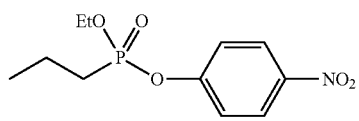

20

Inhibition of cutinase by inhibitor 20 was monitored by measuring the release of p-nitrophenol. In brief, 100 μL of inhibitor (50 μM) dissolved in DMSO was added to 900 μL of cutinase (25 μM) solution in PBS (pH=7) to give a final inhibitor concentration of 50 μM and a final cutinase concentration 25 μM. The time dependent p-nitrophenol release was measured using a BECKMAN DU-640 spectrophotometer at room temperature. Following the inhibition, the solution was passed through a size-exclusion column and the esterase activity of the recovered enzyme was measured again using PNP-butyrate assay as described above.

Example 9

Synthesis of Immobilizable Reactant Ligand for Cutinase

Cutinase has been covalently inhibited by chlorophosphonate and by many other molecules of similar structure. The leaving group 4-nitrophenol is more stable toward water hydrolysis than the chlorophosphonate, and it can be measured by absorbance spectroscopy, allowing the determination of kinetic constants. The synthesis of reactant ligand 20 has been reported (Wu and Casida, 1995). In order to incorporate the reactant ligand into SAMs, phosphonate alkanethiol 19 was synthesized. The activated imidazole carbamate 16 was prepared from the previously described diethyl phosphonate 15, by reaction with 1,1'-carbonyldiimidazole. 4-nitrophenyl activated phosphonate 17 was generated by chlorination of 16 with oxalyl chloride followed by substitution with 4-nitrophenol. Disulfide 18, which was prepared in a single step from the thiol, was coupled with intermediate 17 through formation of a urethane linkage. The disulfide protecting group was removed by DTT reduction to afford alkanethiol 19.

Imidazole carboxylic acid (diethoxy-phosphoryl)-undecyl ester 16.

To a solution of alcohol 15 (485 mg, 1.57 mmol) dissolved in 10 mL of $CH_2Cl_2$ was added freshly sublimed 1,1'-carbonyldiimidazole (510 mg, 3.15 mmol). After stirring at room temperature for 10 h, the reaction mixture was rinsed with $H_2O$ (2×10 mΩ). The organic layer was dried over $MgSO_4$ and concentrated to give 507 mg (80%) of pure 16 as a white solid. $^1$H NMR ($CDCl_3$, 500 MHz) δ 8.22 (s, 1H), 7.44 (s, 1H), 7.10 (s, 1H), 4.41 (t, J=6.5 Hz, 2H), 4.07 (m, 4H), 1.77 (m, 2H), 1.69 (m, 2H), 1.57 (m, 2H), 1.44-1.21 (br m, 20H). $^{31}$P NMR ($CDCl_3$, 500 MHz) δ 8.22.

Imidazole carboxylic acid [ethoxy-(4-nitrophenoxy)-phosphoryl]-undecyl ester 17. To a solution of 16 (1.2 g, 3.0 mmol) dissolved in 25 mL of $CH_2Cl_2$ was added oxalyl chloride (0.65 n-flL, 7.5 mmol) dropwise at 0° C. The reaction mixture was allowed to slowly warm to room temperature. After stirring for 8 h, the mixture was concentrated to remove excess oxalyl chloride. The crude residue was redissolved in 20 mL of $CH_2Cl_2$, followed by the addition of 4-nitrophenol (414 mg, 3.0 mmol) and $Et_3N$ (0.80 mL, 6.0 mmol). After stirring at room temperature for 10 h, the reaction mixture was concentrated. The residue was purified by flash chromatography (hexane/EA=1:1) to give 601 mg (41%) of pure 17. $^1$H NMR ($CDCl_3$, 500 MHz) δ 8.16 (d, J=9.0 Hz, 2H), 8.10 (s, 1H), 7.37 (s, 1H), 7.32 (d, J=9.0 Hz, 2H), 7.01 (s, 1H), 4.35 (t, J=6.5 Hz, 2H), 4.11 (m, 2H), 1.87 (m, 2H), 1.72 (m, 2H), 1.62 (m, 2H), 1.38-1.17 (br m, 20H). $^{31}$P NMR ($CDCl_3$, 500 MHz) δ 30.49.

2-(2-{2-[11-(Pyridin-2-yldisulfanyl)-undecyloxy]-ethoxy}-ethoxy)-ethyl-ammonium chloride 18. To a solution of 2-(2-[2-(11-Mercapto-undecyloxy)-ethoxyl-ethoxyl-ethyl-ammonium-chloridex (78 mg, 0.21 mmol) dissolved in 5 mL of MeOH was added 2,2'-dipyridyl disulfide, 2,2'-dithiodipyridine (ALDRITHIOL-2, ALDRICH) (93 mg, 0.42 mmol). After stirring at room temperature for 8 h, the reaction mixture was concentrated, and the residue was purified by flash chromatography ($CH_2Cl_2$/MeOH, 20:1 to 5:1) to afford 60 mg (60%) of disulfide 18. $^1$H NMR ($CDCl_3$, 500 MHz) δ 8.52 (s, 1H), 8.30 (br s, 3H), 7.78 (br s, 1H), 7.70 (br s, 1H), 7.07 (br s, 1H), 3.81 (t, J=5 Hz, 2H), 3.69-3.59 (br m, 6H), 3.55 (m, 2H), 3.43 (t, J=7 Hz, 2H), 3.20 (br, 2H), 2.78 (t, J=7.5 Hz, 2H), 1.68 (m, 2H), 1.55 (m, 2H), 1.34 (m, 2H), 1.31-1.17 (br, 12H).

11-[2-(2-{2-[11-(Pyridin-2-yldisulfanyl)-undecyloxy]-ethoxy}-ethoxy)-ethylcarbamoyloxy]-undecyl-phosphonic acid ethyl ester 4-nitro-phenyl ester. A solution of phosphonate 17 (68 mg, 0.14 mmol), amino disulfide 18 (60 mg, 0.13 mmol), and $Et_3N$ (35 mL, 0.25 mmol) dissolved in DMF was stirred at 60° C. for 66 h. After concentration of the reaction mixture, the crude residue was purified by column chromatography (hexane/EA=1:1) to afford the disulfide, which contained approximately 20% starting materials. $^1$H NMR ($CDCl_3$, 500 MHz) δ 8.44 (s, 1H), 8.32 (s, 1H), 8.21 (d, J=9 Hz, 2H), 7.78 (br s, 1H), 7.70 (br s, 1H), 7.32 (d, J=9.0 Hz, 2H), 7.07 (br s, 1H), 4.15 (m, 2H), 3.98 (m, 2H), 3.62-3.49 (br m, 10H), 3.45 (m, 2H), 3.32 (m, 2H), 2.78 (t, J=7.5 Hz, 2H), 1.90 (m, 2H), 1.79 (m, 2H), 1.71-1.44 (br m, 4H), 1.40-1.07 (br, 33H).

[11-(2-{2-[2-(11-Mercapto-undecyloxy)-ethoxy]-ethoxy}-ethylcarba moyloxy)-undecyl]-phosphonic acid ethyl ester 4-nitro-phenyl ester 19. To a solution of the crude disulfide dissolved in 5 mL of MeOH was added dithiothreitol (DTT) (154 mg, 1.0 mmol) and $Et_3N$ (28 gL, 0.2 mmol). The solution was stirred at room temperature for 20 h. After concentration, the residue was dissolved in 30 mL of $CH_2Cl_2$ and rinsed with $H_2O$ (2×10 mΩ). The organic layer was dried over $MgSO_4$ and concentrated. The crude residue was purified by column chromatography (hexane/EA=1:1) to give 22 mg (23% over 2 steps) of pure 19. $^1$H NMR ($CDCl_3$, 400 MHz) δ 8.21 (d, J=9 Hz, 2H), 7.35 (d, J=9.0 Hz, 2H), 4.19 (m, 2H), 3.98 (t, J=5.5 Hz, 2H), 3.62-3.51 (br m, 10H), 3.45 (t, J=6.8 Hz, 2H), 3.32 (m, 2H), 2.50 (q, J=7.2 Hz, 2H), 1.90 (m, 2H), 1.79 (m, 2H), 1.55 (m, 2H), 1.49-1.17 (br, 3.3H).

This synthesis may be illustrated by the following reaction scheme:

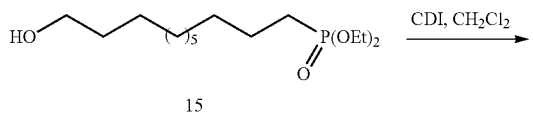

15

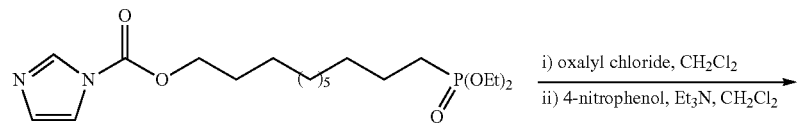

16

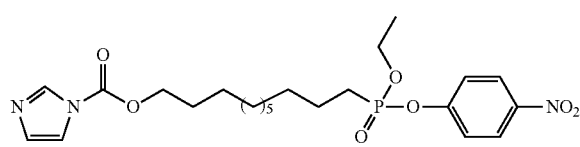

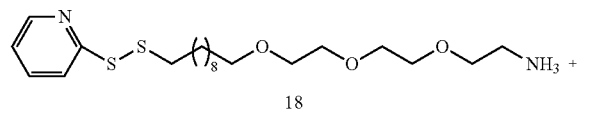

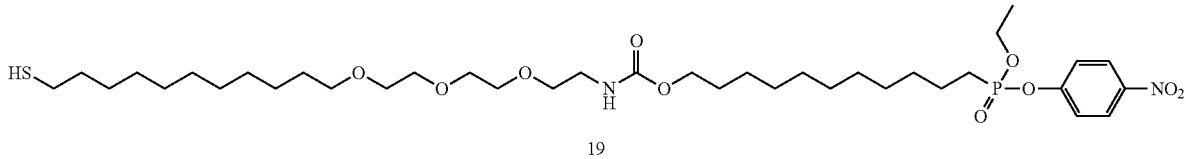

Example 10

Immobilization of Cutinase to SAM

Figure 13:
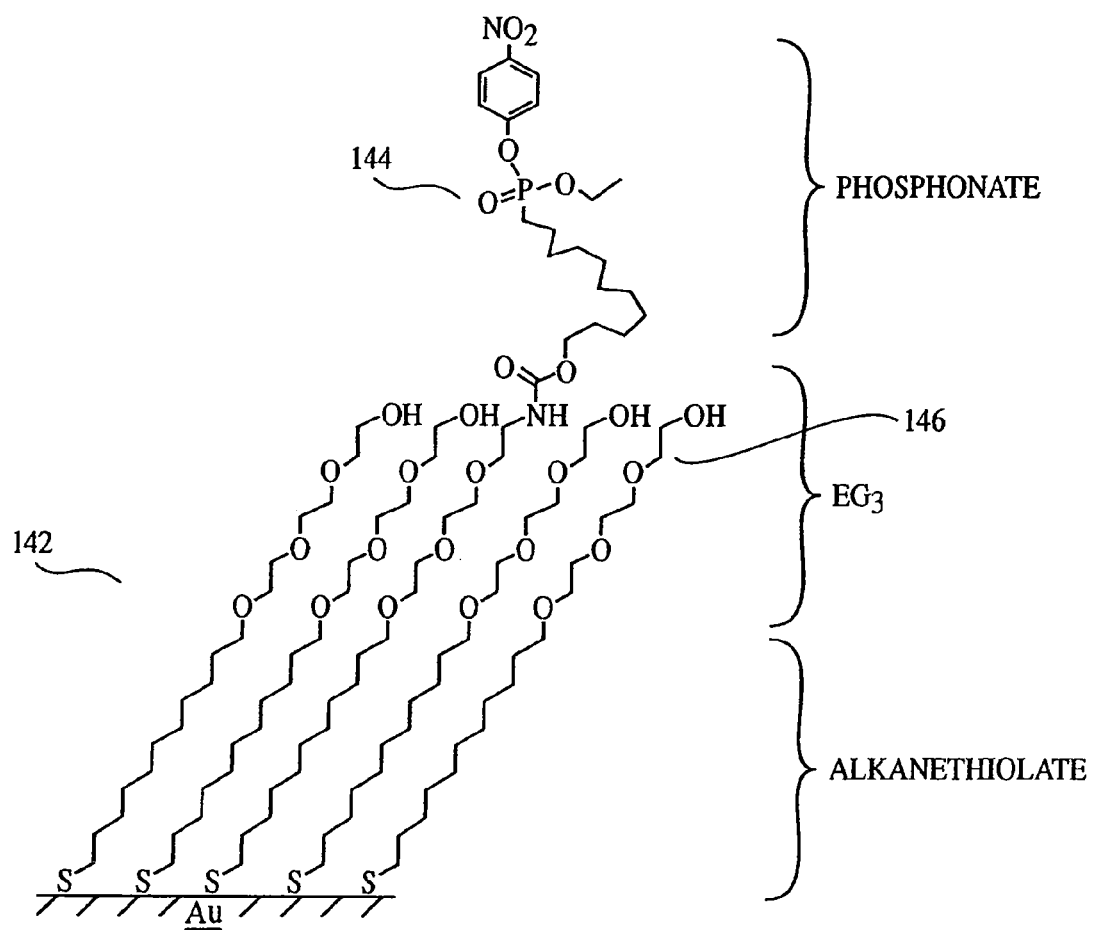
FIG. 13 is an illustration of the immobilization of a reactant ligand for cutinase.
Figure 14A:
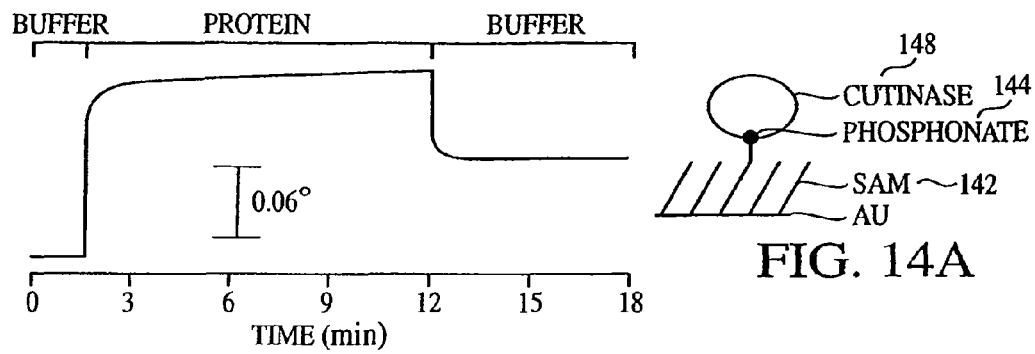
FIG. 14 is an illustration of the SPR sensograms showing the selective immobilization of cutinase.
Figure 14B:
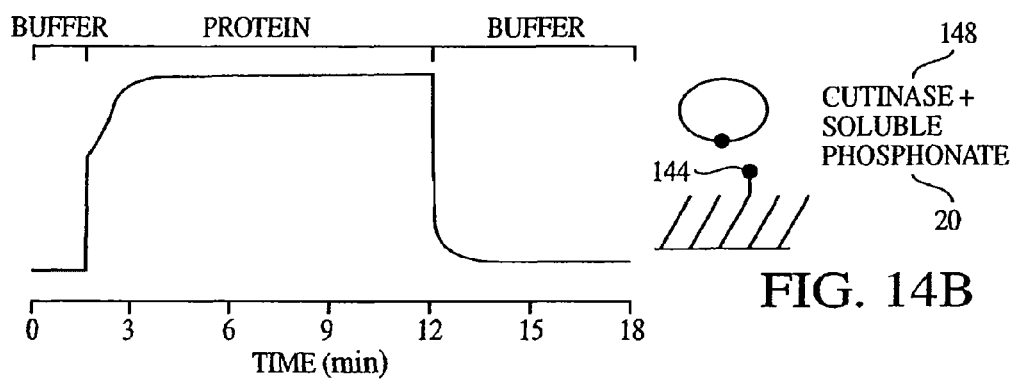
Figure 14C:
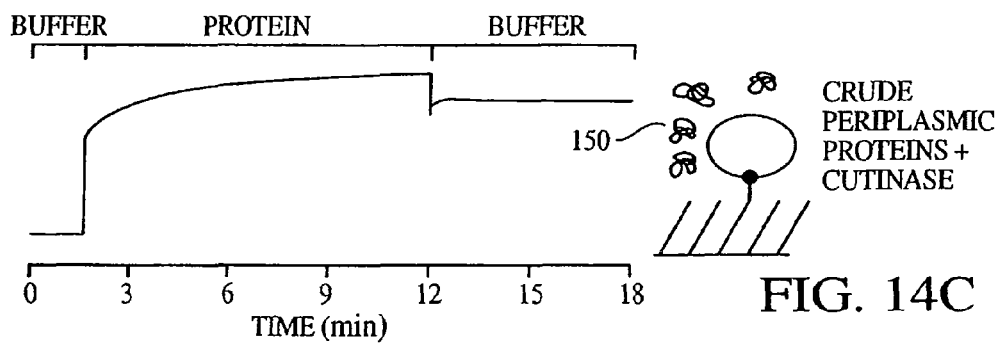
Figure 14D:
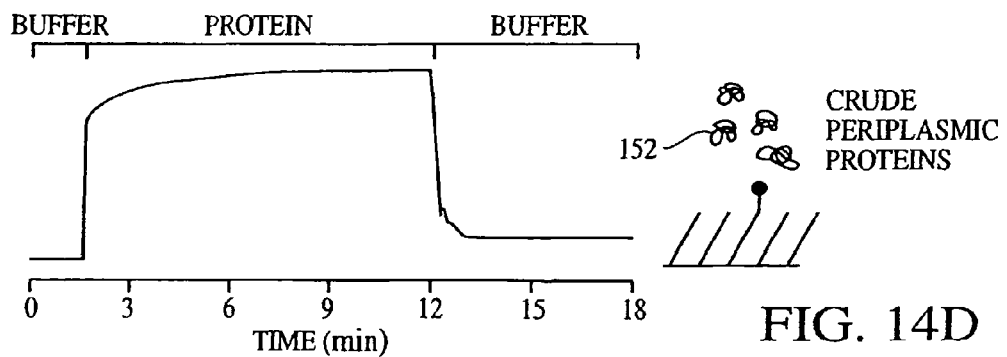

A self-assembled monolayer (SAM) 142 terminated in a phosphonate reactant ligand 144 was prepared (FIG. 13). The ligand was present at a low density mixed with tri(ethylene glycol) groups 146 which resist non-specific protein adsorption. The immobilization of cutinase 148 to the monolayer was characterized by SPR spectroscopy (FIG. 14). Phosphate buffered saline (pH 7.4) was flowed over the monolayer for 2 min to establish a baseline, followed by a solution of protein in the same buffer for 10 min to observe binding. Finally, the protein solution was replaced with buffer for 6 min to quantitate the amount of protein that was irreversibly immobilized. Cutinase (25 μM) bound irreversibly to the surface (FIG. 14A). Treatment of the monolayer with sodium dodecyl sulfate (SDS) (0.5 mg/mL) did not result in removal of cutinase from the surface, confirming that the immobilization was covalent. SDS is a detergent that serves to remove non-covalently immobilized molecules from a surface. Cutinase which was first blocked with 20 showed no binding to the surface (FIG. 14B), demonstrating that the immobilization was specific.

Crude *E. coli* periplasmic extracts obtained after transformation with the cutinase plasmid were tested for specific immobilization. Crude extract 150 was flowed over the monolayer and the same amount of binding was observed as in the case of purified cutinase (FIG. 14C), and remained the same after rinsing with SDS. Periplasmic lysate 152 of *E. coli* that was not transformed with the cutinase plasmid did not bind to the monolayer (FIG. 14D), demonstrating that the monolayer presenting the phosphonate ligand is resistant to non-specific protein adsorption and can be used to purify and immobilize cutinase.

Example 11

Dependence of Cutinase Concentration on Immobilization Efficiency

To be useful, the immobilization should be rapid even at low concentrations of cutinase. A range of cutinase concentrations was flowed over the phosphonate monolayer for 10 min and then washed with buffer.

Figure 15:
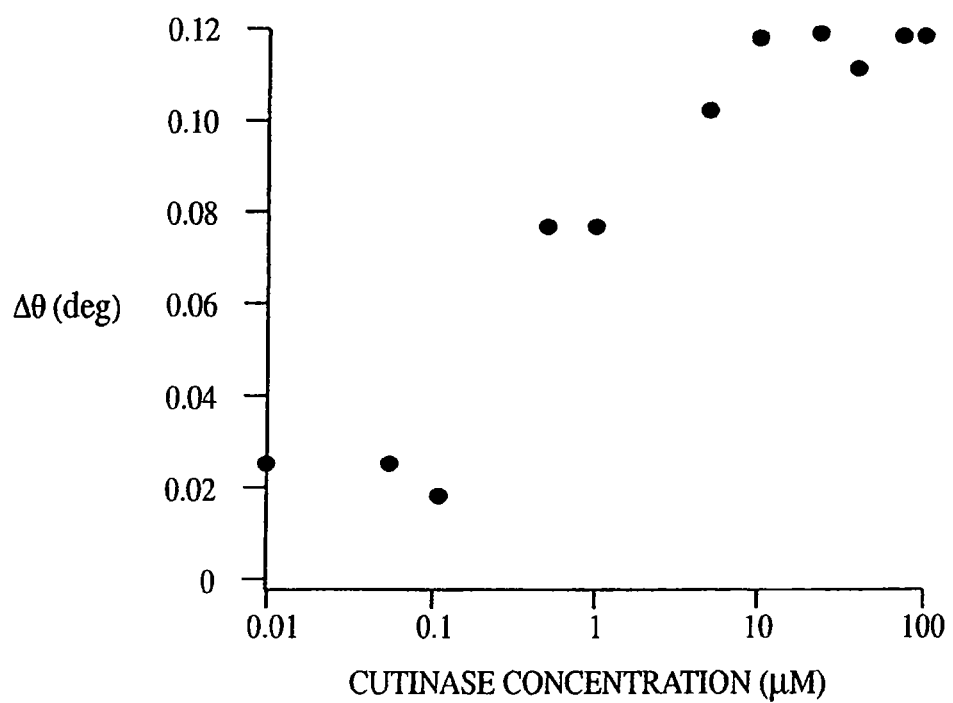
FIG. 15 is a graph of the immobilization of cutinase as a function of concentration.

The total amount of irreversible binding was plotted as a function of cutinase concentration (FIG. 15). Cutinase at a concentration of 10 μM resulted in complete immobilization of protein after 10 min while 0.5 μM resulted in 50% immobilization in 10 min.

Example 12

Synthesis of Soluble NTA-Quinone Conjugate n-Pentylhydroquinone 21. To the solution of 2.4 g (11.5 mmol) of n-Pentyldimethoxybenzene 1 in $CH_2Cl_2$ at −78° C., 5.4 ml (5 eq) of $BBr_3$ was added dropwise. After warming to room temperature, the reaction mixture was stirred for 4 hr. The $BBr_3$ was quenched with ethyl ether at −78° C., and then with water at room temperature. Extraction with $CH_2Cl_2$ and silicagel chromatography (hexane:EA=2:1) gave 2.07 g (quant.) of 21 as a white solid.

n-Pentylbenzoquinone 22. To the solution of 360 mg (2 mmol) of 21 in methanol, 650 mg (2 eq) of $FeCl_3$ was added. The reaction mixture was stirred for 1 hr, and the solvent was removed. Silicagel chromatography (hexane:EA=20:1) gave 210 mg (59% yield) 22 as a brown solid.

NTA-hydroquinone conjugate 23; and NTA-quinone conjugate 24. To the solution of 74 mg (0.415 mmol) of 22 in methanol, 98 mg (1 e) of 29 (NTA-SH) in methanol was added. The reaction mixture was stirred for 1 hr, and the solvent was removed. The trituration with hexane and ethyl ether (1:1 solution) gave the adduct 23 as a brown solid. This crude product was dissolved in 6.6 ml of $CH_2Cl_2$, and to this solution was added 0.83 ml of MeOH and 830 mg of silicagel. To this mixture, 140 mg of $NaClO_4$ in 0.83 ml of water was added with vigorous stirring. The reaction mixture was stirred for 1 hr, and the solvent was removed. HPLC purification (water/$CH_3CN$, gradient from 10% to 90% for 30 min., $t_r$=28 min.) gave 24 as a brown solid.

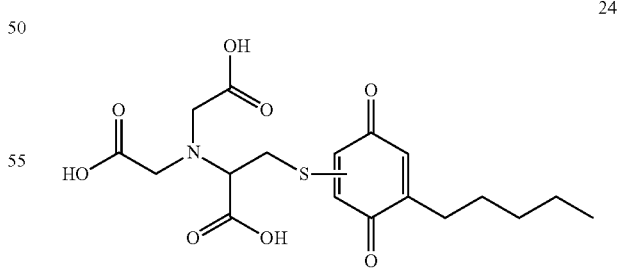

24

Example 13

Synthesis of Immobilizable NTA Reactant Ligand

Fmoc-Cys(Trt)-OMe 25; and $H_2N$-Cys(Trt)-OMe 26. 7.2 g (12.3 mmol) of Fmoc-Cys(Trt)-OH was dissolved in 70 ml of MeOH and added 1.5 ml of conc. sulfuric acid. The reaction mixture was refluxed for 4 hr, the solvent was removed. The mixture was then mixed with ethyl acetate, and washed with water, saturated NaHCO₃, and brine. Removing the solvent under vacuum gave 25 as a white foamy solid. The crude product was dissolved in 20 ml of 20% piperidine solution in DMF. After 2 hr, the solvent was removed. Silicagel chromatography ($CH_2Cl_2$: MeOH=10:1) gave 4.0 g (86% two step yield) of 26 as a white solid.

Nitrilo-trimethylester-S(Trt) 27. To the solution of 1.92 g (5.09 mmol) of 26 in DMF, 3.54 ml of DIEA (4 eq) and 1.92 ml (4 eq) of methylbromoacetate were added. The reaction mixture was stirred overnight at 50° C. and the solvent was removed. Silicagel chromatography (hexane: EA=2:1) gave 2.28 g (86% yield) of 27 as a pale yellow oil.

NTA-S(Trt) 28. To the solution of 2.28 g (4.37 mmol) of 27 in 15 ml of dioxane, 15 ml of 1N NaOH solution was added. The reaction mixture was stirred for 2 hr, acidified with 15 ml of 1N HCl solution, and extracted with $CH_2Cl_2$ (3×30 ml). The organic layer was combined and dried over $MgSO_4$. Removing the solvent under vacuum gave 1.27 g (61% yield) of 28 as a white solid.

NTA-SH 29. 470 mg (0.98 mmol) of 28 was dissolved in $CH_2Cl_2$, and to this solution was added 0.3 ml (2 eq) of triethylsilane and 5 ml of trifluoroacetic acid. The reaction mixture was stirred for 2 hr, and the solvent was removed. Trituration with hexane and ethyl ether (1:1 solution) gave 167 mg (72% yield) 29 as a white solid.

Hydroquinone-NTA-EG5-alkanethiol-trityl 30. 22 mg (0.0257 mmol) of Quinone-EG5-alkanethiol-trityl 11 was dissolved in methanol, and to this solution was added 6 mg (1 eq) of NTA-SH 29. The reaction mixture was stirred for 1 hr, and the solvent was removed. The trituration with hexane and ethyl ether (1:1 solution) gave 10 mg (36% yield) of the adduct 30 as a yellow solid.

Hydroquinone-NTA-EG5-alkanethiol 31. 10 mg (0.009 mmol) of 30 was dissolved in $CH_2Cl_2$, to this was added 2.9 µL (2 eq) of triethylsilane and 1 ml of TFA. The reaction mixture was stirred for 2 hr, and the solvent was removed. The trituration with hexane and ethyl ether (1:1 solution) gave 8 mg (quantitative) of 31 as a yellow solid.

by ~250 µm. Protein deposition onto the gold-supported monolayers is straightforward and reproducible with this device. Pin contact with the surface is relatively non-destructive, suggested by near complete wash-off of non-specific protein. Arraying GST fusion polypeptides onto the surfaces leads to specific and irreversible attachment. Glycerol may be used as a wetting agent. GST binding is relatively unaffected by glycerol concentrations up to 30%.

Prophetic Example 2

Cyclin-Dependent Kinase Assay

Well-characterized substrate proteins and controls are arrayed to test for activities of cyclin-dependent kinase catalytic subunits CDK1 and CDK2. A substrate common to essentially all CDK's is Histone H1. A large number of proteins, such as retinoblastoma protein (Rb), are well-characterized substrates of CDK2. An independent set, such as nuclear lamin, are substrates of CDK1. A set of 24 to 48 CDK1 and/or CDK2 substrates and controls are cloned as GST fusions, purified via glutathione affinity chromatography and tested for phosphorylation in standard in vitro kinase assays. Soluble, stable GST fusions which can be phosphorylated are spotted in a matrix onto the gold-supported monolayers with the AFFYMETRIX GMS417 arrayer. After incubation to allow binding, the arrays are washed free of unbound GST fusion polypeptides with a glutathione buffer and equilibrated with a standard in vitro kinase buffer. The surfaces are then reacted with ATP and CDK's reconstituted from recombinant components, whole cell extracts or CDK immunoprecipitates.

Detection is performed using the highly specific anti-phosphothreonine-proline monoclonal antibody from NEW ENGLAND BIOLABS and/or the generally available MPM2 anti-phospho-serine/threonine-proline monoclonal antibody. Secondary detection with fluorescent antibodies is performed as described above. Alternatively, the phospho-serine/threonine-proline binding WW domain of Pin1 may be synthesized and directly fluorescently labeled or expressed as a fusion polypeptide with RFP. Once probed, the arrays are scanned

31

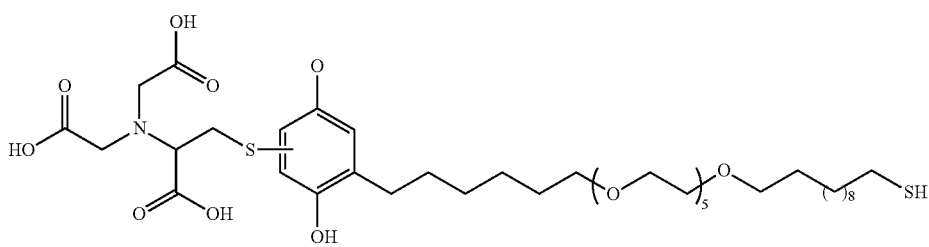

The following are prophetic examples:

Prophetic Example 1

Preparation of Array

Relatively small numbers of GST fusion polypeptides (from 10 to 50) are arrayed on standard gold coated glass slides. An AFFYMETRIX GMS417 pin-in-ring device intended for DNA arraying, is programmed to pick up fluids from multi-well plates and to deposit them onto flat surfaces in patterns of spots of ~150 µm diameter on centers separated and phosphorylation is quantitated for each substrate using the AFFYMETRIX GMS428 scanner.

An interesting application with which to test the robustness of such an array is offered by the "cycling extracts" that can be prepared from *Xenopus* clawed frog eggs. The CDK substrate chip is immersed in such an extract as it undergoes spontaneous cell cycles. The phosphorylation state of the chip, regulated by the CDK's and the antagonistic phosphatases in the extract, provide a real time probe of the changing state of the extract through time. This provides an initial model for an intracellular probe of cell proliferative state based on phosphorylation arrays.

Prophetic Example 3

Apoptosis Chip

Like the model substrates gelsolin and PARP, a selection of substrates is individually cloned as GST fusions, purified and arrayed onto a gold-supported monolayer. These arrays are then exposed to cell extracts and analyzed for cleavage of the caspase substrates. The vast majority of proven caspase substrates are already cloned and can be readily tested for stability and solubility when expressed as GST-RFP sandwiches. The loss of fluorescence from the surface after incubation with a cell extract would be used as a marker for cleavage of caspase substrates. A preferable detection method is to recognize the newly revealed carboxyl-terminal aspartate of the cleaved GST fusion polypeptide. This allows detection on the array surface of the accumulation of cleaved substrates using similar methods to those described above. Alternatively, the unmasked carboxyl-terminal aspartate can potentially be specifically chemically recognized via carbodiimide chemistry and crosslinking to a fluorescent group, also providing a positive signal for proteolysis of an arrayed substrate.

Obviously, numerous modifications and variations of the present invention are possible in light of the above teachings. It is therefore to be understood that within the scope of the appended claims, the invention may be practiced otherwise than as specifically described herein.

REFERENCES

EPO 402226. Transformation vectors for yeast *Yarrowia*. 1990.

WO 91/00357. New strain with filamentous fungi mutants, process for the production of recombinant proteins using said strain, and strains and proteins. 1991.

Alam, J., and J. L. Cook. 1990. Reporter genes: Application to the study of mammalian gene transcription. *Anal. Biochem.* 188:245-254.

Alligood, K. J., P. S. Charifson, R. Crosby, T. G. Consler, et al. 1998. The formation of a covalent complex between a dipeptide ligand and the src SH2 domain. *Bioorg Med Chem. Lett.* 8:1189-94.

Austin, C. P., and C. L. Cepko. 1990. Cellular migration patterns in the developing mouse cerebral cortex. *Development.* 110:713-732.

Ausubel, F. M., R. Brent, R. E. Kingston, D. D. Moore, et al. 1987. Current protocols in molecular biology. John Wiley & Sons, New York.

Bamdad, C. 1998. A DNA self-assembled monolayer for the specific attachment of unmodified double- or single-stranded DNA. *Biophys J.* 75:1997-2003.

Bandmann, N., E. Collet, J. Leijen, M. Uhlen, et al. 2000. Genetic engineering of the *Fusarium solani pisi* lipase cutinase for enhanced partitioning in PEG-phosphate aqueous two-phase systems. *J. Biotechnol.* 79:161-72.

Bechtold, N., and G. Pelletier. 1998. In planta *Agrobacterium*-mediated transformation of adult *Arabidopsis thaliana* plants by vacuum infiltration. *Methods Mol. Biol.* 82:259-66.

Becker, D. M., and L. Guarente. 1991. High-efficiency transformation of yeast by electroporation. *Methods Enzymol.* 194:182-187.

Beggs, J. D. 1978. Transformation of yeast by a replicating hybrid plasmid. *Nature.* 275:104-109.

Berger, J., J. Hauber, R. Hauber, R. Geiger, et al. 1988. Secreted placental alkaline phosphatase: A powerful new qunatitative indicator of gene expression in eukaryotic cells. *Gene.* 66:1-10.

Berggren, K., A. Nilsson, G. Johansson, N. Bandmann, et al. 2000. Partitioning of peptides and recombinant protein-peptide fusions in thermoseparating aqueous two-phase systems: effect of peptide primary structure. *J Chromatogr B Biomed Sci Appl.* 743:295-306.

Berman, H. A., and P. Taylor. 1978. Fluorescent phosphonate label for serine hydrolases, pyrenebutyl methylphosphonofluoridate: reaction with acetylcholinesterase. *Biochemistry.* 17:1704-13.

Blaydes, J. P., B. Vojtesek, G. B. Bloomberg, and T. R. Hupp. 2000. The development and use of phospho-specific antibodies to study protein phosphorylation. *Methods Mol Biol.* 99:177-89.

Bodine, D. M., K. T. McDonagh, N. E. Seidel, and A. W. Nienhuis. 1991. Survival and retrovirus infection of murine hematopoietic stem cells in vitro: effects of 5-FU and method of infection. *Exp. Hematol.* 19:206-212.

Brown, M. T., and J. A. Cooper. 1996. Regulation, substrates and functions of src. *Biochim Biophys Acta.* 1287:121-49.

Capecchi, M. R. 1980. High efficiency transformation by direct microinjection of DNA into cultured mammalian cells. *Cell.* 22:479.

Case, M. E., M. Schweizer, S. R. Kushner, and N. H. Giles. 1979. Efficient transformation of *Neurospora crassa* by utilizing hybrid plasmid DNA. *Proc Natl Aced Sci USA.* 76:5259-63.

Cepko, C. L., B. E. Roberts, and R. E. Mulligan. 1984. Construction and applications of a highly transmissible murine retrovirus shuttle vector. *Cell.* 37:1053-1062.

Chalfie, M., Y. tu, G. Euskirchen, W. W. Ward, at al. 1994. Green fluorescent protein as a marker for gene expression. *Science.* 263:302-805.

Chaney, W. G., D. R. Howard, J. W. Pollard, S. Sallustio, et al., 1986. High-frequency transfection of CHO cells using Polybrene. *Somatic Cell Mol. Genet.* 12:237.

Chapman, R., E. Ostuni, S. Takayama, R. Holmlin, et al. 2000. Surveying for surfaces that resist the adsorption of proteins. *J. Am. Chem. Soc.* 122:8303-8304.

Chen, C., and H. Okayama. 1988. Calcium phosphate-mediated gene transfer: A highly efficient system for stably transforming cells with plasmid DNA. *BioTechniques.* 6:632-638.

Chen, C. S., M. Mrksich, S. Huang, G. M. Whitesides, et al. 1997. Geometric control of cell life and death. *Science.* 276:1425-8.

Cohen, S. M. N., A. C. Y. Chang, and L. Hsu. 1972. Nonchromosomal antibiotic resistance in bacteria: Genetic transformation of *Escherichia coli* by R-factor DNA. *Proc. Natl. Acad. Sci. USA.* 69:2110.

de Louvencourt, L., H. Fukuhara, H. Heslot, and M. Wesolowski. 1983. Transformation of *Kluyveromyces lactis* by killer plasmid DNA. *J Bacteria* 154:737-42.

de Wet, J. R., K. V. Wood, M. DeLuca, D. R. Helinski, et al., 1987. Sturcture and expression in mammalian cells. *Mol. Cell. Biol.* 7:725-737.

Deussen, H. J., S. Danielsen, J. Breinholt, and T. V. Borchert. 2000a. Design and synthesis of triglyceride analogue biotinylated suicide inhibitors for directed molecular evolution of lipolytic enzymes. *Bioorg Med Chem Lett.* 10:2027-31.

Deussen, H. J., S. Danielsen, J. Breinholt, and T. V. Borchert. 2000b. A novel biotinylated suicide inhibitor for directed molecular evolution of lipolytic enzymes. *Bioorg Med Chem.* 8:507-13.

Eck, M. J. 1995. A new flavor in phosphotyrosine recognition. *Structure*. 3:421-4.

Elroy-Stein, O., and B. Moss. 1990. Cytoplasmic expression system based on constitutive synthesis of bacteriophage T7 RNA polymerase in mammalian cells. *Proc. Natl. Acad. Sci. USA*. 87:6743-6747.

Escudero, J., and B. Hohn. 1997. Transfer and integration of T-DNA without cell injury in the host plant. *Plant Cell*. 9:2135-2142.

Fekete, D. M., and C. L. Cepko. 1993. Retroviral infection coupled with tissue transplantation limits gene transfer in the chick embryo. *Proc. Natl. Acad. Sci. USA*. 90:2350-2354.

Feigner, P. L., T. R. Gadek, M. Holm, R. Roman, et al. 1987. Lipofectin: A highly efficient, lipid-mediated DNA/transfection procedure. *Proc. Natl. Acad. Sci. USA*. 84:7413-7417.

Fieck, A., D. L. Wyborski, and J. M. Short. 1992. Modifications of the *E. coli* Lac repressor for expression in eukaryotic cells: effects of nuclear signal sequences on protein activity and nuclear accumulation. *Nucleic Acids Res*. 20:1785-91.

Finer, J. J., K. R. Finer, and T. Ponappa. 1999. Particle bombardment-mediated transformation. *Current Topics in microbiology and immunology*. 240:59-80.

Fleer, R., P. Yeh, N. Amelial, I. Maury, et al. 1991. Stable multicopy vectors for high-level secretion of recombinant human serum albumin by *Kluyveromyces* yeasts. *Biotechnology* (NY). 9:968-75.

U.S. Pat. No. 5,804,604. Tat-derived transport polypeptides and fusion proteins. 1998.

Fromm, M., L. P. Taylor, and V. Walbot. 1985. Expression of genes transferred into monocot and dicot plant cells by electroporation. *Proc. Natl. Acad. Sci. USA*. 82:5824-5828.

Fujita, T., H. Shubiya, T. Ohashi, K. Yamanishi, et al. 1986. Regulation of human interleukin-2 gene: Functional DNA sequences in the 5' flanking region for the gene expression in activated T lymphocytes. *Cell*. 46:401-407.

Gallagher, S. R. 1992. GUS protocols: Using the GUS gene as a reporter of gene expression. Academic Press, San Diego, Calif.

Gietz, R. D., R. A. Woods, P. Manivasakam, and R. H. Schiestl. 1998. Growth and transformation of *Saccharomyces cerevisiae*. In Cells: A laboratory manual. Vol. I. D. Spector, R. Goldman, and L. Leinwand, editors. Cold Spring Harbor Press, Cold Spring Harbor, N.Y.

U.S. Pat. No. 6,194,550B1. Systematic polypeptide evolution by reverse translation. 2001.

Gorman, C. M., L. F. Moffat, and B. H. Howard. 1982. Recombinant genomes which express chloramphenicol acetyltransferase in mammalian cells. *Mol. Cell. Biol*. 2:1044-1051.

Graham, F. L., and A. J. van der Eb. 1973. A new technique for the assay of infectivity of human adenovirus 5 DNA. *Virology*. 52:456-.

Greene, and Wuts. 1991. Protective Groups in Organic Synthesis. Wiley & Sons.

Hanahan, D. 1983. Studies on transformation of *Escherichia coli* with plasmids. *J. Mol. Biol*. 166:557-580.

Hansen, G., and M.-D. Chilton. 1999. Lessons in gene transfer to plants by a gifted microbe. *Curr. Top. Microbiol. Immunol*. 240:21-57.

Hansen, G., and M. S. Wright 1999. Recent advances in the transformation of plants. *Trends Plant Sci*. 4:226-231.

Hinnen, A., J. B. Hicks, and G. R. Fink. 1978. Transformation of yeast. *Proc. Natl. Acad. Sci. USA*. 75:1929-1933.

Hodneland, C., and M. Mrksich. 2000. Biomolecular surfaces that release ligands under electrochemical control. *J. Am. Chem. Soc*. 122:4235-4236.

Hoffman, F. 1996. Laser microbeams for the manipulation of plant cells and subcellular structures. *Plant Sci*. 113:1-11.

Houseman, B. T., and M. Mrksich. 2001. The microenvironment of immobilized Arg-Gly-Asp peptides is an important determinant of cell adhesion. *Biomaterials*. 22:943-55.

Hunter, T. 1998. The Croonian Lecture 1997. The phosphorylation of proteins on tyrosine: its role in cell growth and disease. *Philos Trans R Soc Lond B Biol Sci*. 353:583-605.

Ishiura, M., S. Hirose, T. Uchida, Y. Hamada, et al. 1982. Phage particle-mediated gene transfer to cultured mammalian cells. *Molecular and Cellular Biology*. 2:607-616.

Ito, H., Y. Fukuda, K. Murata, and A. Kimura. 1983. Transformation of intact yeast cells treated with alkali cations. *J. Bacteriol*. 153:163-168.

Kaufman, R. J. 1990. Vectors used for expression in mammalian cells. *Methods Enzymol*. 185:487-511.

Kaufman, R. J., P. Murtha, D. E. Ingolia, C.-Y. Yeung, et al. 1986. Selection and amplification of heterologous genes encoding adenosine deaminase in mammalian cells. *Proc. Natl. Acad. Sci. USA*. 83:3136-3140.

Kawai, S., and M. Nishizawa. 1984. New procedure for DNA transfection with polycation and dimethyl sulfoxide. *Mol. Cell. Biol*. 4:1172.

Kelly, J. M., and M. J. Hynes. 1985. Transformation of *Aspergillus niger* by the amdS gene of *Aspergillus nidulans*. *Embo J*. 4:475-9.

U.S. Pat. No. 6,184,344B1. Synthesis of proteins by native chemical ligation. 2001.

Kim, Y. S., H. B. Lee, K. D. Choi, S. Park, et al. 1994. Cloning of *Pseudomonas fluorescens* carboxylesterase gene and characterization of its product expressed in *Escherichia coli*. *Biosci Biotechnol Biochem*. 58:111-6.

Kitz, R., and I. Wilson. 1962. *J. Biol. Chem*. 237:3245.

Leduc, N., and e. al. 1996. Isolated maize zygotes mimic in vivo embryogenic development and express microinjected genes when cultured in vitro. *Dev. Biol*. 10:190-203.

Lemischka, I. R., D. H. Raulet, and R. C. Mulligan. 1986. Developmental potential and dynamic behavior of hematopoietic stem cells. *Cell*. 45:917-927.

Littlefield, J. W. 1964. Selection of hybrids from matings of fibroblasts in vitro and their presumed recombinants. *Science*. 145:709-710.

WO 01/04265. C-terminal protein tagging. 2001.

Longhi, S., and C. Cambillau. 1999. Structure-activity of cutinase, a small lipolytic enzyme. *Biochim Biophys Acta*. 1441:185-96.

Lopata, M. A., D. W. Cleveland, and B. Sollner-Webb. 1984. High-level expression of a chloramphenicol acetyltransferase gene by DEAEdextran-mediated DNA traansfection couled with a dimethylsulfoxide or glycerol shock treatment. *Nucleic Acids Research*. 12:5707.

Luckow, V. A. 1991. Cloning and expression of heterologous genes in insect cells with baculovirus vectors. In Recombinant DNA technology and applications. A. Prokop, R. K. Bajpai, and C. Ho, editors. McGraw-Hill, New York. 97-152.

Luk, Y.-Y., M. Kato, and M. Mrksich. 2000. Self-assembled monolayers of alkanethiolates presenting mannitol groups are inert to protein adsorption and cell attachment. *Langmuir*. 16:9604-9608.

Mandel, M., and A. Higa. 1970. Calcium-dependent bacteriophage DNA infection. *J. Mol. biol*. 53:159-162.

March, J. 1994. Advanced Organic Chemistry. Wiley & Sons.

Martinez, C., P. De Geus, M. Lauwereys, G. Matthyssens, et al. 1992. *Fusarium solani* cutinase is a lipolytic enzyme with a catalytic serine accessible to solvent. Nature. 356: 615-8.

Martinez, C., A. Nicolas, H. van Tilbeurgh, M. P. Egloff, et al., 1994. Cutinase, a lipolytic enzyme with a preformed oxyanion hole. *Biochemistry.* 33:83-9.

Miller, A. D., and C. Buttimore. 1986. Redesign of retrovirus packaging cell lines to avoid recombination leading to helper virus production. *Mol. Cell. biol.* 6:2895-2902.

Miller, L. K. 1988. Baculoviruses as gene expression vectors. *Annu. Rev. Microbiol.* 42:177-199.

Morrison, and boyd. 1983. Organic Chemistry. Allyn and Bacon, Inc.

Mrksich, M. 2000. A surface chemistry approach to studying cell adhesion. *Chem. Soc. Rev.* 29:267-273.

Mrksich, M., L. E. Dike, J. Tien, D. E. Ingber, et al. 1997. Using microcontact printing to pattern the attachment of mammalian cells to self-assembled monolayers of alkanethiolates on transparent films of gold and silver. *Exp Cell Res.* 235:305-13.

Mrksich, M., and G. Whitesides. 1995. *TIBTECH.* 13:228-235.

Myers, J., S. Antonelli, and T. Widlanski. 1997. Motifs for metallophosphatase inhibition. *J. Am. Chem. Soc.* 119: 3163-3164.

Neumann, E., M. Schaefer-Ridder, Y. Wang, and P. H. Hofschneider. 1982. Gene transfer into mouse lyoma cells by electroporation in high electric fields. *EMBO J.* 1:841-845.

Okabayashi, Y., Y. Sugimoto, N. F. Totty, J. Hsuan, et al. 1996. Interaction of Shc with adaptor protein adaptins. *J Biol. Chem.* 271:5265-9.

O'Reilly, D. R., L. K. Miller, and V. A. Luckow. 1992. Baculovirus expression vectors. W.H. Freeman and Company, New York.

Ou-Lee, T. M., R. Turgeon, and R. Wu. 1986. Uptake and expression of a foreign gene linked to either a plant virus or *Drosophila* promoter in protoplasts of rice, wheat and sorghum. *Proc. Natl. Acad. Sci. USA.* 83:6815-6819.

Palmer, T. D., R. A. Hock, W. R. A. osborne, and A. D. Miller. 1987. Efficient retrovirus-mediated transfer and expression of a human adenosine deaminase gene in diploid skin fibroblasts from an adenosie-deficient human. *Proc. Natl. Acad. Sci. USA.* 84:1055-1059.

Pear, W., G. Nolan, M. Scott, and D. Baltimore. 1993. Production of high-titer helper-free retroviruses by transient transfection. *Proc. Natl. Acad. Sci. USA.* 90:8392-8396.

Potter, H. 1988. Electroporation in biology: Methods, applications, and instrumentation. *Analytical Biochemistry.* 174:361-373.

Potter, H., L. Weir, and P. Leder. 1984. Enhancer-dependent expression of human kappa immunoglobulin genes introduced into mouse pre-B lymphocytes by electroporation. *Proc. Natl. Acad. Sci. USA.* 81:7161-7165.

Rassoulzadegan, M., B. Binetruy, and F. Cuzin. 1982. High frequency of gene transfer after fusion between bacteria and eukaryotic cells. *Nature.* 295:257.

Rhodes, C. A., D. A. Pierce, I. J. Mettler, D. Mascarenhas, et al. 1988. Genetically transformed maize plants from protoplasts. *Science.* 240:204-207.

Roberts, C., C. Chen, M. Mrksich, V. Martichonok, et al. 1998. *J Am Chem Soc.* 120:6548-6555.

Rose, J. K., L. Buonocore, and M. Whitt. 1991. A new cationic liposome reagent mediating nearly quantitative transfection of animal cells. *BioTechniques.* 10:520-525.

Sandri-Goldin, R. M., A. L. Goldin, J. C. Glorioso, and M. Levine. 1981. High-frequency transfer of cloned herpes simjplex virus type I sequences to mammalian cells by protoplast fusion. *Mol. Cell. Biol.* 1:7453-752.

Saunders, J. A., B. F. Matthews, and P. D. Miller. 1989. Plant gene transfer using electrofusion and electroporation. In Electroporation and electrofusion in cell biology. E. Neumann, A. E. Sowers, and C. A. Jordan, editors. Plenum Press, New York. 343-354.

Sawyer, T. K. 1998. Src homology-2 domains: structure, mechanisms, and drug discovery. *Biopolymers.* 47:243-61.

Schaffner, W. 1980. Direct transfer of cloned genes from bacteria to mammalian cells. *Proc. Natl. Acad. Sci. USA.* 77:2163.

Scheidt, K. A., W. R. Roush, J. H. McKerrow, P. M. Selzer, et al. 1998. Structure-based design, synthesis and evaluation of conformationally constrained cysteine protease inhibitors. *Bioorg Med. Chem.* 6:2477-94.

Selden, R. F., K. Burke-Howie, M. E. Rowe, H. M. Goodman, et al. 1986. Human growth hormone as a reporter gene in regulation studies employing transient gene expression. *Molecular and Cellular Biololgy.* 6:3173-3179.

Shigekawa, K., and W. J. Dower. 1988. Electroporation of eukaryotes and prokaryotes: A general approach to the introduction of macomolecules into cells. *BioTechniques.* 6:742-751.

Shillito, R. 1999. Methods of genetic transformations: Electroporation and polyethylene glycol treatment. In Molecular improvement of cereal crop. I. Vasil, editor. Kluwer, Dordrecht, The Netherlands. 9-20.

Simonsen, C. C., and A. D. Levinson. 1983. Isolation and expression of an altered mouse dihydrofolate reductase cDNA. *Proc. Natl. Acad. Sci. USA.* 80:2495-2499.

Smith, D. B., and K. S. Johnson. 1988. Single-step purification of polypeptides expressed in *Escherichia coli* as fusions with glutathione S-transferase. *Gene.* 67:31-40.

Southern, P. J., and P. Berg. 1982. Transformation of mammalian cells to antibiotic resistanced with a bacterial gene under control of the SV40 early region promoter. *J. Mol. Appl. Gen.* 1:327-341.

Sreekrishna, K., R. H. Potenz, J. A. Cruze, W. R. McCombie, et al. 1988. High level expression of heterologous proteins in methylotrophic yeast *Pichia pastoris. J Basic Microbiol.* 28:265-78.

Stowell, J., T. Widlanski, T. Kutateladze, and R. Raines. 1995. Mechanism-based inactivation of ribonuclease A. *J. Org. Chem.* 60:6930-6936.

U.S. Pat. No. 6,214,553 B1. Libraries of protein encoding RNA-protein fusions. 2001.

U.S. Pat. No. 6,207,446B1. Selection of proteins using RNA-protein fusions. 2001.

Thomas, S. M., and J. S. Brugge. 1997. Cellular functions regulated by Src family kinases. *Annu Rev Cell Dev Biol.* 13:513-609.

Thompson, J. A., and e. al. 1995. Maize transformation utilizing silicon carbide whiskers: A review. *Euphytica.* 85:75-80.

Tilburn, J., C. Scazzocchio, G. G. Taylor, J. H. Zabicky-Zissman, et al. 1983. Transformation by integration in *Aspergillus nidulans. Gene.* 26:205-21.

Touraev, A., and e. al. 1997. Plant male germ line transformation. *Plant J.* 12:949-956.

Trick, H. N., and e. al. 1997. Recent advances in soybean transformation. *Plant Tissue Cult. Biotechnol.* 3:9-26.

Turner, D. L., E. Y. Snyder, and C. L. Cepko. 1990. Lineage-independent determination of cell type in the embryonic mouse retina. *Neuron.* 4:833-845.

van Ommen, B., J. H. Ploemen, J. J. Bogaards, T. J. Monks, et al. 1991. Irreversible inhibition of rat glutathione S-transferase 1-1 by quinones and their glutathione conjugates. Structure-activity relationship and mechanism. *Biochem J.* 276:661-6.

van Ommen, B., J. H. Ploemen, H. J. Ruven, R. M. Vos, et al. 1989. Studies on the active site of rat glutathione S-transferase isoenzyme 4-4. Chemical modification by tetrachloro-1,4-benzoquinone and its glutathione conjugate. *Eur J. Biochem.* 181:423-9.

Violette, S. M., W. C. Shakespeare, C. Bartlett, W. Guan, et al. 2000. A Src SH2 selective binding compound inhibits osteoclast-mediated resorption. *Chem. Biol.* 7:225-35.

White, D., N. Belyaev, and B. Turner. 1999. Preparation of site-specific antibodies to acetylated histones. *Methods.* 19:417-424.

Whitt, M. A., L. Buonocore, J. K. Rose, V. Ciccarone, et al. 1990. TransfectACE reagent promotes transient transfection frequencies greater than 90%. *Focus.* 13:8-12.

Wigler, M., A. Pellicer, S. Silversttein, and R. Axel. 1978. Biochemical transfer of single-copy eucaryotic genes using total cellular DNA as donor. *Cell.* 14:725.

Williams, D. A., I. R. Lemischka, D. G. Nathan, and R. C. Mulligan. 1984. Introduction of a new genetic material into pluripotent haematopoietic stem cells of the mouse. *Nature.* 310:476-480.

Wong, T. K., and E. Neumann. 1982. Electric field mediated gene transfer. *Biochemical and Biophysical Research Communications.* 107:584-587.

Wu, S. Y., and J. E. Casida. 1995. Ethyl octylphosphonofluoridate and analogs: optimized inhibitors of neuropathy target esterase. *Chem Res Toxicol.* 8:1070-5.

Wyborski, D. L., L. C. DuCoeur, and J. M. Short. 1996. Parameters affecting the use of the lac repressor system in eukaryotic cells and transgenic animals. *Environ Mol. Mutagen.* 28:447-58.

Wyborski, D. L., and J. M. Short. 1991. Analysis of inducers of the *E. coli* lac repressor system in mammalian cells and whole animals. *Nucleic Acids Res.* 19:4647-53.

Yelton, M. M., J. E. Hamer, and W. E. Timberlake. 1984. Transformation of *Aspergillus nidulans* by using a trpC plasmid. *Proc Natl Acad Sci USA.* 81:1470-4.

Yousaf, M., B. Houseman, and M. Mrksich. 2001. Turning on cell migration with electroactive substrates. *Angew. Chem. Int. Ed.* 40:1093-1096.

Zhou, G., and e. al. 1983. Introduction of exogenous DNA into cotton embryos. *Methods Enzymol.* 101:433-481.

---

The invention claimed is:

1. A method, comprising:
   a) providing a plurality of hydrolase reactant ligands covalently attached to a substrate;
   b) contacting said substrate and said hydrolase reactant ligands attached to said substrate with a plurality of fusion polypeptides, wherein each of said fusion polypeptides comprising a hydrolase capture polypeptide fused to a display polypeptide, under conditions such that said hydrolase reactant ligands covalently binds to said hydrolase capture polypeptides; and
   c) analyzing said display polypeptide;
   wherein said hydrolase reactant ligands reacts specifically with the hydrolase capture polypeptide to form the covalent bond.

2. The method of claim 1, wherein said substrate comprises at least one member selected from the group consisting of metal, metal oxide, glass, ceramic, quartz, silicon, polymer, sepharose, agarose, a colloid, a lipid bilayer, and a lipid monolayer.

3. The method of claim 1, wherein said display polypeptide comprises a polypeptide of interest to be immobilized to said substrate.

4. The method of claim 1, wherein said fusion polypeptide is made from a fusion gene encoding said hydrolase capture polypeptide fused to said display polypeptide.

5. The method of claim 1, wherein said hydrolase capture polypeptide comprises cutinase.

6. The method of claim 1, wherein said fusion polypeptides are covalently bound to said substrate in step b).

7. The method of claim 6, wherein said plurality of bound fusion polypeptides are organized into an array.

8. The method of claim 1, wherein said analyzing said display polypeptide comprises exposing said display polypeptide to a biomolecule and analyzing the interaction between said display polypeptide and said biomolecule.

9. The method of claim 1, wherein said analyzing said display polypeptide comprises determining an amount of said display polypeptide, or a molecule bound thereto, attached to said substrate.

10. The method of claim 1, wherein said analyzing said display polypeptide comprising assaying for enzyme activity.

11. The method of claim 1, wherein said analyzing said display polypeptide comprises detecting the binding of a biomolecule to said display polypeptide.

12. The method of claim 11, wherein said biomolecule comprises an antibody.

13. The method of claim 1, wherein said fusion polypeptide is expressed in a host cell.

* * * * *